(12) United States Patent
Kang et al.

(10) Patent No.: US 10,087,204 B2
(45) Date of Patent: Oct. 2, 2018

(54) METHODS AND COMPOSITIONS FOR SUBSTITUTED ALPHA-AMINOPHOSPHONATE ANALOGUES

(71) Applicant: The Board of Regents of the Nevada System of Higher Education on Behalf of the University of Nevada, Las Vegas, Las Vegas, NV (US)

(72) Inventors: Jun Yong Kang, Henderson, NV (US); Karimulla Mulla, Atlanta, GA (US)

(73) Assignee: THE BOARD OF REGENTS OF THE NEVADA SYSTEM OF HIGHER EDUCATION ON BEHALF OF THE UNIVERSITY OF NEVADA, Las Vegas, NV (US)

( * ) Notice: Subject to any disclaimer, the term of this patent is extended or adjusted under 35 U.S.C. 154(b) by 0 days.

(21) Appl. No.: 15/436,608

(22) Filed: Feb. 17, 2017

(65) Prior Publication Data

US 2017/0267707 A1    Sep. 21, 2017

Related U.S. Application Data

(60) Provisional application No. 62/309,674, filed on Mar. 17, 2016.

(51) Int. Cl.
    *C07F 9/6584* (2006.01)
(52) U.S. Cl.
    CPC .............................. *C07F 9/65848* (2013.01)
(58) Field of Classification Search
    CPC .................................................. C07F 9/65848
    USPC ........................................................ 544/57
    See application file for complete search history.

(56) References Cited

PUBLICATIONS

Ovchinnikov et al. Zhurnal Obshchei Khimii (1984), 54(8), 1916-17.*
U.S. Appl. No. 62/309,674, filed Mar. 17, 2016, Jun Yong Kang et al.
Allen et al. (1978) Phosphonopeptides, a New Class of Synthetic Antibacterial Agents. Nature. 272:56-8.
Amar, H. et al. (2008) Thiomorpholin-4-ylmethyl-phosphonic Acid and Morpholin-4-methyl-phosphonic Acid as Corrosion Inhibitors for Carbon Steel in Natural Seawater. Mater Chem Phys. 110(1):1-6.
Azizi, K. et al. (2014) A Catalyst-Free Synthesis of α-Aminophosphonates in Glycerol. Tet Lett. 55(52):7236-9.
Azizi, N. and M.R. Saidi (2003) Synthesis of Tertiary α-Amino Phosphonate by One-Pot Three-Component Coupling Mediated by LPDE. Tetrahedron. 59(28):5329-32.
Bartrum, H.E. et al. (2013) Continuous-Flow Generation of Diazoesters and Their Direct Use in S—H and P—H Insertion Reactions: Synthesis of α-Sulfanyl, α-Sulfonyl, and α-Phosphono Carboxylates. Tetrahedron. 69(10):2276-82.
Beck, J.F. et al. (2013) Palladium Catalyzed Intermolecular Hydroamination of 1-Substituted Allenes: an Atom-Economical Method for the Synthesis of N-Allylamines. RSC Advances. 3(43):20708-18.
Berge, S.M. et al. (1977) Pharmaceutical Salts. J Pharm Sci. 66(1):1-19; p. 2.
Bhagat, S. and A.K. Chakraborti (2007) An Extremely Efficient Three-Component Reaction of Aldehydes/Ketones, Amins, and Phosphites (Kabachnik-Fields Reaction) for the Synthesis of α-Aminophosphonates Catalyzed by Magnesium Perchlorate. J Org Chem. 72(4)1 263-70.
Blom, K.F. et al. (2004) Preparative LC-MS Purification: Improved Compound Specific Method Optimization. J Combi Chem. 6(6):874-83.
Chaudhary, P. et al. (2006) Synthesis and Antimicrobial Activity of N-Alkyl and N-Aryl Piperazine Derivatives. Bioorg Med Chem. 14(6):1819-26.
Doak, G.O. and L.D. Freedman (1961) The Structure and Properties of the Dialkyl Phosphonates. Chem Rev. 61(1):31-44.
Fields, E.K. (1952) The Synthesis of Esters of Substituted Amino Phosphonic Acids. J Am Chem Soc. 74(6):1528-31.
Ghosh, S. et al. (2004) Effects of Bisphosphonates on the Growth of *Entamoeba histolytica* and *Plasmodium* Species in Vitro and in Vivo. J Med Chem. 47(1):175-87.
Hammond, P.R. (1962) 258. Ionisation of the P—H Bond. Deuterium-Exchange Studies with Diethyl and Ethyl Hydrogen Phosphonate. J Chem Soc. 0:1365-9.
Handbook of Pharmaceutical Salts: Properties, Selection, and Use, Wiley-VCH, 2002.
Kabachnik and Medved (1952) Dokl Akad Nauk SSSR. 83(1):689-92.
Kafarski, P. and B. Lejczak (1991) Biological Activity of Aminophosphonic Acids. Phosphorus, Sulfur Silicon Relat Elem. 63:193-215.
Kasthuraiah, M. et al. (2007) Syntheses, Spectral Property, and Antimicrobial Activities of 6-a-Amino Dibenzo [d,f][1,2,3] Dioxaphosphepin 6-Oxides. Heteroat Chem. 18(1):2-8.
Kumar, A. et al. (2014) Cinchona-Derived Thiourea Catalyzed Hydrophosphonylation of Ketimines—an Enantioselective Synthesis of α-Amino Phosphonates. Tetrahedron. 70(39):7044-9.
Lavielle, G. et al. (1991) New a-Amino Phosphonic Acid Derivatives of Vinblastine: Chemistry and Antitumor Activity. J Med Chem. 34(7):1998-2003.
Lee, J.H. (2010) Characterization and Structure of Dhlp, a Phosphonate O-Methyltranferase Involved in DehydrophosBiosynthesis. Proc Natl Acad Sci USA. 107(41):17557-62.
Lewkowski, J. et al. (2015) Synthesis of Some Aminophosphonates Bearing N-(Fluorophenyl)-piperazynyl Moiety and Their Activity Toward Serotonin Receptors. Heteroat Chem. 26(4):290-8.

(Continued)

*Primary Examiner* — Kahsay Habte
(74) *Attorney, Agent, or Firm* — Ballard Spahr LLP

(57) ABSTRACT

Provided herein are α-aminophosphonates and methods for making same. Also provided are N-heterocyclic phosphines (NHPs) useful in metal-free phosphorus-carbon bond forming reactions such as, for example, in the preparation of α-aminophosphonates. This abstract is intended as a scanning tool for purposes of searching in the particular art and is not intended to be limiting of the present invention.

19 Claims, 3 Drawing Sheets

(56) References Cited

PUBLICATIONS

Ma, J.A. (2006) Catalytic Asymmetric Synthesis of α- and β-Amino Phosphonic Acid Derivatives. Chem Soc Rev. 35(7):630-6.

Makarov, M.V. et al. (2015) Synthesis of Diethyl (aryl)(4-oxopiperidin-1-yl)methylphosphonates. Mendeleev Commun. 25(3):232-3.

Malamari, F. and S. Khaksar (2014) Pentafluorophenylammonium triflate (PFPAT): A New Organocatalyst for the One-Pot Three-Component Synthesis of α-Aminophosphonates. J Chem Sci. 126(3):807-11.

Malhiac et al. (1996) A Convenient Direct Synthesis of α-N,N-Dialkylaminophosphonates Under Aprotic Conditions. Phosphorus, Sulfur Silicon Relat Elem. 113(1-4):299-301.

Ma'mani, L. et al. (2009) Nanohydroxyapatite Micropheres as a Biocompatible and Recoverable Catalyst for Synthesis of Carbon—Phosphorous Bond Formation. Curr Org Chem. 13(7):758-62.

March's Advanced Organic Chemistry: Reactions, Mechanisms, and Structure, 5th ed., Wiley-Interscience Publication, 2001.

Mastryukova, T.A. et al. (1980) Dyadic Phosphorus-Carbon Tautomerism. Pure Appl Chem. 52(4):945-57.

Mucha, A. et al. (2011) Remarkable Potential of the α-Aminophosphonate/Phosphinate Structural Motif in Medicinal Chemistry. J Med Chem. 54(17):5955-80.

Mulla, K. et al. (2016) Utility of Bifunctional N-Heterocyclic Phosphine (NHP)-Thioureas for Metal-Free Carbon-Phosphorus Bond Construction Toward Regio- and Steroselective Formation of Vinylphosphonates. J Org Chem. 81(1):77-88.

Naydenova, E. et al. (2007) Synthesis, Cytotoxicity and Clastogenicity of Novel α-Aminophosphonic Acids. Amino Acids. 33(4):695-702.

Nazish, M. et al. (2014) Magnetic $Fe_3O_4$ Nanoparticle-Supported Phosphotungstic Acid as a Recyclable Catalyst for the Kabachnik-Fields Reaction of Isatins, Imines, and Aldehydes under Solvent-Free Conditions. ChemPlusChem. 79(12):1753-60.

Ordóñez, M. et al. (2009) An Overview of Seteroselective Synthesis of α-Aminophosphonic Acids and Derivatives. Tetrahedron. 65(1):17-49.

Palacios, F. et al. (2005) Synthesis of β-Aminophosphonates and -Phosphinates. Chem Rev. 105(3):899-932.

Petrusson, S. et al. (1997) Protecting Groups in Carbohydrate Chemistry. J Chem Educ. 74(11):1297.

Prauda, I. et al. (2007) Efficient Synthesis of Phosphono- and Phosphinoxidomethylated N-Heterocycles Under Solvent-Free Microwave Conditions. Synth Commun. 37(2):317-22.

Protecting Group Chemistry, 1st Ed., Oxford University Press. 2000.

Pudovik, A.N. and I.V. Konoalova (1979) Addition Reactions of Esters of Phosphorus(III) Acids with Unsaturated Systems. Synthesis. 1979(2):81-96.

Qian, C. and T. Huang (1998) One-Pot Synthesis of α-Amino Phosphonates from Aldehydes Using Lanthenide Triflate as a Catalyst. J Org Chem. 63(12):4125-8.

Rascol, O. et al. (1989) Calcium Antagonists and the Vestibular System: A Critical Review of Flunarizine as an Antivertigo Drug. Fundamental Clin Pharmacol. 3(S1):79s-87s.

Reddy, B.R.P. et al. (2015) Efficient Solvent Free Synthesis of Tertiary α-Aminophosphonates Using $H_2Ti_3O_7$ Nanotubes as a Reusable Solid-Acid Catalyst. New J Chem. 39:9605-10.

Reddy, B.V.S. et al. (2011) Nano $Fe_3O_4$ as Magnetically Recyclable Catalyst for the Synthesis of α-Aminophosphonates in Solvent-Free Conditions. Tetrahedron Lett. 52(12):1359-62.

Remington's Pharmaceutical Sciences, 17th ed. Mack Publishing Company, Easton, PA, 1985, p. 1418.

Shakhmaev, R.N. et al. (2015) Iron-Catalyzed Synthesis of Cinnarizine. Rus J Org Chem. 51(1):95-7.

Sheykhan et al. (2011) Sulfamic Acid Heterogenized on Hydroxyapatite-Encapsulated γ-$Fe_2O_3$ Nanoparticles as a Magnetic Green Interphase Catalyst. J Mol Catal A: Chem. 335(1-2):253-61.

Shupak, A. et al. (1994) Cinnarizine in the Prophylaxis of Seasickness: Laboratory Vestibular Evaluation and Sea Study. Clin Pharmacol Ther. 55(6):670-80.

Singh, B.N. (1986) The Mechanism of Action of Calcium Antagonists Relative to Their Clinical Applications. Br J Clin Pharmac. 21(Suppl 2):109S-21S.

Sobhani, S. et al. (2014) Synthesis of Phosphoric Acid Supported on Magnetic Core-Shell Nanoparticles: a Novel Recyclable Heterogeneous Catalyst for Kabachnik-Fields Reaction in Water. RSC Adv. 4(30):15797-806.

Stawinski, J. and A. Kraszewski (2002) How to Get the Most Out of Two Phosphorus Chemistries. Studies on H-Phosphonates. Acc Chem Res. 35(11):952-60.

Suyama, K. et al. (2010) Highly Enantioselective Hydrophosphonylation of Aldehydes: Base-Enhanced Aluminum-salalen Catalysis. Angew Chem Int Ed. 49(4):797-9.

Todd, P.A. and P. Benfield (1989) Flunarizine. A Reappraisal of Its Pharmacological Properties and Therapeutic Use in Neurological Disorders. Drugs. 38(4):481-99.

Towse, G. (1980) Cinnarizine—A Labyrinthine Sedative. J Laryngol Otol. 94(9):1009-15.

Wadsworth, W.S. (1977) Synthetic Applications of Phosphoryl-Stabilized Anions. Org React. 73-253.

Wilder-Smith, C.H. et al. (1991) Cinnarizine for Prevention of Nausea and Vomiting During Platin Chemotherapy. Acta Oncologica. 30(6):731-4.

Xie, Y. et al. (2012) Palladium-Catalyzed Vinylation of Animals with Simple Alkenes: A New Strategy to Construct Allylamines. J Amer Chem Soc. 134(51):20613-6.

Yang, R. et al. (2004) Discovering Selective Agonists of Endothelial Target for Acetylcholine (ETA) via Diversity-Guided Pharmacophore Simplification and Simulation. Bioorg Med Chem Lett. 14(12):3017-25.

Younes, S. (1994) Diethyl Benzylpiperazinomethyl and Benzylpiperazinomethylbenzyl Phosphonates as Calcium Inhibitors. J Pharm Belg. 49(2):119-25 (Abstract included; 1 page).

Zakharov, S.V. et al. (2004) Synthesis and Acid-Base Properties of a-Aminophosphoryl Compounds. Russ J Gen Chem. 74(6):873-81.

\* cited by examiner

METHODS AND COMPOSITIONS FOR SUBSTITUTED ALPHA-AMINOPHOSPHONATE ANALOGUES

CROSS-REFERENCE TO RELATED APPLICATIONS

This application claims the benefit of U.S. Provisional Application No. 62/309,674, filed on Mar. 17, 2016, which is incorporated herein fully by reference in its' entirety.

BACKGROUND

Aminophosphonates have attracted great attention among scientists including chemists, biochemists, and biologists due to their broad spectrum of biomedical applications. They are well known as pharmaceutically and biologically important compounds. Due to intensive studies on aminophosphonate derivatives in medicinal chemistry, various aminophosphonate derivatives including α-aminophosphonates, β-aminophosphonates, and γ-aminophosphonates have been synthesized over the past several decades (Palacios et al. (2005) *Chemical Reviews* 105(3): 899-932; Bhagat et al. (2007) *The Journal of Organic Chemistry* 72(4): 1263-1270; Ordonez et al. (2009) *Tetrahedron* 65(1): 17-49; Mucha et al. (2011) *Journal of Medicinal Chemistry* 54(17): 5955-5980; Naydenova et al. (2007) *Amino Acids* 33(4): 695-702; Lavielle et al. (1991) *Journal of Medicinal Chemistry* 34(7): 1998-2003).

α-N-heterocyclic phosphonic acids and their derivatives such as morpholine (Ghosh et al. (2004) *J. Med. Chem.* 47: 175-187; Yang et al. (2004) *Bioorg. Med. Chem. Lett.* 14: 3017-3025), piperazinyl (Yang et al. (2004) *Bioorg. Med. Chem. Lett.* 14: 3017-3025; Chaudhary et al. (2006) *Bioorg. Med. Chem.* 14: 1819-1826; Younes (1994) *J. Pharm. Belg.* 49: 119-125), or thiomorpholino-methyl phosphonates (Amar et al. (2008) *Mater. Chem. Phys.* 110: 1-6) are an important class of amino phosphonate compounds. They have received considerable interest from a number of areas, ranging from medicinal chemistry to materials sciences. Morpholino-methyl bisphosphonic acid has shown antimalarial activity (Ghosh et al. (2004) *J. Med. Chem.* 47: 175-187) and the morpholino-aryl-methyl phosphonate has been realized as an effective agonist of endothelial target for acetylcholine (ETA) (Yang et al. (2004) *Bioorg. Med. Chem. Lett.* 14: 3017-3025). Piperazinyl-methyl phosphonate derivatives have proven to be potent active pharmaceutical ingredients such as agonists of ETA (Yang et al. (2004) *Bioorg. Med. Chem. Lett.* 14: 3017-3025), antibacterial agents (Chaudhary et al. (2006) *Bioorg. Med. Chem.* 14: 1819-1826), calcium antagonists (Younes (1994) *J. Pharm. Belg.* 49: 119-125), and serotonin receptors (Lewkowski et al. (2015) *Heteroat. Chem.* 26: 290-298). These significant biological activities of α-amino phosphonates are associated with the structural analogues of the corresponding amino acids and mimics of the transition state of peptide hydrolysis (Kafarski and Lejczak (1991) *Phosphorus, Sulfur Silicon Relat. Elem.* 63: 193-215; Allen et al. (1978) *Nature* 272: 56-58). In addition, thiomorpholino-methyl phosphonic acid is known as an effective corrosion inhibitor for carbon steel in seawater (Amar et al. (2008) *Mater. Chem. Phys.* 110: 1-6).

Since the pioneering early work by Kabachnick and Fields in 1952 (Fields (1952) *J. Am. Chem. Soc.* 74: 1528-1531; Kabachnik and Medved (1952) *Doklady Akademii Nauk SSSR* 83: 689-692), the multicomponent reaction involving amine, aldehyde, and dialkyl phosphonate has emerged as a straightforward protocol towards α-aminophosphonic acid esters. This transformation proceeds via an in-situ imine formation, followed by phospha-Mannich reaction (Pudovik reaction) (Pudovik and Konovalova (1979) *Synthesis* 81-96) between phosphite nucleophile and imine electrophile, constructing an N-C-P motif. This method offers important advantages such as a simple one-pot process and a rapid increase of molecular complexity using readily available starting materials. Recently, with the surging interest in the application of α-N-heterocyclic phosphonate derivatives to medicinal and materials chemistry, a considerable emphasis has been placed on the reaction system that utilizes cyclic secondary amines. Phospha-Mannich reaction employing primary amine has been well exploited (Ordonez et al. (2009) *Tetrahedron* 65: 17-49; Azizi et al. (2014) *Tet. Lett.* 55: 7236-7239; Qian and Huang (1998) *J. Org. Chem.* 63: 4125-4128; Kasthuraiah et al. (2007) *Heteroat. Chem.* 18: 2-8), however, secondary amine involved reactions are scarcely developed. Dialkyl phosphonates stable towards hydrolysis and oxidation due to the lack of lone pair electrons have been extensively used for this phosphonylation to form a C—P bond (Stawinski and Kraszewski (2002) *Acc. Chem. Res.* 35: 952-960; Doak and Freedman (1961) *Chem. Rev.* 61: 31-44; Ma (2006) *Chem. Soc. Rev.* 35: 630-636; Kumar et al. (2014) *Tetrahedron* 70: 7044-7049; Suyama et al. (2010) *Angew. Chem. Int. Ed.* 49: 797-799; Sobhani et al. (2014) *RSC Adv.* 4: 15797-15806). They, however, are unreactive phosphorus species. On the other hand, trialkyl phosphites are highly reactive nucleophiles but they are susceptible to spontaneous aerobic oxidation to form inactive phosphates (Stawinski and Kraszewski (2002) *Acc. Chem. Res.* 35: 952-960; Doak and Freedman (1961) *Chem. Rev.* 61: 31-44; Ma (2006) *Chem. Soc. Rev.* 35: 630-636). Thus, strategies for generating highly nucleophilic phosphite species in-situ using dialkyl phosphonates for phospha-Mannich reaction have been developed over the past decades. The dialkyl phosphonates are activated by Lewis acids (Bhagat and Chakraborti (2007) *J. Org. Chem.* 72: 1263-1270) or magnetic nanoparticles (Reddy et al. (2015) *New J. Chem.* 39: 9605-9610; Ma'mani et al. (2009) *Curr. Org. Chem.* 13: 758-762; Reddy et al. (2011) *Tetrahedron Lett.* 52: 1359-1362; Nazish et al. (2014) *Chem Plus Chem* 79: 1753-1760; Sheykhan et al. (2011) *J. Mol. Catal. A: Chem.* 335: 253-261) to generate the nucleophilic dialkyl phosphites, which rapidly react with imminium intermediates to ultimately construct the α-N-heterocyclic phosphonates. Brønsted acid-catalyzed reaction with dialkyl phosphonates (Malamiri et al. (2014) *J. Chem. Sci.* 126: 807; Prauda et al. (2007) *Synth. Commun.* 37: 317-322; Zakharov et al. (2004) *Russ. J. Gen. Chem.* 74: 873-881) and Lewis acid-mediated transformation involving trialkyl phosphites (Makarov et al. (2015) *Mendeleev Commun.* 25: 232-233; Azizi and Saidi (2003) *Tetrahedron* 59: 5329-5332; Malhiac et al. (1996) *Phosphorus, Sulfur Silicon Relat. Elem.* 113: 299-301) are important alternative routes for the synthesis of tertiary α-aminophosphonates.

Despite the great efforts devoted to the synthesis of biologically significant α-N-heterocyclic phosphonates, there remain limitations such as the use of toxic metals, low product yields with especially secondary amines, and harsh reaction conditions (elevated temperatures and basic conditions). Consequently, the development of a general and direct method of phosphonylation for accessing various α-aminophosphonates under metal-free mild reaction conditions is highly desirable in synthetic organic chemistry. These needs and others are met by the present invention.

SUMMARY

In accordance with the purpose(s) of the invention, as embodied and broadly described herein, the invention, in one aspect, relates to N-heterocyclic phosphines and methods of using these complexes for the preparation of, for example, vinylphosphonates.

Disclosed are compounds having a structure represented by a formula:

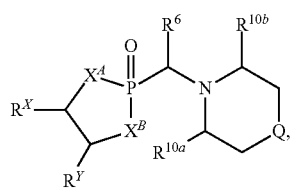

wherein Q is selected from O, S, C=O, S=O, SO$_2$, and NR$^1$; wherein each of X$^A$ and X$^B$ is independently selected from NR$^1$, O, and S; wherein each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups; wherein each occurrence of R$^5$, when present, is independently selected from halogen, —NO$_2$, —CN, —OH, —SH, —NH$_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O) (C1-C3 alkyl), —(S=O)(C1-C3 alkyl), —SO$_2$(C1-C3 alkyl), —CO$_2$R$^{11}$, —(C=O)NR$^{12a}$R$^{12b}$, —SO$_2$NR$^{12a}$R$^{12b}$, —O(C=O)NR$^{12a}$R$^{12b}$, —NHSO$_2$NR$^{12a}$R$^{12b}$, and —NH(C=O)NR$^{12a}$R$^{12b}$; wherein each occurrence of R$^{11}$, when present, is independently selected from hydrogen and C1-C4 alkyl; wherein each occurrence of R$^{12a}$ and R$^{12b}$, when present, is independently selected from hydrogen and C1-C3 alkyl; wherein each of R$^X$ and R$^Y$ is independently selected from hydrogen, C1-C8 alkyl, C6-C10 aryloxy, C6-C10 aryl, and 4-10 membered heteroaryl, or wherein each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups; wherein R$^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; and wherein each of R$^{10a}$ and R$^{10b}$ is independently selected from hydrogen and C1-C4 alkyl, or a salt thereof.

Also disclosed are compounds having a structure represented by a formula:

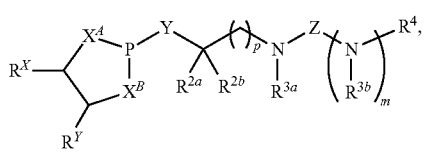

wherein m is selected from 0 and 1; wherein p is selected from 0, 1, 2, 3, 4, and 5; wherein Y is selected from CH$_2$, CH(CH$_3$), O, and S; wherein each of X$^A$ and X$^B$ is independently selected from NR$^1$, O, and S; wherein each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups; wherein each occurrence of R$^5$, when present, is independently selected from halogen, —NO$_2$, —CN, —OH, —SH, —NH$_2$, C1-C3 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl (C1-C3 alkoxy), C1-C3 alkylamino, (C1-C3)(C1-C3) dialkylamino, C3-C7 cycloalkyl, C6-C10 aryl, —(C=O) (C1-C3 alkyl), —(S=O)(C1-C3 alkyl), —SO$_2$(C1-C3 alkyl), —CO$_2$R$^{11}$, —(C=O)NR$^{12a}$R$^{12b}$, —SO$_2$NR$^{12a}$R$^{12b}$, —(C=O)NR$^{12a}$R$^{12b}$, —NHSO$_2$NR$^{12a}$R$^{12b}$, and —NH(C=O)NR$^{12a}$R$^{12b}$; wherein each occurrence of R$^{11}$, when present, is independently selected from hydrogen and C1-C4 alkyl; wherein each occurrence of R$^{12a}$ and R$^{12b}$, when present, is independently selected from hydrogen and C1-C3 alkyl; wherein Z is selected from C=O, C=S, S=O, SO$_2$, and a structure represented by a formula:

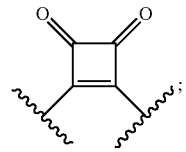 [SMILES: *c1c(*)c(=O)c1=O]

wherein each of R$^{2a}$ and R$^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; wherein each of R$^{3a}$ and R$^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of R$^{3a}$ and R$^{3b}$ is independently substituted with 0, 1, 2, 3, or 4 independently selected R$^5$ groups; and wherein R$^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, and 4-10 membered heteroaryl, and —(C1-C3 alkyl)(C6-C10 aryl), and substituted with 0, 1, 2, 3, or 4 independently selected R$^5$ groups, provided that Z is a structure represented by a formula:

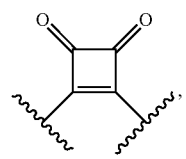

or
provided that each of R$^{2a}$ and R$^{2b}$ is not hydrogen, or a salt thereof.

Also disclosed are methods of making a disclosed compound.

Also disclosed are pharmaceutical compositions comprising the disclosed compounds.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1A:
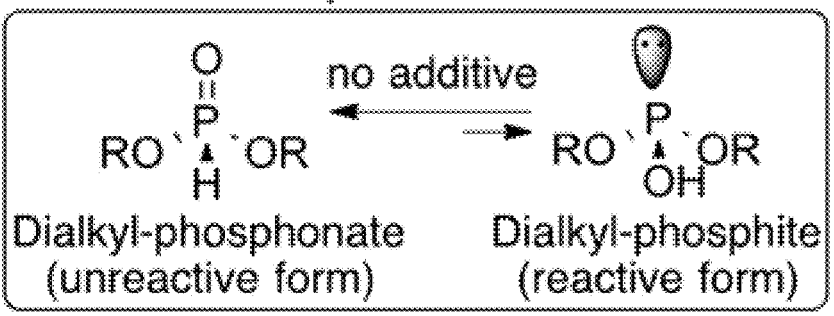
FIG. 1A-C show a representative image of the tautomeric equilibria of H-phosphonates without (1A) and with (1B) additive and a NHP-thiourea reagent (1C).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure which are, for brevity, described in the context of a single aspect, can also be provided separately or in any suitable subcombination.

For the terms "for example" and "such as," and grammatical equivalences thereof, the phrase "and without limitation" is understood to follow unless explicitly stated otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts thereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

In various aspects, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds (i.e., ┊|) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line, and at least one additional simple line, encompass a single enantiomeric series of all possible diastereomers.

Resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range that includes the endpoints, wherein n and m are integers and indicate the number of carbons. Examples include $C_{1-4}$, $C_{1-6}$, and the like.

As used herein, the term "$C_{n-m}$ alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In various aspects, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In various aspects, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In various aspects, the alkynyl moiety contains 2 to 6, 2 to 4, or 2 to 3 carbon atoms.

As used herein, the term "$C_{n-m}$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "$C_{n-m}$ alkoxy," employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In various aspects, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In various aspects, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In various aspects, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In various aspects, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In various aspects, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In various aspects, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In various aspects, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl," employed alone or in combination with other terms, refers to a —C(=O)— group, which may also be written as C(O).

As used herein, the term "cyano-C$_{1-3}$ alkyl" refers to a group of formula —(C$_{1-3}$ alkylene)-CN.

As used herein, the term "HO—C$_{1-3}$ alkyl" refers to a group of formula —(C$_{1-3}$ alkylene)-OH.

As used herein, the term "C$_{1-3}$ alkoxy-C$_{1-3}$ alkyl" refers to a group of formula —(C$_{1-3}$ alkylene)-O(C$_{1-3}$ alkyl).

As used herein, the term "carboxy" refers to a group of formula —C(O)OH.

As used herein, the term "di(C$_{n-m}$-alkyl)amino" refers to a group of formula —N(alkyl)$_2$, wherein the two alkyl groups each has, independently, n to m carbon atoms. In various aspects, each alkyl group independently has 1 to 6, 1 to 4, or 1 to 3 carbon atoms.

As used herein, the term "di(C$_{n-m}$-alkyl)carbamyl" refers to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halo" refers to F, Cl, Br, or I. In various aspects, the halo group is F or Cl.

As used herein, "C$_{n-m}$ haloalkoxy" refers to a group of formula —O-haloalkyl having n to m carbon atoms. An example haloalkoxy group is OCF$_3$. In various aspects, the haloalkoxy group is fluorinated only. In various aspects, the alkyl group has 1 to 6, 1 to 4, or 1 to 3 carbon atoms.

As used herein, the term "C$_{n-m}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amine group (i.e., primary amine base), di-substituted amine group (i.e., secondary amine base), or a tri-substituted amine group (i.e., tertiary amine base). Example mono-substituted amine bases include methyl amine, ethyl amine, propyl amine, butyl amine, and the like. Example di-substituted amine bases include dimethylamine, diethylamine, dipropylamine, dibutylamine, pyrrolidine, piperidine, azepane, morpholine, and the like. In various aspects, the tertiary amine has the formula N(R')$_3$, wherein each R' is independently C$_{1-6}$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl are optionally substituted by 1, 2, 3, 4, 5, or 6 C$_{1-6}$ alkyl groups. Example tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula N(R)$_3$, wherein each R is independently a linear or branched C$_{1-6}$ alkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons (C$_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In various aspects, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "aryl," employed alone or in combination with other terms, refers to an aromatic hydrocarbon group, which may be monocyclic or polycyclic (e.g., having 2, 3 or 4 fused rings). The term "C$_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, and nitrogen. In various aspects, the heteroaryl ring has 1, 2, 3, or 4 heteroatom ring members independently selected from nitrogen, sulfur and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur and oxygen. In various aspects, the heteroaryl has 5-6 ring atoms and 1 or 2 heteroatom ring members independently selected from nitrogen, sulfur and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the π-system through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro groups (e.g., —NO$_2$), haloalkyl groups (e.g., —CH$_2$F, —CHF$_2$, —CF$_3$, and the like), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)$_2$). In various aspects, the electron withdrawing group is selected from the group consisting of halo, C$_{2-6}$ alkenyl, C$_{2-6}$ alkynyl, C$_{1-3}$ haloalkyl, CN, NO$_2$, C(=O)OR$^{a1}$, C(=O)R$^{b1}$, C(=O)NR$^{c1}$R$^{d1}$, C(=O)SR$^{e1}$, —NR$^{c1}$S(O)R$^{e1}$, —NR$^{c1}$S(O)$_2$R$^{e1}$, S(=O)R$^{e1}$, S(=O)$_2$R$^{e1}$, S(=O)NR$^{c1}$R$^{d1}$, S(=O)$_2$NR$^{c1}$R$^{d1}$, and P(O)(OR$^{a1}$)$_2$. In various aspects, the electron withdrawing group is selected from the group consisting of C(=O)OR$^{a1}$, C(=O)R$^{b1}$, C(=O)NR$^{c1}$R$^{d1}$, C(=O)SR$^{e1}$, S(=O)R$^{e1}$, S(=O)$_2$R$^{e1}$, S(=O)NR$^{c1}$R$^{d1}$, and S(=O)$_2$NR$^{c1}$R$^{d1}$. In various aspects, the electron withdrawing group is C(=O)OR$^{a1}$. In various aspects, the electron withdrawing group is C(=O)OR$^{a1}$, wherein R$^{a1}$ is C$_{1-6}$ alkyl or (C$_{6-10}$ aryl)-C$_{1-3}$ alkylene. In various aspects, the electron withdrawing group is an ester.

Preparation of the compounds described herein can involve a reaction in the presence of an acid or a base. Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Example weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. Example bases include, without limitation, lithium hydroxide, sodium hydroxide, potassium hydroxide, lithium carbonate, sodium carbonate, potassium carbonate, sodium bicarbonate, and amine bases. Example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, t-butyl, trimethylsilyl and cyclohexyl substituted amides (e.g., lithium N-isopropylcyclohexylamide).

The following abbreviations may be used herein: AcOH (acetic acid); aq. (aqueous); atm. (atmosphere(s)); Br$_2$ (bromine); Bn (benzyl); calc. (calculated); d (doublet); dd (doublet of doublets); DCM (dichloromethane); DMF (N,N-dimethylformamide); Et (ethyl); Et$_2$O (diethyl ether); EtOAc (ethyl acetate); EtOH (ethanol); EWG (electron withdrawing group); g (gram(s)); h (hour(s)); H$_2$ (hydrogen gas); HCl (hydrochloric acid/hydrogen chloride); HPLC (high performance liquid chromatography); H$_2$SO$_4$ (sulfuric acid); Hz (hertz); I$_2$ (iodine); IPA (isopropyl alcohol); J (coupling constant); KOH (potassium hydroxide); K$_3$PO$_4$ (potassium phosphate); LCMS (liquid chromatography—mass spectrometry); LiICA (lithium N-isopropylcyclohexylamide); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaBH$_3$CN (sodium cyanoborohydride); NHP (N-heterocyclic phosphine); NHP—Cl (N-heterocyclic phosphine chloride); Na$_2$CO$_3$ (sodium carbonate); NaHCO$_3$ (sodium bicarbonate); NaOH (sodium hydroxide); Na$_2$SO$_4$ (sodium sulfate); nM (nanomolar); NMR (nuclear magnetic resonance spectroscopy); PCl$_3$ (trichlorophosphine); PMP (4-methoxyphenyl); RP-HPLC (reverse phase high performance liquid chromatography); t (triplet or tertiary); t-Bu (tert-butyl); TEA (triethylamine); TFA (trifluoroacetic acid); THF (tetrahydrofuran); TLC (thin layer chromatography); μg (microgram(s)); μL (microliter(s)); μM (micromolar); wt % (weight percent).

B. α-AMINOPHOSPHONATES

In one aspect, the invention relates to α-aminophosphonates useful as intermediates in, for example, the synthesis of cinnarizine and flunarizine, known antihistamine and antivertiginous pharmaceuticals, respectively. The use of the disclosed α-aminophosphonates as intermediates in the synthesis of other pharmaceutically active compounds is also envisioned.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

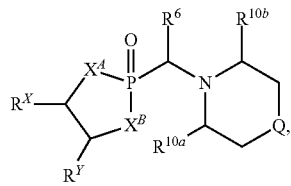

wherein Q is selected from O, S, C=O, S=O, SO$_2$, and NR$^1$; wherein each of X$^A$ and X$^B$ is independently selected from NR$^1$, O, and S; wherein each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups; wherein each occurrence of R$^5$, when present, is independently selected from halogen, —NO$_2$, —CN, —OH, —SH, —NH$_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O)(C1-C3 alkyl), —S(=O)(C1-C3 alkyl), —SO$_2$(C1-C3 alkyl), —CO$_2$R$^{11}$, —(C=O)NR$^{12a}$R$^{12b}$, —SO$_2$NR$^{12a}$R$^{12b}$, —O(C=O)NR$^{12a}$R$^{12b}$, —NHSO$_2$NR$^{12a}$R$^{12b}$, and —NH(C=O)NR$^{12a}$R$^{12b}$; wherein each occurrence of R$^{11}$, when present, is independently selected from hydrogen and C1-C4 alkyl; wherein each occurrence of R$^{12a}$ and R$^{12b}$, when present, is independently selected from hydrogen and C1-C3 alkyl; wherein each of R$^X$ and R$^Y$ is independently selected from hydrogen, C1-C8 alkyl, C6-C10 aryloxy, C6-C10 aryl, and 4-10 membered heteroaryl, or wherein each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups; wherein R$^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; and wherein each of R$^{10a}$ and R$^{10b}$ is independently selected from hydrogen and C1-C4 alkyl, or a salt thereof.

In a further aspect, the compound has a structure represented by a formula selected from:

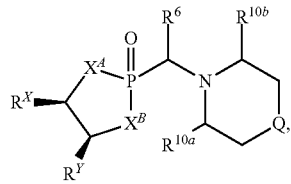

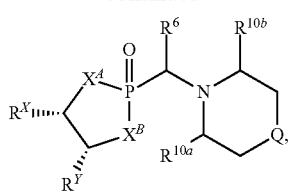

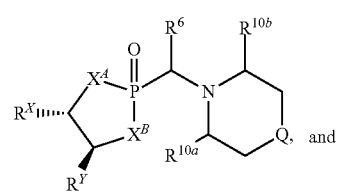

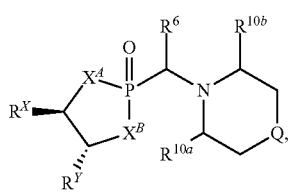

or a salt thereof.

In a further aspect, the compound has a structure represented by a formula selected from:

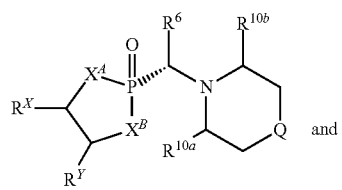

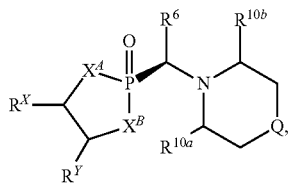

or a salt thereof.

In a further aspect, the compound has a structure represented by a formula:

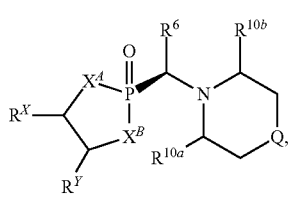

or a salt thereof.

In a further aspect, the compound has a structure represented by a formula:

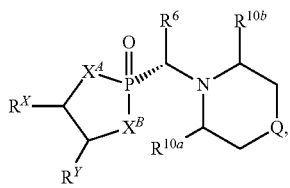

or a salt thereof.

In a further aspect, the compound has a structure represented by a formula:

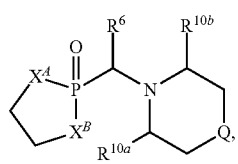

or a salt thereof.

In a further aspect, the compound has a structure represented by a formula:

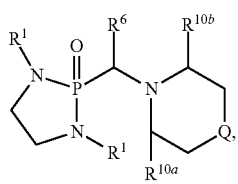

or a salt thereof.

In a further aspect, the compound has a structure represented by a formula:

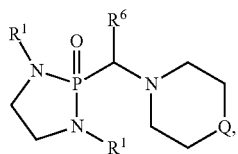

or a salt thereof.

In a further aspect, the compound has a structure represented by a formula:

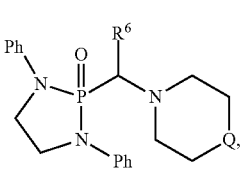

or a salt thereof.

In a further aspect, the compound has a structure represented by a formula selected from:

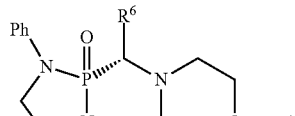
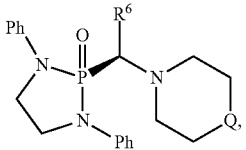

or a salt thereof.

In a further aspect, the compound has a structure represented by a formula:

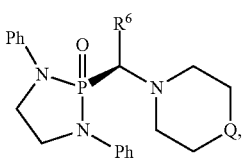

or a salt thereof.

In a further aspect, the compound has a structure represented by a formula:

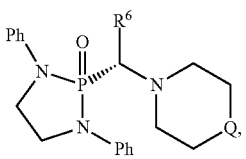

or a salt thereof.

In a further aspect, the compound has a structure represented by a formula:

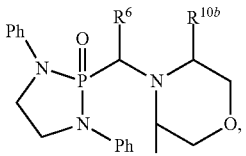

or a salt thereof.

In a further aspect, the compound has a structure represented by a formula selected from:

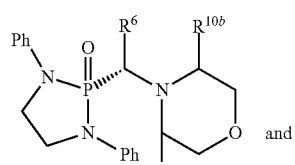

-continued

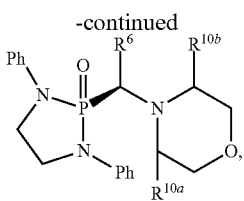

or a salt thereof.

In a further aspect, the compound has a structure represented by a formula:

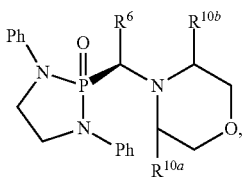

or a salt thereof.

In a further aspect, the compound has a structure represented by a formula:

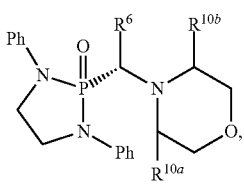

or a salt thereof.

In a further aspect, the compound has a structure represented by a formula:

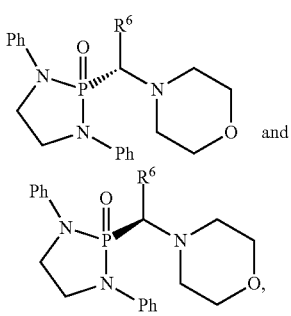

or a salt thereof.

In a further aspect, the compound has a structure represented by a formula:

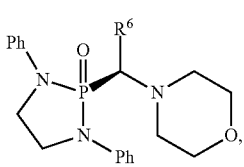

or a salt thereof.

In a further aspect, the compound has a structure represented by a formula:

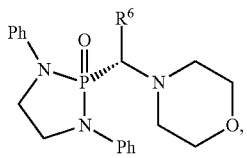

or a salt thereof.

a. Q Groups

In one aspect, Q is selected from O, S, C=O, S=O, SO$_2$, and NR$^1$. In a further aspect, Q is selected from O, S, C=O, S=O, and SO$_2$. In a still further aspect, Q is selected from O, S, C=O, and S=O. In yet a further aspect, Q is selected from O, S, and C=O. In an even further aspect, Q is selected from O and S. In a still further aspect, Q is NR$^1$. In yet a further aspect, Q is SO$_2$. In an even further aspect, Q is S=O. In a still further aspect, Q is C=O. In yet a further aspect, Q is S. In an even further aspect, Q is O.

b. X$^A$ and X$^B$ Groups

In one aspect, each of X$^A$ and X$^B$ is independently selected from NR$^1$, O, and S. In a further aspect, each of X$^A$ and X$^B$ is independently selected from NR$^1$ and O. In a still further aspect, each of X$^A$ and X$^B$ is independently selected from NR$^1$ and S. In yet a further aspect, each of X$^A$ and X$^B$ is independently selected from O and S. In an even further aspect, each of X$^A$ and X$^B$ is NR$^1$. In a still further aspect, each of X$^A$ and X$^B$ is O. In yet a further aspect, each of X$^A$ and X$^B$ is S.

c. R$^1$ Groups

In one aspect, each occurrence of R$^1$, when present, independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups. In a further aspect, each occurrence of R$^1$, when present, is independently selected from hydrogen, C1-C3 alkyl, C1-C3 haloalkyl, C2-C4 alkenyl, C2-C4 alkynyl, C3-C8 cycloalkyl, 4-8 membered heterocycloalkyl, C6-C8 aryl, —(C1-C3 alkyl)(C6-C8 aryl), and 4-8 membered heteroaryl, and wherein each occurrence of R$^1$, when present, is independently substituted with 0, 1, 2, 3, or 4 independently selected R$^5$ groups. In a still further aspect, each occurrence of R$^1$ is H.

In a further aspect, each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, or 3 independently selected R$^5$ groups. In a still further aspect, each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, or 2 independently selected R$^5$ groups. In yet a further aspect, each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$, when present, is independently substituted with 0 or 1 $R^5$ group. In an even further aspect, each occurrence of $R^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R', when present, is independently monosubstituted with a $R^5$ group. In a still further aspect, each occurrence of $R^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$, when present, is unsubstituted.

In a further aspect, each occurrence of $R^1$, when present, is C6-C10 aryl substituted with 0, 1, 2, 3, or 4 independently selected $R^5$ groups. In a still further aspect, each occurrence of $R^1$, when present, is C6-C10 aryl substituted with 0, 1, 2, or 3 independently selected $R^5$ groups. In yet a further aspect, each occurrence of $R^1$, when present, is C6-C10 aryl substituted with 0, 1, or 2 independently selected $R^5$ groups. In an even further aspect, each occurrence of $R^1$, when present, is C6-C10 aryl substituted with 0 or 1 $R^5$ groups. In a still further aspect, each occurrence of R', when present, is C6-C10 aryl monosubstituted with a $R^5$ groups. In yet a further aspect, each occurrence of $R^1$, when present, is unsubstituted C6-C10 aryl.

In a further aspect, each occurrence of $R^1$, when present, is phenyl substituted with 0, 1, 2, 3, or 4 independently selected $R^5$ groups. In a still further aspect, each occurrence of $R^1$, when present, is phenyl substituted with 0, 1, 2, or 3 independently selected $R^5$ groups. In yet a further aspect, each occurrence of $R^1$, when present, is phenyl substituted with 0, 1, or 2 independently selected $R^5$ groups. In an even further aspect, each occurrence of $R^1$, when present, is phenyl substituted with 0 or 1 $R^5$ groups. In a still further aspect, each occurrence of $R^1$, when present, is phenyl monosubstituted with a $R^5$ groups. In yet a further aspect, each occurrence of $R^1$, when present, is unsubstituted phenyl.

In a further aspect, each occurrence of $R^1$, when present, is independently selected from C1-C6 alkyl, C3-C10 cycloalkyl, C6-C10 aryl, and —(C1-C3 alkyl)(C6-C10 aryl). In a still further aspect, each occurrence of $R^1$, when present, is independently selected from C1-C4 alkyl, C3-C8 cycloalkyl, C6-C8 aryl, and —(C1-C3 alkyl)(C6-C8 aryl). In yet a further aspect, each occurrence of $R^1$, when present, is independently selected from methyl, ethyl, n-propyl, i-propyl, cyclohexyl, phenyl, and benzyl. In a still further aspect, each occurrence of $R^1$, when present, is independently selected from methyl, ethyl, cyclohexyl, phenyl and benzyl. In yet a further aspect, each occurrence of $R^1$, when present, is independently selected from methyl, cyclohexyl, phenyl, and benzyl. In an even further aspect, each occurrence of $R^1$, when present, is independently selected from cyclohexyl, phenyl, and benzyl. In a still further aspect, each occurrence of $R^1$, when present, is cyclohexyl. In yet a further aspect, each occurrence of $R^1$, when present, is phenyl. In an even further aspect, each occurrence of $R^1$, when present, is benzyl.

In a further aspect, each occurrence of $R^1$, when present, is independently selected from hydrogen, C1-C6 alkyl, and C6-C10 aryl. In a still further aspect, each occurrence of $R^1$, when present, is independently selected from hydrogen, C1-C4 alkyl, and C6-C8 aryl. In yet a further aspect, each occurrence of $R^1$, when present, is independently selected from hydrogen, methyl, ethyl, n-propyl, i-propyl, and phenyl. In an even further aspect, each occurrence of $R^1$, when present, is independently selected from hydrogen, methyl, ethyl, and phenyl. In a still further aspect, each occurrence of $R^1$, when present, is independently selected from hydrogen, methyl and phenyl.

In a further aspect, each occurrence of $R^1$, when present, is independently selected from C1-C6 alkyl and C6-C10 aryl. In a still further aspect, each occurrence of $R^1$, when present, is independently selected from C1-C4 alkyl and C6-C8 aryl. In yet a further aspect, each occurrence of when present, is independently selected from methyl, ethyl, n-propyl, i-propyl, and phenyl. In an even further aspect, each occurrence of when present, is independently selected from methyl, ethyl, and phenyl. In a still further aspect, each occurrence of when present, is independently selected from ethyl and phenyl. In yet a further aspect, each occurrence of when present, is independently selected from methyl and phenyl.

In a further aspect, each occurrence of $R^1$, when present, is independently selected from hydrogen and C1-C6 alkyl. In a still further aspect, each occurrence of when present, is independently selected from hydrogen, methyl, ethyl, n-propyl, i-propyl, n-butyl, butyl, s-butyl, and t-butyl. In yet a further aspect, each occurrence of when present, is independently selected from hydrogen, methyl, ethyl, n-propyl, and i-propyl. In an even further aspect, each occurrence of when present, is independently selected from hydrogen, methyl, and ethyl. In a still further aspect, each occurrence of $R^1$, when present, is independently selected from hydrogen and ethyl. In yet a further aspect, each occurrence of $R^1$ when present, is independently selected from hydrogen and methyl.

In a further aspect, each occurrence of $R^1$, when present, is independently C1-C6 alkyl. In a still further aspect, each occurrence of $R^1$, when present, is independently selected from methyl, ethyl, n-propyl, i-propyl, n-butyl, i-butyl, s-butyl, and t-butyl. In yet a further aspect, each occurrence of $R^1$, when present, is independently selected from methyl, ethyl, n-propyl, and i-propyl. In an even further aspect, each occurrence of when present, is independently selected from methyl and ethyl. In a still further aspect, each occurrence of $R^1$ when present, is ethyl. In yet a further aspect, each occurrence of when present, is methyl.

d. $R^5$ Groups

In one aspect, each occurrence of $R^5$, when present, is independently selected from halogen, —$NO_2$, —CN, —OH, —SH, —$NH_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O)(C1-C3 alkyl), —(S=O)(C1-C3 alkyl), —$SO_2$(C1-C3 alkyl), —$CO_2R^{11}$, —(C=O)$NR^{12a}R^{12b}$, —$SO_2NR^{12a}R^{12b}$, —O(C=O)$NR^{12a}R^{12b}$, —$NHSO_2NR^{12a}R^{12b}$, and —NH(C=O)$NR^{12a}R^{12b}$.

In a further aspect, each occurrence of $R^5$, when present, is independently selected from —F, —Cl, —$NO_2$, —CN, —OH, —SH, —$NH_2$, methyl, ethyl, propyl, ethenyl, propenyl, ethynyl, propynyl, —$CH_2F$, —$CHF_2$, —$CF_3$, —$CH_2CH_2F$, —$CH_2Cl$, —$CHCl_2$, —$CCl_3$, —$CH_2CH_2Cl$, —$CH_2CN$, —$CH_2CH_2CN$, —$CH_2OH$, —$CH_2CH_2OH$, —$OCH_2F$, —$OCHF_2$, —$OCF_3$, —$OCH_3$, —$OCH_2CH_3$, —$SCH_3$, —$SCH_2CH_3$, —$CH_2OCH_3$, —CH$_2$CH$_2$OCH$_2$CH$_3$, —NHCH$_3$, —NHCH$_2$CH$_3$, —N(CH$_3$)$_2$, —NH(CH$_2$CH$_3$)$_2$, cyclopropyl, cyclobutyl, cyclopentyl, optionally substituted phenyl, —(C═O)CH$_3$, —(C═O)CH$_2$CH$_3$, —(S═O)CH$_3$, —(S═O)CH$_2$CH$_3$, —SO$_2$CH$_3$, —SO$_2$CH$_2$CH$_3$, —CO$_2$CH$_3$, —CO$_2$CH$_2$CH$_3$, —(C═O)NH$_2$, —(C═O)NHCH$_3$, —(C═O)N(CH$_3$)$_2$, —SO$_2$NH$_2$, —SO$_2$NHCH$_3$, —SO$_2$N(CH$_3$)$_2$, —O(C═O)NH$_2$, —O(C═O)NHCH$_3$, —O(C═O)N(CH$_3$)$_2$, —NHSO$_2$NH$_2$, —NHSO$_2$NHCH$_3$, —NHSO$_2$N(CH$_3$)$_2$, —NH(C═O)NH$_2$, —NH(C═O)NHCH$_3$, and —NH(C═O)N(CH$_3$)$_2$. In a still further aspect, each occurrence of R$^5$, when present, is independently selected from —F, —NO$_2$, —CN, —OH, —SH, —NH$_2$, methyl, ethyl, ethenyl, ethynyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —NHCH$_3$, —N(CH$_3$)$_2$, cyclopropyl, cyclobutyl, optionally substituted phenyl, —(C═O)CH$_3$, —(S═O)CH$_3$, —SO$_2$CH$_3$, —CO$_2$CH$_3$, —(C═O)NH$_2$, —(C═O)NHCH$_3$, —(C═O)N(CH$_3$)$_2$, —SO$_2$NH$_2$, —SO$_2$NHCH$_3$, —SO$_2$N(CH$_3$)$_2$, —O(C═O)NH$_2$, —O(C═O)NHCH$_3$, —O(C═O)N(CH$_3$)$_2$, —NHSO$_2$NH$_2$, —NHSO$_2$NHCH$_3$, —NHSO$_2$N(CH$_3$)$_2$, —NH(C═O)NH$_2$, —NH(C═O)NHCH$_3$, and —NH(C═O)N(CH$_3$)$_2$. In yet a further aspect, each occurrence of R$^5$, when present, is independently selected from —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —NHCH$_3$, —N(CH$_3$)$_2$, cyclopropyl, optionally substituted phenyl, —(C═O)CH$_3$, —(S═O)CH$_3$, —SO$_2$CH$_3$, —CO$_2$CH$_3$, —(C═O)NH$_2$, —(C═O)NHCH$_3$, —(C═O)N(CH$_3$)$_2$, —SO$_2$NH$_2$, —SO$_2$NHCH$_3$, —SO$_2$N(CH$_3$)$_2$, —O(C═O)NH$_2$, —O(C═O)NHCH$_3$, —O(C═O)N(CH$_3$)$_2$, —NHSO$_2$NH$_2$, —NHSO$_2$NHCH$_3$, —NHSO$_2$N(CH$_3$)$_2$, —NH(C═O)NH$_2$, —NH(C═O)NHCH$_3$, and —NH(C═O)N(CH$_3$)$_2$.

In a further aspect, each occurrence of R$^5$, when present, is optionally substituted C6-C10 aryl. In a still further aspect, each occurrence of R$^5$, when present, is C6-C10 aryl substituted with 0, 1, 2, or 3 groups independently selected from halogen, —NO$_2$, —CN, —OH, —SH, —NH$_2$, and C1-C4 alkyl. In yet a further aspect, each occurrence of R$^5$, when present, is C6-C10 aryl substituted with 0, 1, or 2 groups independently selected from halogen, —NO$_2$, —CN, —OH, —SH, —NH$_2$, and C1-C4 alkyl. In a still further aspect, each occurrence of R$^5$, when present, is C6-C10 aryl substituted with 0 or 1 group selected from halogen, —NO$_2$, —CN, —OH, —SH, —NH$_2$, and C1-C4 alkyl. In yet a further aspect, each occurrence of R$^5$, when present, is C6-C10 aryl monosubstituted with a group selected from halogen, —NO$_2$, —CN, —OH, —SH, —NH$_2$, and C1-C4 alkyl. In an even further aspect, each occurrence of R$^5$, when present, is unsubstituted C6-C10 aryl.

In a further aspect, each occurrence of R$^5$, when present, is optionally substituted phenyl. In a still further aspect, each occurrence of R$^5$, when present, is phenyl substituted with 0, 1, 2, or 3 groups independently selected from halogen, —NO$_2$, —CN, —OH, —SH, —NH$_2$, and C1-C4 alkyl. In yet a further aspect, each occurrence of R$^5$, when present, is phenyl substituted with 0, 1, or 2 groups independently selected from halogen, —NO$_2$, —CN, —OH, —SH, —NH$_2$, and C1-C4 alkyl. In a still further aspect, each occurrence of R$^5$, when present, is phenyl substituted with 0 or 1 group selected from halogen, —NO$_2$, —CN, —OH, —SH, —NH$_2$, and C1-C4 alkyl. In yet a further aspect, each occurrence of R$^5$, when present, is phenyl monosubstituted with a group selected from —NO$_2$, —CN, —OH, —SH, —NH$_2$, and C1-C4 alkyl. In an even further aspect, each occurrence of R$^5$, when present, is unsubstituted phenyl.

In a further aspect, each occurrence of R$^5$, when present, is independently selected from halogen, —NO$_2$, —CN, —OH, —SH, —NH$_2$, C1-C4 alkyl, C1-C3 haloalkyl, C1-C3 alkoxy, C1-C3 thioalkyl, C1-C3 alkyl(C1-C3 alkoxy), C1-C3 alkylamino, and (C1-C3)(C1-C3) dialkylamino. In a further aspect, each occurrence of R$^5$, when present, is independently selected from —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, —OCH$_2$CH$_3$, —SCH$_3$, —SCH$_2$CH$_3$, —CH$_2$OCH$_3$, —CH$_2$CH$_2$OCH$_2$CH$_3$, —NHCH$_3$, —NHCH$_2$CH$_3$, —N(CH$_3$)$_2$, and —NH(CH$_2$CH$_3$)$_2$. In a still further aspect, each occurrence of R$^5$, when present, is independently selected from —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$. In yet a further aspect, each occurrence of R$^5$, when present, is independently selected from —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$.

In a further aspect, each occurrence of R$^5$, when present, is independently selected from halogen, —NO$_2$, —CN, —OH, —SH, —NH$_2$, C1-C4 alkyl, C1-C3 haloalkyl, and C1-C3 alkoxy. In a further aspect, each occurrence of R$^5$, when present, is independently selected from —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each occurrence of R$^5$, when present, is independently selected from —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, and —OCH$_3$. In yet a further aspect, each occurrence of R$^5$, when present, is independently selected from —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, and —OCH$_3$.

In a further aspect, each occurrence of R$^5$, when present, is independently selected from C1-C4 alkyl, C1-C3 haloalkyl, and C1-C3 alkoxy. In a further aspect, each occurrence of R$^5$, when present, is independently selected from methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each occurrence of R$^5$, when present, is independently selected from methyl, ethyl, —CH$_2$F, —CHF$_2$, —CF$_3$, —CH$_2$Cl, —CHCl$_2$, —CCl$_3$, and —OCH$_3$. In yet a further aspect, each occurrence of R$^5$, when present, is independently selected from methyl, —CH$_2$F, —CHF$_2$, —CF$_3$, —CH$_2$Cl, —CHCl$_2$, —CCl$_3$, and —OCH$_3$.

In a further aspect, each occurrence of R$^5$, when present, is independently selected from C1-C4 alkyl and C1-C3 alkoxy. In a further aspect, each occurrence of R$^5$, when present, is independently selected from methyl, ethyl, propyl, —OCH$_3$, and —OCH$_2$CH$_3$. In a still further aspect, each occurrence of R$^5$, when present, is independently selected from methyl, ethyl, and —OCH$_3$. In yet a further aspect, each occurrence of R$^5$, when present, is independently selected from methyl and —OCH$_3$.

In a further aspect, each occurrence of R$^5$, when present, is C1-C3 haloalkyl. In a further aspect, each occurrence of R$^5$, when present, is independently selected from —CH$_2$F, —CHF$_2$, —CF$_3$, —CH$_2$CH$_2$F, —CH$_2$Cl, —CHCl$_2$, —CCl$_3$, and —CH$_2$CH$_2$Cl. In a still further aspect, each occurrence of R$^5$, when present, is independently selected from —CH$_2$F, —CHF$_2$, —CF$_3$, —CH$_2$Cl, —CHCl$_2$, and —CCl$_3$. In yet a further aspect, each occurrence of R$^5$, when present, is independently selected from —CHF$_2$, —CF$_3$, —CHCl$_2$, and —CCl$_3$. In an even further aspect, each occurrence of R$^5$, when present, is independently selected from —CF$_3$ and —CCl$_3$. In a still further aspect, each occurrence of R$^5$, when present, is —CF$_3$. In yet a further aspect, each occurrence of R$^5$, when present, is —CCl$_3$.

In a further aspect, each occurrence of R$^5$, when present, is independently selected from —OCH$_3$, —OCH$_2$CH$_3$, —OCH$_2$CH$_2$CH$_3$, and —OCH(CH$_3$)$_2$. In a still further aspect, each occurrence of R$^5$, when present, is independently selected from —OCH$_3$ and —OCH$_2$CH$_3$. In yet a further aspect, each occurrence of R$^5$, when present, is —OCH$_2$CH$_2$CH$_3$. In an even further aspect, each occurrence of R$^5$, when present, is —OCH(CH$_3$)$_2$. In a still further aspect, each occurrence of R$^5$, when present, is —OCH$_2$CH$_3$. In yet a further aspect, each occurrence of R$^5$, when present, is —OCH$_3$.

In a further aspect, each occurrence of R$^5$, when present, is independently selected from methyl, ethyl, n-propyl, i-propyl, n-butyl, i-butyl, s-butyl, and t-butyl. In a still further aspect, each occurrence of R$^5$, when present, is independently selected from methyl, ethyl, n-propyl, and i-propyl. In yet a further aspect, R$^5$, when present, is independently selected from methyl and ethyl. In an even further aspect, each occurrence of R$^5$, when present, is ethyl. In a still further aspect, each occurrence of R$^5$, when present, is methyl.

e. R$^{11}$ Groups

In one aspect, each occurrence of R$^{11}$, when present, is independently selected from hydrogen and C1-C4 alkyl. In a further aspect, each occurrence of R$^{11}$, when present, is independently selected from hydrogen, methyl, ethyl, n-propyl, and i-propyl. In a still further aspect, each occurrence of R$^{11}$, when present, is independently selected from hydrogen, methyl, and ethyl. In yet a further aspect, each occurrence of R$^{11}$, when present, is independently selected from hydrogen and ethyl. In an even further aspect, each occurrence of R$^{11}$, when present, is independently selected from hydrogen and methyl. In a still further aspect, each occurrence of R$^{11}$, when present, is ethyl. In yet a further aspect, each occurrence of R$^{11}$, when present, is methyl. In an even further aspect, each occurrence of R$^{11}$, when present, is hydrogen.

f. R$^{12a}$ and R$^{12b}$ Groups

In one aspect, each occurrence of R$^{12a}$ and R$^{12b}$, when present, is independently selected from hydrogen and C1-C3 alkyl. In a further aspect, each occurrence of R$^{12a}$ and R$^{12b}$, when present, is independently selected from hydrogen, methyl, and ethyl. In a still further aspect, each occurrence of R$^{12a}$ and R$^{12b}$, when present, is independently selected from hydrogen and ethyl. In yet a further aspect, each occurrence of R$^{12a}$ and R$^{12b}$, when present, is independently selected from hydrogen and methyl. In an even further aspect, each occurrence of R$^{12a}$ and R$^{12b}$, when present, is ethyl. In a still further aspect, each occurrence of R$^{12a}$ and R$^{12b}$, when present, is methyl. In yet a further aspect, each occurrence of R$^{12a}$ and R$^{12b}$, when present, is hydrogen.

g. R$^X$ and R$^Y$ Groups

In one aspect, each of R$^X$ and R$^Y$ is independently selected from hydrogen, C1-C8 alkyl, C6-C10 aryloxy, C6-C10 aryl, and 4-10 membered heteroaryl, or wherein each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups. In a further aspect, each of R$^X$ and R$^Y$ is hydrogen.

In a further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups. In a still further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, or 3 independently selected R$^5$ groups. In yet a further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, or 2 independently selected R$^5$ groups. In an even further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0 or 1 R$^5$ groups. In a still further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are monosubstituted with a R$^5$ group. In yet a further aspect, each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are unsubstituted.

In a further aspect, each of R$^X$ and R$^Y$ are optionally covalently bonded together and, together with the intermediate atoms, comprise a 5- to 7-membered cycloalkyl or a 5- to 7-membered heterocycloalkyl and are substituted with 0, 1, 2, 3, or 4 independently selected R$^5$ groups. In a still further aspect, each of R$^X$ and R$_Y$ are optionally covalently bonded together and, together with the intermediate atoms, comprise a 5- to 7-membered cycloalkyl or a 5- to 7-membered heterocycloalkyl and are substituted with 0, 1, 2, or 3 independently selected R$^5$ groups. In yet a further aspect, each of R$^X$ and R$^Y$ are optionally covalently bonded together and, together with the intermediate atoms, comprise a 5- to 7-membered cycloalkyl or a 5- to 7-membered heterocycloalkyl and are substituted with 0, 1, or 2 independently selected R$^5$ groups. In an even further aspect, each of R$^X$ and R$^Y$ are optionally covalently bonded together and, together with the intermediate atoms, comprise a 5- to 7-membered cycloalkyl or a 5- to 7-membered heterocycloalkyl and are substituted with 0 or 1 R$^5$ groups. In a still further aspect, each of R$^X$ and R$^Y$ are optionally covalently bonded together and, together with the intermediate atoms, comprise a 5- to 7-membered cycloalkyl or a 5- to 7-membered heterocycloalkyl and are monosubstituted with a R$^5$ group. In yet a further aspect, each of R$^X$ and R$^Y$ are optionally covalently bonded together and, together with the intermediate atoms, comprise a 5- to 7-membered cycloalkyl or a 5- to 7-membered heterocycloalkyl and are unsubstituted.

In a further aspect, each of R$^X$ and R$^Y$ are optionally covalently bonded together and, together with the intermediate atoms, comprise a 5- to 7-membered cycloalkyl substituted with 0, 1, 2, 3, or 4 independently selected $R^5$ groups. In a still further aspect, each of $R^X$ and $R^Y$ are optionally covalently bonded together and, together with the intermediate atoms, comprise a 5- to 7-membered cycloalkyl substituted with 0, 1, 2, or 3 independently selected $R^5$ groups. In yet a further aspect, each of $R^X$ and $R^Y$ are optionally covalently bonded together and, together with the intermediate atoms, comprise a 5- to 7-membered cycloalkyl substituted with 0, 1, or 2 independently selected $R^5$ groups. In an even further aspect, each of $R^X$ and $R^Y$ are optionally covalently bonded together and, together with the intermediate atoms, comprise a 5- to 7-membered cycloalkyl substituted with 0 or 1 $R^5$ groups. In a still further aspect, each of $R^X$ and $R^Y$ are optionally covalently bonded together and, together with the intermediate atoms, comprise a 5- to 7-membered cycloalkyl monosubstituted with a $R^5$ group. In yet a further aspect, each of $R^X$ and $R^Y$ are optionally covalently bonded together and, together with the intermediate atoms, comprise an unsubstituted 5- to 7-membered cycloalkyl.

In a further aspect, each of $R^X$ and $R^Y$ are optionally covalently bonded together and, together with the intermediate atoms, comprise a cyclohexyl substituted with 0, 1, 2, 3, or 4 independently selected $R^5$ groups. In a still further aspect, each of $R^X$ and $R^Y$ are optionally covalently bonded together and, together with the intermediate atoms, comprise a cyclohexyl substituted with 0, 1, 2, or 3 independently selected $R^5$ groups. In yet a further aspect, each of $R^X$ and $R^Y$ are optionally covalently bonded together and, together with the intermediate atoms, comprise a cyclohexyl substituted with 0, 1, or 2 independently selected $R^5$ groups. In an even further aspect, each of $R^X$ and $R^Y$ are optionally covalently bonded together and, together with the intermediate atoms, comprise a cyclohexyl substituted with 0 or 1 $R^5$ groups. In a still further aspect, each of $R^X$ and $R^Y$ are optionally covalently bonded together and, together with the intermediate atoms, comprise a cyclohexyl monosubstituted with a $R^5$ group. In yet a further aspect, each of $R^X$ and $R^Y$ are optionally covalently bonded together and, together with the intermediate atoms, comprise an unsubstituted cyclohexyl.

In a further aspect, each of $R^X$ and $R^Y$ are optionally covalently bonded together and, together with the intermediate atoms, comprise a 5- to 7-membered aryl or a 5- to 7-membered heteroaryl and are substituted with 0, 1, 2, 3, or 4 independently selected $R^5$ groups. In a still further aspect, each of $R^X$ and $R^Y$ are optionally covalently bonded together and, together with the intermediate atoms, comprise a 5- to 7-membered aryl or a 5- to 7-membered heteroaryl and are substituted with 0, 1, 2, or 3 independently selected $R^5$ groups. In yet a further aspect, each of $R^X$ and $R^Y$ are optionally covalently bonded together and, together with the intermediate atoms, comprise a 5- to 7-membered aryl or a 5- to 7-membered heteroaryl and are substituted with 0, 1, or 2 independently selected $R^5$ groups. In an even further aspect, each of $R^X$ and $R^Y$ are optionally covalently bonded together and, together with the intermediate atoms, comprise a 5- to 7-membered aryl or a 5- to 7-membered heteroaryl and are substituted with 0 or 1 $R^5$ groups. In a still further aspect, each of $R^X$ and $R^Y$ are optionally covalently bonded together and, together with the intermediate atoms, comprise a 5- to 7-membered aryl or a 5- to 7-membered heteroaryl and are monosubstituted with a $R^5$ group. In yet a further aspect, each of $R^X$ and $R^Y$ are optionally covalently bonded together and, together with the intermediate atoms, comprise a 5- to 7-membered aryl or a 5- to 7-membered heteroaryl and are unsubstituted.

In a further aspect, each of $R^X$ and $R^Y$ are optionally covalently bonded together and, together with the intermediate atoms, comprise a 5- to 7-membered aryl substituted with 0, 1, 2, 3, or 4 independently selected $R^5$ groups. In a still further aspect, each of $R^X$ and $R^Y$ are optionally covalently bonded together and, together with the intermediate atoms, comprise a 5- to 7-membered aryl substituted with 0, 1, 2, or 3 independently selected $R^5$ groups. In yet a further aspect, each of $R^X$ and $R^Y$ are optionally covalently bonded together and, together with the intermediate atoms, comprise a 5- to 7-membered aryl substituted with 0, 1, or 2 independently selected $R^5$ groups. In an even further aspect, each of $R^X$ and $R^Y$ are optionally covalently bonded together and, together with the intermediate atoms, comprise a 5- to 7-membered aryl substituted with 0 or 1 $R^5$ groups. In a still further aspect, each of $R^X$ and $R^Y$ are optionally covalently bonded together and, together with the intermediate atoms, comprise a 5- to 7-membered aryl monosubstituted with a $R^5$ group. In yet a further aspect, each of $R^X$ and $R^Y$ are optionally covalently bonded together and, together with the intermediate atoms, comprise an unsubstituted 5- to 7-membered aryl.

In a further aspect, each of $R^X$ and $R^Y$ is independently selected from hydrogen, C1-C8 alkyl, C6-C10 aryloxy, C6-C10 aryl, and 4-10 membered heteroaryl. In a still further aspect, each of $R^X$ and $R^Y$ is independently selected from hydrogen, C1-C4 alkyl, C6-C8 aryloxy, C6-C8 aryl, and 4-8 membered heteroaryl. In yet a further aspect, each of $R^X$ and $R^Y$ is independently selected from hydrogen, —OPh, phenyl, and cyclohexyl. In an even further aspect, each of $R^X$ and $R^Y$ is hydrogen. In a still further aspect, each of $R^X$ and $R^Y$ is phenyl. In yet a further aspect, each of $R^X$ and $R^Y$ is cyclohexyl. In an even further aspect, each of $R^X$ and $R^Y$ is phenyl. In yet a further aspect, each of $R^X$ and $R^Y$ is —OPh.

In a further aspect, each of $R^X$ and $R^Y$ is independently C1-C8 alkyl. In a still further aspect, each of $R^X$ and $R^Y$ is independently C1-C4 alkyl. In yet a further aspect, each of $R^X$ and $R^Y$ is independently selected from methyl, ethyl, n-propyl, and i-propyl. In an even further aspect, each of $R^X$ and $R^Y$ is independently selected from methyl and ethyl. In a still further aspect, each of $R^X$ and $R^Y$ is ethyl. In yet a further aspect, each of $R^X$ and $R^Y$ is methyl.

h. $R^6$ Groups

In one aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups. In a further aspect, each occurrence of $R^1$, when present, is independently selected from hydrogen, C1-C3 alkyl, C1-C3 haloalkyl, C2-C4 alkenyl, C2-C4 alkynyl, C3-C8 cycloalkyl, 4-8 membered heterocycloalkyl, C6-C8 aryl, —(C1-C3 alkyl)(C6-C8 aryl), and 4-8 membered heteroaryl, and substituted with 0, 1, 2, 3, or 4 independently selected $R^5$ groups. In a still further aspect, $R^6$ is H.

In a further aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, or 3 independently selected $R^5$ groups. In a still further aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, or 2 independently selected $R^5$ groups. In yet a further aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0 or 1 $R^5$ group. In an even further aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and monosubstituted with a $R^5$ group. In a still further aspect, $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and unsubstituted.

In a further aspect, $R^6$ is selected from C6-C10 aryl and 4-10 membered heteroaryl and substituted with 0, 1, 2, 3, or 4 independently selected $R^5$ groups. In a still further aspect, $R^6$ is selected from C6-C10 aryl and 4-10 membered heteroaryl and substituted with 0, 1, 2, or 3 independently selected $R^5$ groups. In yet a further aspect, $R^6$ is selected from C6-C10 aryl and 4-10 membered heteroaryl and substituted with 0, 1, or 2 independently selected $R^5$ groups. In an even further aspect, $R^6$ is selected from C6-C10 aryl and 4-10 membered heteroaryl and substituted with 0 or 1 $R^5$ group. In a still further aspect, $R^6$ is selected from C6-C10 aryl and 4-10 membered heteroaryl and unsubstituted.

In a further aspect, $R^6$ is C6-C10 aryl substituted with 0, 1, 2, 3, or 4 independently selected $R^5$ groups. In a still further aspect, $R^6$ is C6-C10 aryl substituted with 0, 1, 2, or 3 independently selected $R^5$ groups. In yet a further aspect, $R^6$ is C6-C10 aryl substituted with 0, 1, or 2 independently selected $R^5$ groups. In an even further aspect, $R^6$ is C6-C10 aryl substituted with 0 or 1 $R^5$ groups. In a still further aspect, $R^6$ is C6-C10 aryl monosubstituted with a $R^5$ groups. In yet a further aspect, $R^6$ is unsubstituted C6-C10 aryl.

In a further aspect, $R^6$ is phenyl substituted with 0, 1, 2, 3, or 4 independently selected $R^5$ groups. In a still further aspect, $R^6$ is phenyl substituted with 0, 1, 2, or 3 independently selected $R^5$ groups. In yet a further aspect, $R^6$ is phenyl substituted with 0, 1, or 2 independently selected $R^5$ groups. In an even further aspect, $R^6$ is phenyl substituted with 0 or 1 $R^5$ groups. In a still further aspect, $R^6$ is phenyl monosubstituted with a $R^5$ groups. In yet a further aspect, $R^6$ is unsubstituted phenyl.

In a further aspect, $R^6$ is selected from C1-C6 alkyl, C3-C10 cycloalkyl, C6-C10 aryl, and —(C1-C3 alkyl)(C6-C10 aryl). In a still further aspect, $R^6$ is selected from C1-C4 alkyl, C3-C8 cycloalkyl, C6-C8 aryl, and —(C1-C3 alkyl)(C6-C8 aryl). In yet a further aspect, $R^6$ is selected from methyl, ethyl, n-propyl, i-propyl, cyclohexyl, phenyl, and benzyl. In a still further aspect, $R^6$ is selected from methyl, ethyl, cyclohexyl, phenyl and benzyl. In yet a further aspect, $R^6$ is selected from methyl, cyclohexyl, phenyl, and benzyl. In an even further aspect, $R^6$ is selected from cyclohexyl, phenyl, and benzyl. In a still further aspect, $R^6$ is cyclohexyl. In yet a further aspect, $R^6$ is phenyl. In an even further aspect, $R^6$ is benzyl.

In a further aspect, $R^6$ is selected from hydrogen, C1-C6 alkyl, and C6-C10 aryl. In a still further aspect, $R^6$ is selected from hydrogen, C1-C4 alkyl, and C6-C8 aryl. In yet a further aspect, $R^6$ is selected from hydrogen, methyl, ethyl, n-propyl, i-propyl, and phenyl. In an even further aspect, $R^6$ is selected from hydrogen, methyl, ethyl, and phenyl. In a still further aspect, $R^6$ is selected from hydrogen, methyl and phenyl.

In a further aspect, $R^6$ is selected from C1-C6 alkyl and C6-C10 aryl. In a still further aspect, $R^6$ is selected from C1-C4 alkyl and C6-C8 aryl. In yet a further aspect, $R^6$ is selected from methyl, ethyl, n-propyl, i-propyl, and phenyl. In an even further aspect, $R^6$ is selected from methyl, ethyl, and phenyl. In a still further aspect, $R^6$ is selected from ethyl and phenyl. In yet a further aspect, $R^6$ is selected from methyl and phenyl.

In a further aspect, $R^6$ is selected from hydrogen and C1-C6 alkyl. In a still further aspect, $R^6$ is selected from hydrogen, methyl, ethyl, n-propyl, i-propyl, n-butyl, butyl, s-butyl, and t-butyl. In yet a further aspect, $R^6$ is selected from hydrogen, methyl, ethyl, n-propyl, and i-propyl. In an even further aspect, $R^6$ is selected from hydrogen, methyl, and ethyl. In a still further aspect, $R^6$ is selected from hydrogen and ethyl. In yet a further aspect, $R^6$ is selected from hydrogen and methyl.

In a further aspect, $R^6$ is C1-C6 alkyl. In a still further aspect, $R^6$ is selected from methyl, ethyl, n-propyl, i-propyl, n-butyl, i-butyl, s-butyl, and t-butyl. In yet a further aspect, $R^6$ is selected from methyl, ethyl, n-propyl, and i-propyl. In an even further aspect, $R^6$ is selected from methyl and ethyl. In a still further aspect, $R^6$ is ethyl. In yet a further aspect, $R^6$ is methyl.

i. $R^{10A}$ and $R^{10B}$ Groups

In one aspect, each of $R^{10a}$ and $R^{10b}$ is independently selected from hydrogen and C1-C4 alkyl. In a further aspect, each of $R^{10a}$ and $R^{10b}$ is hydrogen.

In a further aspect, each of $R^{10a}$ and $R^{10b}$ is independently selected from hydrogen, methyl, ethyl, n-propyl, i-propyl, n-butyl, i-butyl, s-butyl, and t-butyl. In a still further aspect, each of $R^{10a}$ and $R^{10b}$ is independently selected from hydrogen, methyl, ethyl, n-propyl, and i-propyl. In yet a further aspect, each of $R^{10a}$ and $R^{10b}$ is independently selected from hydrogen, methyl, and ethyl. In an even further aspect, each of $R^{10a}$ and $R^{10b}$ is independently selected from hydrogen and ethyl. In a still further aspect, each of $R^{10a}$ and $R^{10b}$ is independently selected from hydrogen and methyl.

In a further aspect, each of $R^{10a}$ and $R^{10b}$ is independently selected from methyl, ethyl, n-propyl, i-propyl, n-butyl, i-butyl, s-butyl, and t-butyl. In a still further aspect, each of $R^{10a}$ and $R^{10b}$ is independently selected from methyl, ethyl, n-propyl, and i-propyl. In yet a further aspect, each of $R^{10a}$ and $R^{10b}$ is independently selected from methyl, and ethyl. In an even further aspect, each of $R^{10a}$ and $R^{10b}$ is ethyl. In a still further aspect, each of $R^{10a}$ and $R^{10b}$ is methyl.

2. α-Aminophosphonates Examples

In one aspect, a compound is selected from:

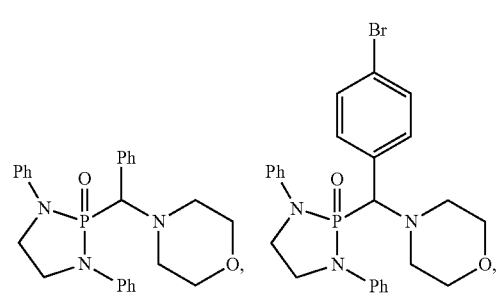

-continued
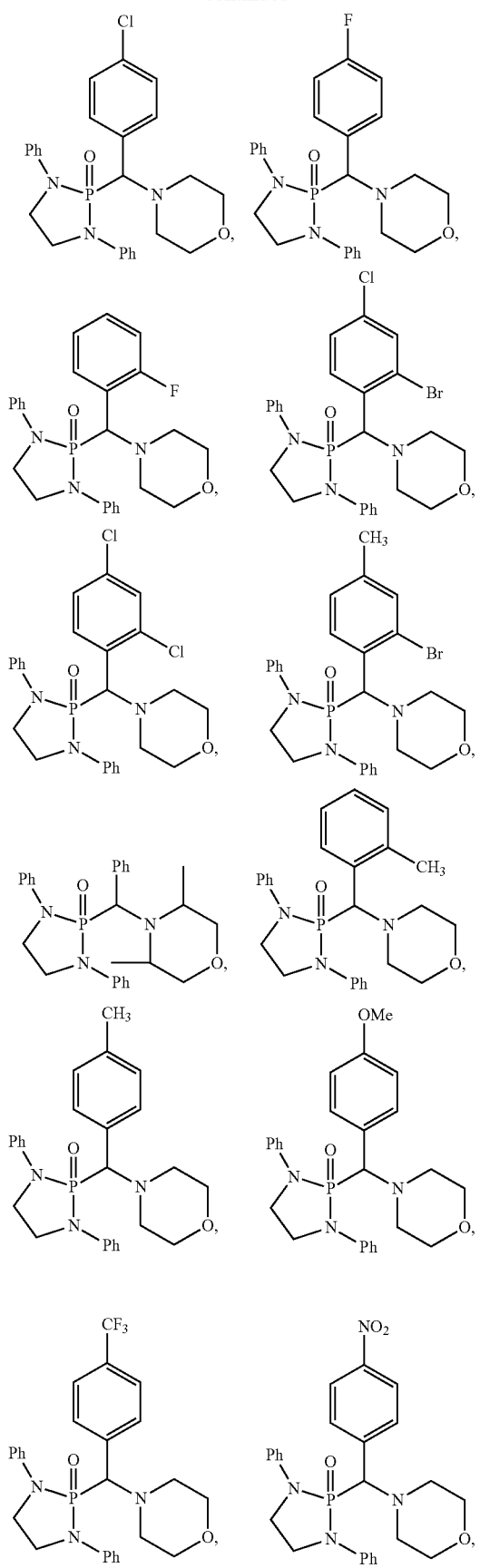
-continued
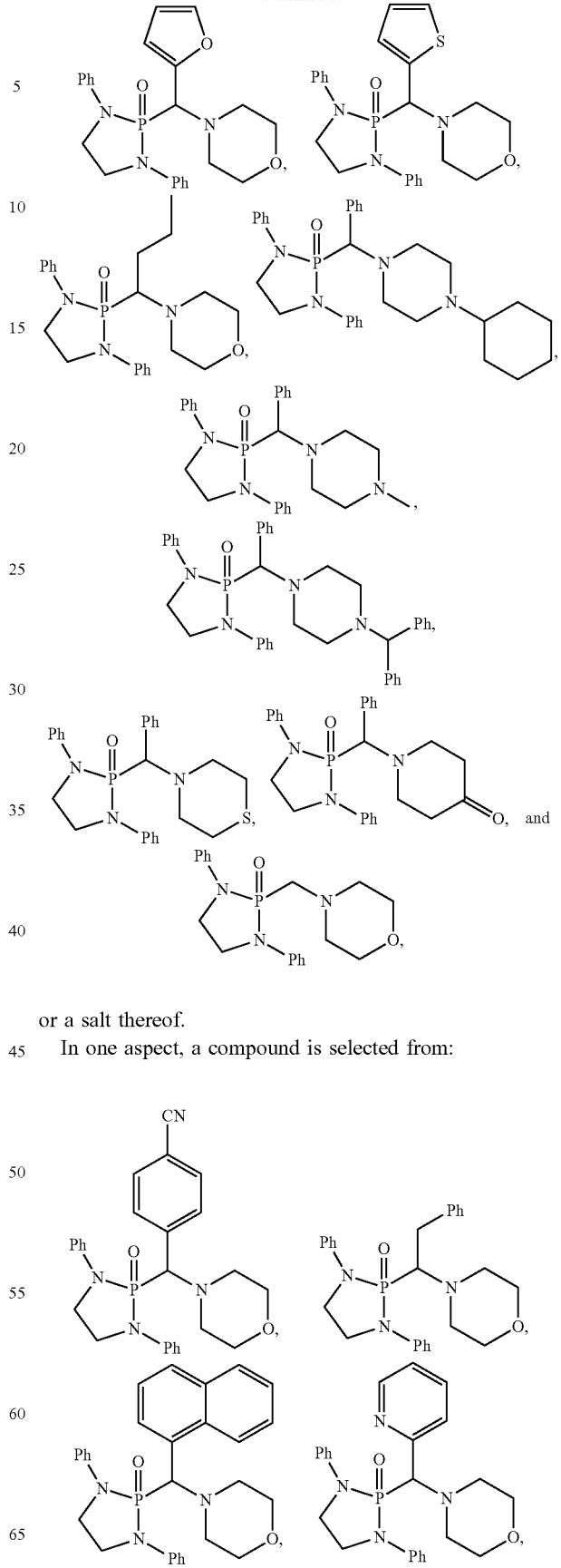
or a salt thereof.
In one aspect, a compound is selected from:

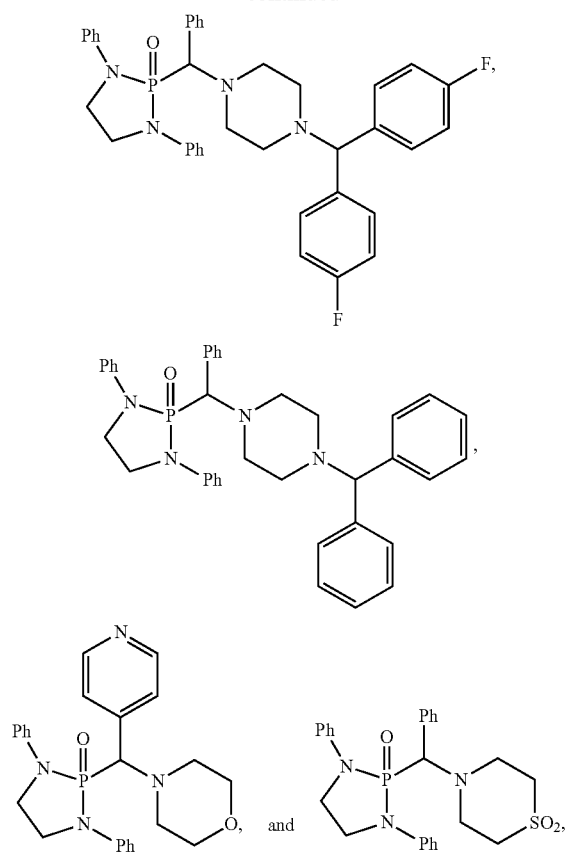
or a salt thereof.
3. Prophetic Compound Examples
The following compound examples are prophetic, and can be prepared using the synthesis methods described herein above and other general methods as needed as would be known to one skilled in the art. Thus, in one aspect, a compound can be selected from:
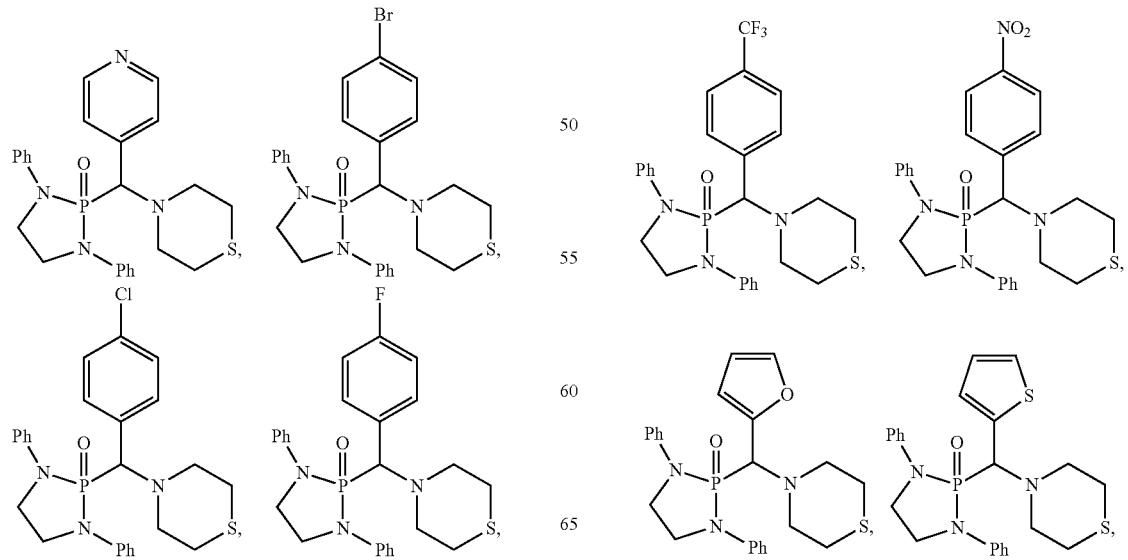

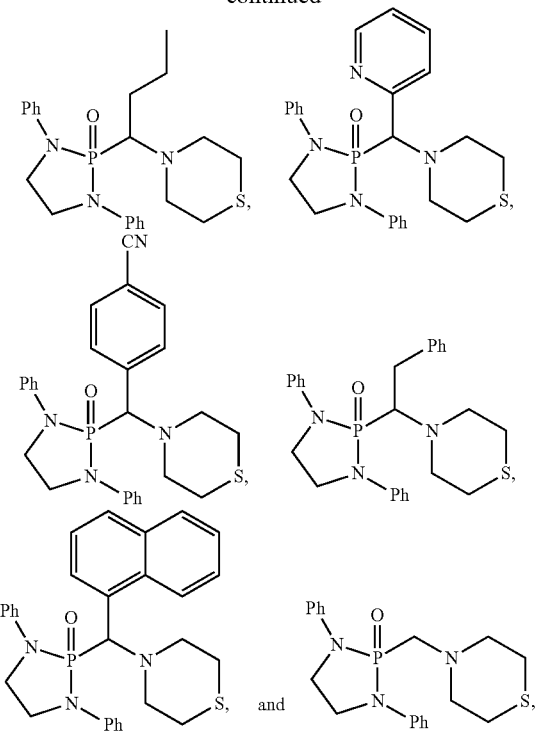
or a derivative thereof.
In one aspect, a compound can be selected from:
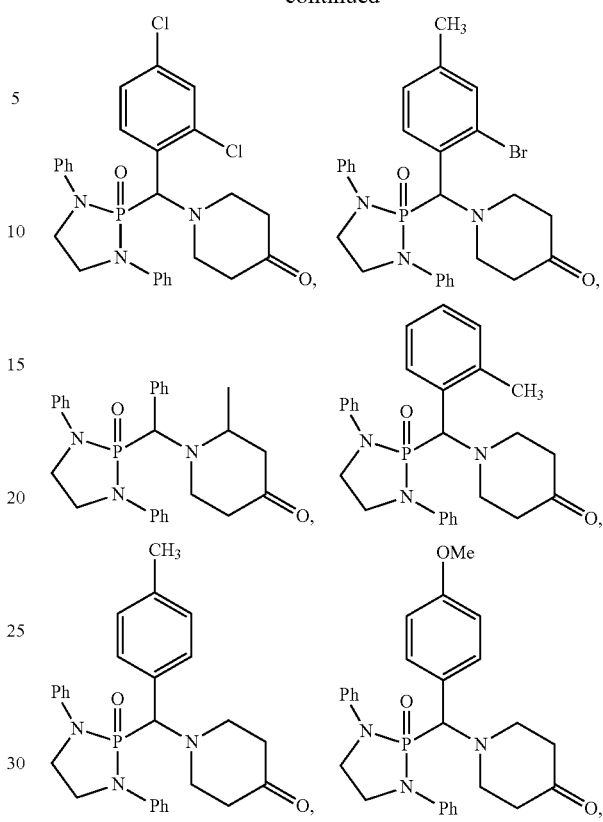
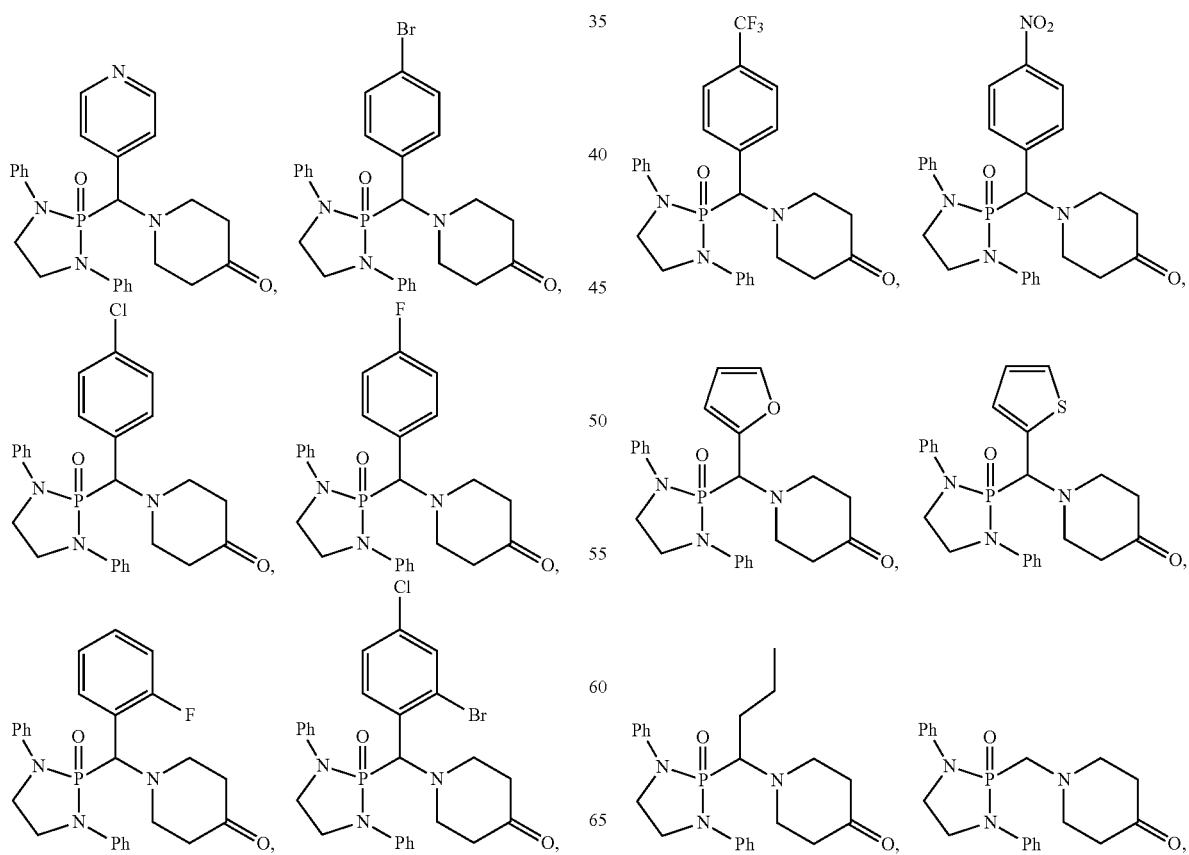

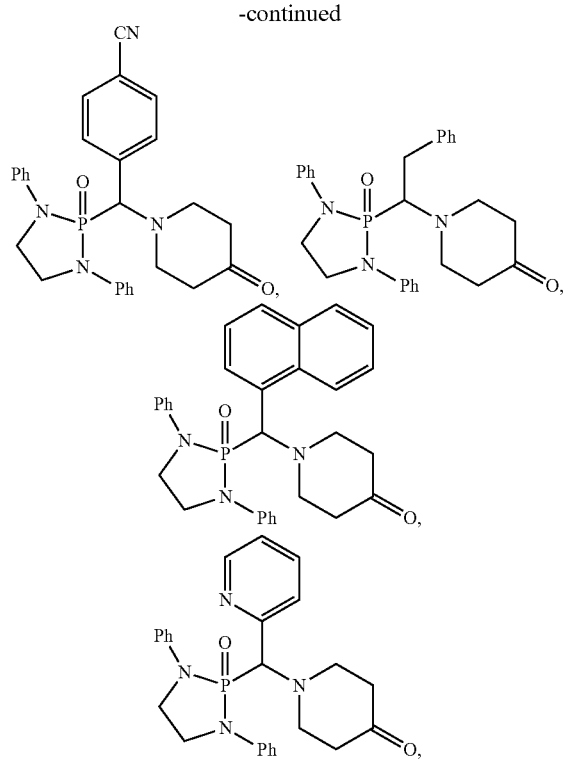
or a derivative thereof.
In one aspect, a compound can be selected from:
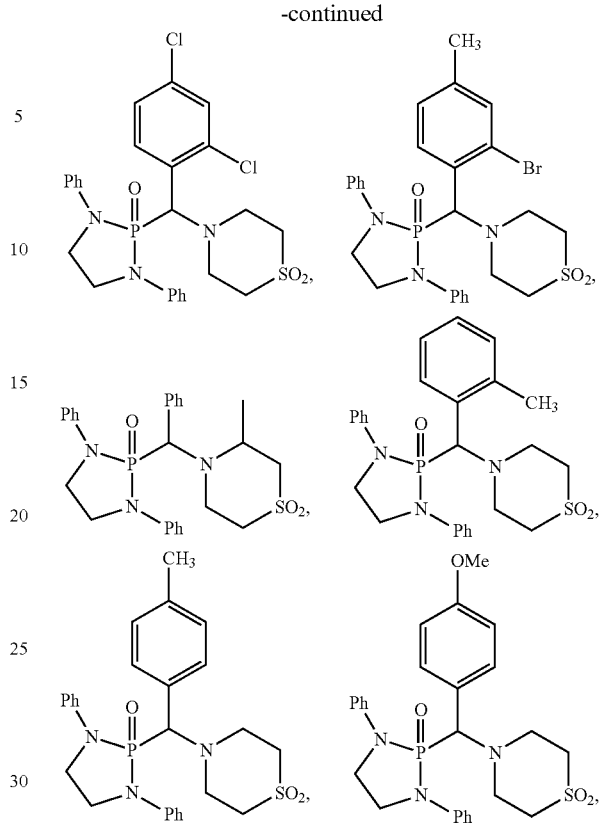
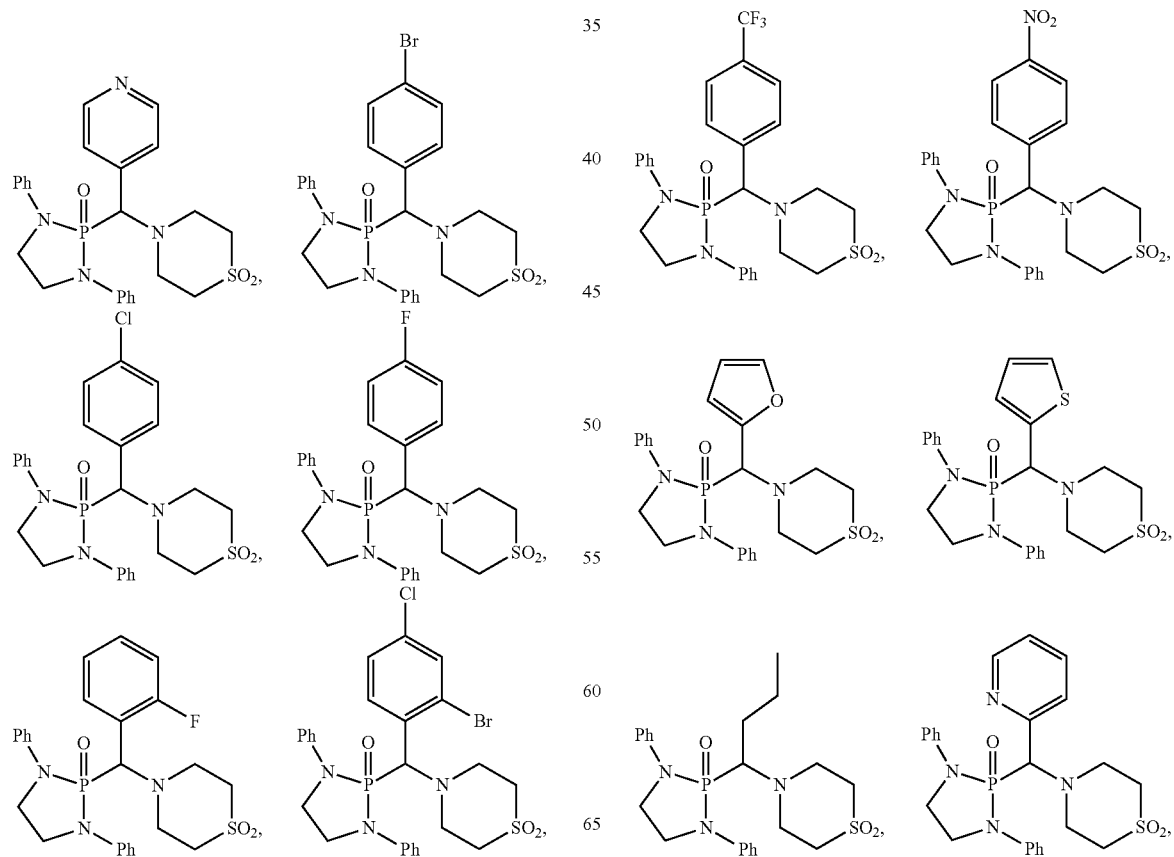

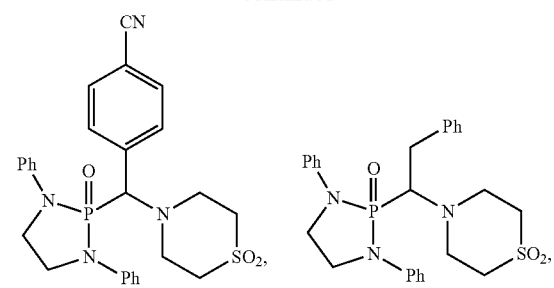

or a derivative thereof.

In one aspect, a compound can be selected from:

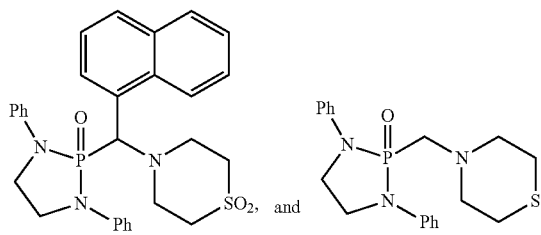

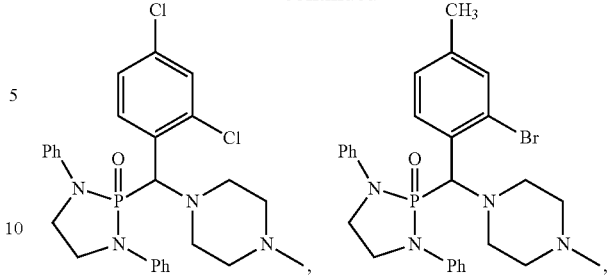

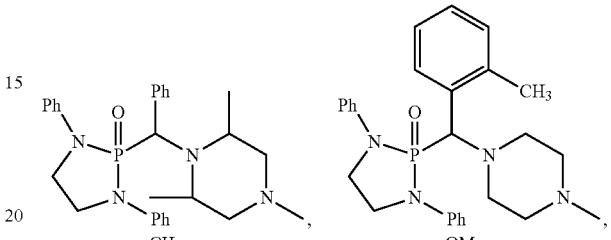

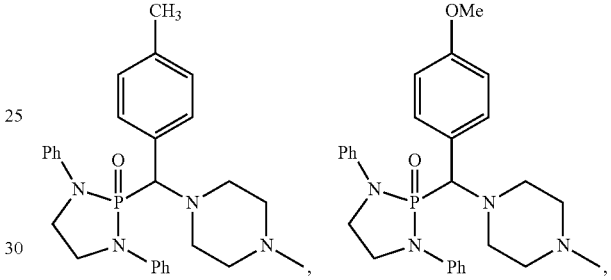

or a derivative thereof.

C. N-HETEROCYCLIC PHOSPHINE REAGENTS

In one aspect, the invention relates to compounds useful in C—C and C—P bond-forming techniques. More specifically, in one aspect, the present invention relates to compounds useful in chemical reactions including, but not limited to, hydroformylations, Heck reactions, cross-coupling reactions, allylic substitutions, Pudovik-type reactions, Michael-type reactions, Michaelis-Arbuzov reactions, and Mannich-Arbuzov reactions. The present invention further relates to compounds useful in the preparation of vinylphosphonates.

The disclosed N-heterocyclic phosphines (NHPs) are useful in, for example, generating phosphorus-carbon bonds under metal-free reaction conditions. As provided herein, one application of NHPs in organic synthesis is the formation of α-aminophosphonates. In various aspects, the reaction of an appropriately substituted aldehyde, an appropriately substituted amine, and an NHP compound can promote a Manich Arbuzov cascade reaction to generate α-aminophosphonates. A further application of NHPs in organic synthesis is the formation of β-aminophosphonates. In various aspects, the reaction of an appropriately substituted heterocycloalkane and an NHP compound can promote a ring-opening reaction to generate β-aminophosphonates. Forming phosphorus-carbon bonds under metal-free reaction conditions is also useful in, for example, polymer synthesis, where metal impurities may impart undesirable material or thermal properties. Organophosphorus compounds (i.e., compounds having a P—C bond) are also useful, for example, as fire retardants and insecticides, and the production of these compounds via metal-free reactions is desirable.

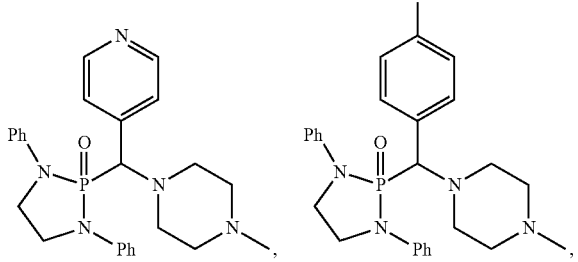

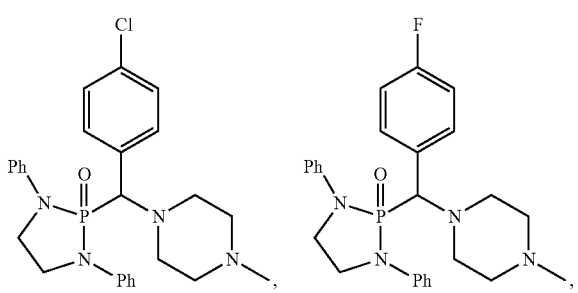

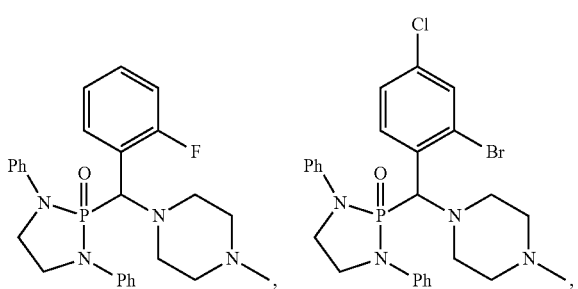

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

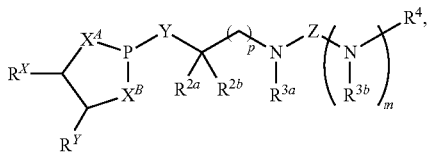

wherein m is selected from 0 and 1; wherein p is selected from 0, 1, 2, 3, 4, and 5; wherein Y is selected from $CH_2$, $CH(CH_3)$, O, and S; wherein each of $X^A$ and $X^B$ is independently selected from $NR^1$, O, and S; wherein each occurrence of $R^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$, when present, is independently substituted with 0, 1, 2, 3, or 4 independently selected $R^5$ groups; wherein each occurrence of $R^5$, when present, is independently selected from halogen, —$NO_2$, —CN, —OH, —SH, —$NH_2$, C1-C3 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl (C1-C3 alkoxy), C1-C3 alkylamino, (C1-C3)(C1-C3) dialkylamino, C3-C7 cycloalkyl, C6-C10 aryl, —(C=O)(C1-C3 alkyl), —(S=O)(C1-C3 alkyl), —$SO_2$(C1-C3 alkyl), —$CO_2R^{11}$, —(C=O)$NR^{12a}R^{12b}$, —$SO_2NR^{12a}R^{12b}$, —O(C=O)$NR^{12a}R^{12b}$, —$NHSO_2NR^{12a}R^{12b}$, and —NR(C=O)$NR^{12a}R^{12b}$; wherein each occurrence of $R^{11}$, when present, is independently selected from hydrogen and C1-C4 alkyl; wherein each occurrence of $R^{12a}$ and $R^{12b}$, when present, is independently selected from hydrogen and C1-C3 alkyl; wherein Z is selected from C=O, C=S, S=O, $SO_2$, and a structure represented by a formula:

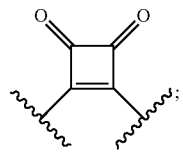 [SMILES: *c1c(*)c(=O)c1=O]

wherein each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups; wherein each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0, 1, 2, 3, or 4 independently selected $R^5$ groups; and wherein $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, and 4-10 membered heteroaryl, and —(C1-C3 alkyl)(C6-C10 aryl), and substituted with 0, 1, 2, 3, or 4 independently selected $R^5$ groups, provided that Z is a structure represented by a formula:

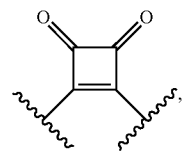 [SMILES: *c1c(*)c(=O)c1=O]

or provided that each of $R^{2a}$ and $R^{2b}$ is not hydrogen, or a salt thereof.

In one aspect, disclosed are compounds having a structure represented by a formula:

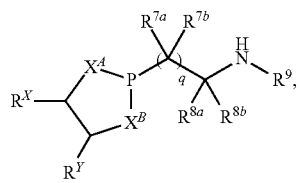

wherein q is selected from 1 and 2; wherein each of $X^A$ and $X^B$ is independently selected from $NR^1$, O, and S; wherein each occurrence of $R^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$, when present, is independently substituted with 0, 1, 2, 3, or 4 independently selected $R^5$ groups; wherein each occurrence of $R^5$, when present, is independently selected from halogen, —$NO_2$, —CN, —OH, —SH, —$NH_2$, C1-C3 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O)(C1-C3 alkyl), —(S=O)(C1-C3 alkyl), —$SO_2$(C1-C3 alkyl), —$CO_2R^{11}$, —(C=O)$NR^{12a}R^{12b}$, —$SO_2NR^{12a}R^{12b}$, —O(C=O)$NR^{12a}E^{12b}$, —$NHSO_2NR^{12a}R^{12b}$, and —NH(C=O)$NR^{12a}R^{12b}$; wherein each occurrence of $R^{11}$, when present, is independently selected from hydrogen and C1-C4 alkyl; wherein each occurrence of $R^{12a}$ and $R^{12b}$, when present, is independently selected from hydrogen and C1-C3 alkyl; wherein each of $R^X$ and $R^Y$ is independently selected from hydrogen, C1-C8 alkyl, C6-C10 aryloxy, C6-C10 aryl, and 4-10 membered heteroaryl, or wherein each of $R^X$ and $R^Y$ are optionally covalently bonded together and, together with the intermediate carbon atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected $R^5$ groups; wherein each of $R^{7a}$ and $R^{7b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{7a}$ and $R^{7b}$ is independently substituted with 0, 1, 2, 3, or 4 independently selected $R^5$ groups; wherein each of $R^{8a}$ and $R^{8b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{8a}$ and $R^{8b}$ is independently substituted with 0, 1, 2, 3, or 4 independently selected $R^5$ groups; wherein $R^9$ is selected from —CN, —SOR$^{20}$, —SO$_2$R$^{20}$, —SO$_3$R$^{20}$, —COR$^{20}$, —CO$_2$R$^{20}$, —CSNHR$^{20}$, —PO(OR$^{21a}$)(OR$^{21b}$), —PO(R$^{21a}$)(R$^{21b}$), and a compound having a structure represented by a formula:

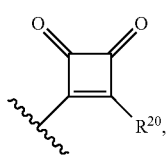

wherein $R^{20}$, when present, is selected from C1-C8 alkyl, C1-C8 alkylamine, (C1-C8)(C1-C8) dialkylamine, C6-C10 arylamine, (C6-C10)(C6-C10) diarylamino, (C6-C10)(C1-C8) aryalkylamine, and C6-C10 aryl and substituted with 0, 1, 2, or 3 groups independently selected from halogen, —NO$_2$, —CN, —OH, —SH, —NH$_2$, and C1-C4 alkyl; and wherein each of $R^{21a}$ and $R^{21b}$, when present, is independently selected from C1-C8 alkyl and C6-C10 aryl and substituted with 0, 1, 2, or 3 groups independently selected from halogen, —NO$_2$, —CN, —OH, —SH, —NH$_2$, and C1-C4 alkyl, or a salt thereof.

In a further aspect, the compound has a structure represented by a formula selected from:

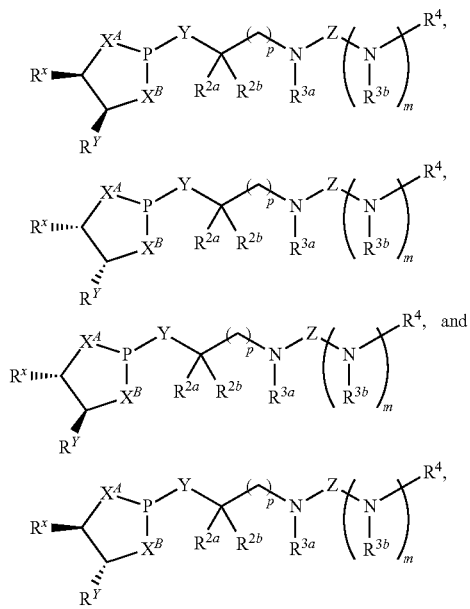

or a salt thereof.

In a further aspect, the compound has a structure represented by a formula:

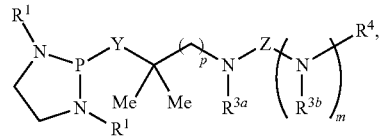

or a salt thereof.

In a further aspect, the compound has a structure represented by a formula:

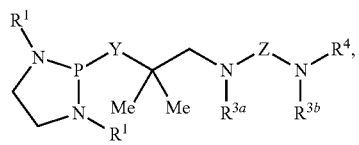

or a salt thereof.

In a further aspect, the compound has a structure represented by a formula:

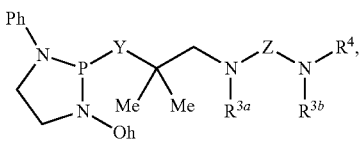

or a salt thereof.

In a further aspect, the compound has a structure represented by a formula:

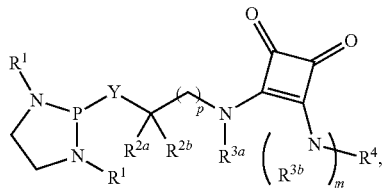

or a salt thereof.

In a further aspect, the compound has a structure represented by a formula:

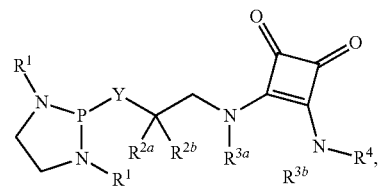

or a salt thereof.

In a further aspect, the compound has a structure represented by a formula:

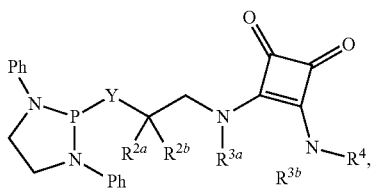

or a salt thereof.

In a further aspect, the compound has a structure represented by a formula:

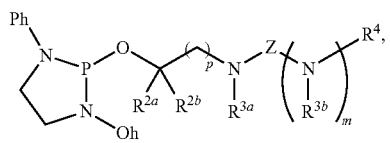

or a salt thereof.

In a further aspect, the compound is selected from:

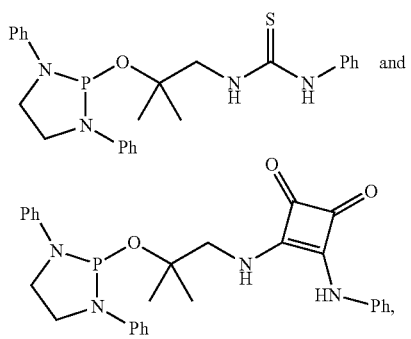

or a salt thereof.

In a further aspect, the compound is:

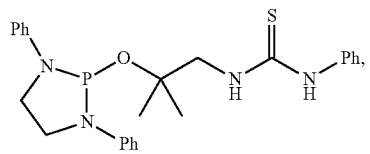 [SMILES: CC(C)(CNC(=S)Nc1ccccc1)OP1N(c2ccccc2)CCN1c1ccccc1]

or a salt thereof.

In a further aspect, the compound is:

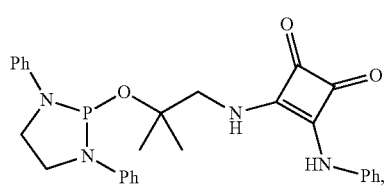

or a salt thereof.

In a further aspect, the compound has a structure represented by a formula:

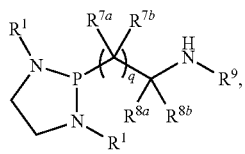

or a salt thereof.

In a further aspect, the compound has a structure represented by a formula:

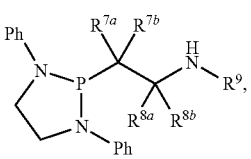

or a salt thereof.

In a further aspect, the compound has a structure represented by a formula:

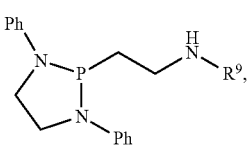

or a salt thereof.

In a further aspect, the compound is:

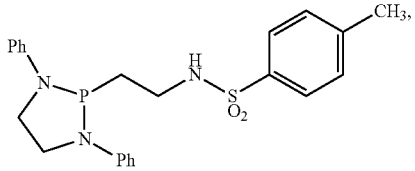 [SMILES: Cc1ccc(S(=O)(=O)NCCP2N(c3ccccc3)CCN2c2ccccc2)cc1]

or a salt thereof.

In a further aspect, m is selected from 0 and 1. In a still further aspect, m is 0. In yet a further aspect, m is 1.

In a further aspect, p is selected from 0, 1, 2, 3, 4, and 5. In a still further aspect, p is selected from 0, 1, 2, 3, and 4. In yet a further aspect, p is selected from 0, 1, 2, and 3. In an even further aspect, p is selected from 0, 1, and 2. In a still further aspect, p is selected from 0 and 1. In yet a further aspect, p is selected from 1 and 2. In an even further aspect, p is 5. In a still further aspect, p is 4. In yet a further aspect, p is 3. In an even further aspect, p is 2. In a still further aspect, p is 1. In yet a further aspect, p is 0.

a. Y Groups

In one aspect, Y is selected from $CH_2$, $CH(CH_3)$, O, and S. In a further aspect, Y is selected from $CH_2$, O, and S. In a still further aspect, Y is selected from O and S. In yet a further aspect, Y is $CH_2$. In an even further aspect, Y is $CH(CH_3)$. In a still further aspect, Y is O. In yet a further aspect, Y is S.

b. Z Groups

In one aspect, Z is selected from C=O, C=S, S=O, $SO_2$, and a structure represented by a formula:

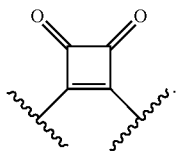 [SMILES: *c1c(*)c(=O)c1=O]

In one aspect, Z is selected from C=O, C=S, S=O, and $SO_2$. In a further aspect, Z is selected from C=O, C=S and $SO_2$. In a still further aspect, Z is selected from C=O, C=S and S=O. In yet a further aspect, Z is selected from C=O and C=S. In an even further aspect, Z is selected from C=O and S=O. In a still further aspect, Z is selected from C=O and $SO_2$. In yet a further aspect, Z is selected from C=S and S=O. In an even further aspect, Z is selected from C=S and $SO_2$. In a still further aspect, Z is selected from S=O and $SO_2$. In yet a further aspect, Z is C=O. In an even further aspect, Z is C=S. In a still further aspect, Z is S=O. In yet a further aspect, Z is $SO_2$.

In a further aspect, Z is a structure represented by a formula:

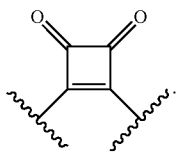

c. $R^{2A}$ and $R^{2B}$ Groups

In one aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups. In a further aspect, each of $R^{2a}$ and $R^{2b}$ is independently selected from hydrogen, C1-C3 alkyl, C1-C3 haloalkyl, C2-C4 alkenyl, C2-C4 alkynyl, C3-C8 cycloalkyl, 4-8 membered heterocycloalkyl, C6-C8 aryl, —(C1-C3 alkyl)(C6-C8 aryl), and 4-8 membered heteroaryl, and substituted with 0, 1, 2, 3, or 4 independently selected $R^5$ groups. In a still further aspect, each of $R^{2a}$ and $R^{2b}$ is hydrogen.

In a further aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl and substituted with 0, 1, 2, or 3 independently selected $R^5$ groups. In a still further aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl and substituted with 0, 1, or 2 independently selected $R^5$ groups. In yet a further aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl and substituted with 0 or 1 $R^5$ group. In an even further aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl and monosubstituted with a $R^5$ group. In a still further aspect, each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and unsubstituted.

In a further aspect, each of $R^{2a}$ and $R^{2b}$ is independently selected from C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups. In a still further aspect, each of $R^{2a}$ and $R^{2b}$ is independently selected from C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl. In yet a further aspect, each of $R^{2a}$ and $R^{2b}$ is independently selected from C1-C3 alkyl, C1-C3 haloalkyl, C2-C4 alkenyl, C2-C3 C4 alkynyl, C3-C8 cycloalkyl, 4-8 membered heterocycloalkyl, C6-C8 aryl, —(C1-C3 alkyl)(C6-C8 aryl), and 4-8 membered heteroaryl. In an even further aspect, each of $R^{2a}$ and $R^{2b}$ is independently selected from methyl, ethyl, —$CH_2F$, —$CHF_2$, —$CF_3$, —$CH_2CH_2F$, —$CH_2Cl$, —$CHCl_2$, —$CCl_3$, —$CH_2CH_2Cl$, ethenyl, propenyl, ethynyl, propynyl, C3-C8 cycloalkyl, 4-8 membered heterocycloalkyl, C6-C8 aryl, —(C1-C3 alkyl)(C6-C8 aryl), and 4-8 membered heteroaryl. In a still further aspect, each of $R^{2a}$ and $R^{2b}$ is independently selected from methyl, ethyl, —$CH_2F$, —$CHF_2$, —$CF_3$, —$CH_2CH_2F$, —$CH_2Cl$, —$CHCl_2$, —$CCl_3$, —$CH_2CH_2Cl$, ethenyl, ethynyl, C3-C8 cycloalkyl, 4-8 membered heterocycloalkyl, C6-C8 aryl, —(C1-C3 alkyl)(C6-C8 aryl), and 4-8 membered heteroaryl. In yet a further aspect, each of $R^{2a}$ and $R^{2b}$ is independently selected from methyl, —CH$_2$F, —CHF$_2$, —CF$_3$, —CH$_2$Cl, —CHCl$_2$, —CCl$_3$, C3-C8 cycloalkyl, 4-8 membered heterocycloalkyl, C6-C8 aryl, —(C1-C3 alkyl)(C6-C8 aryl), and 4-8 membered heteroaryl.

In a further aspect, each of $R^{2a}$ and $R^{2b}$ is independently selected from hydrogen and C1-C6 alkyl. In a still further aspect, each of $R^{2a}$ and $R^{2b}$ is independently selected from hydrogen, methyl, ethyl, n-propyl, i-propyl, n-butyl, i-butyl, s-butyl, and t-butyl. In yet a further aspect, each of $R^{2a}$ and $R^{2b}$ is independently selected from hydrogen, methyl, ethyl, n-propyl, and i-propyl. In an even further aspect, each of $R^{2a}$ and $R^{2b}$ is independently selected from hydrogen, methyl and ethyl. In a still further aspect, each of $R^{2a}$ and $R^{2b}$ is independently selected from hydrogen and ethyl. In yet a further aspect each of $R^{2a}$ and $R^{2b}$ is independently selected from hydrogen and methyl.

In a further aspect, each of $R^{2a}$ and $R^{2b}$ is C1-C6 alkyl. In a still further aspect, each of $R^{2a}$ and $R^{2b}$ is independently selected from methyl, ethyl, n-propyl, i-propyl, n-butyl, i-butyl, s-butyl, and t-butyl. In yet a further aspect, each of $R^{2a}$ and $R^{2b}$ is independently selected from methyl, ethyl, n-propyl, and i-propyl. In an even further aspect, each of $R^{2a}$ and $R^{2b}$ is independently selected from methyl and ethyl. In a still further aspect, each of $R^{2a}$ and $R^{2b}$ is ethyl. In yet a further aspect, each of $R^{2a}$ and $R^{2b}$ is methyl.

d. $R^{3A}$ AND $R^{3B}$ GROUPS

In one aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0, 1, 2, 3, or 4 independently selected $R^5$ groups. In a further aspect, each of $R^{3a}$ and $R^{3b}$, when present, is independently selected from hydrogen, C1-C3 alkyl, C1-C3 haloalkyl, C2-C8 alkenyl, C2-C8 alkynyl, C3-C8 cycloalkyl, 4-8 membered heterocycloalkyl, C6-C8 aryl, —(C1-C3 alkyl)(C6-C8 aryl), and 4-8 membered heteroaryl, and wherein each of $R^{3a}$ and $R^{3b}$ is independently substituted with 0, 1, 2, 3, or 4 independently selected $R^5$ groups. In a still further aspect, each of $R^{3a}$ and $R^{3b}$, when present, is hydrogen.

In a further aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0, 1, 2, or 3 independently selected $R^5$ groups. In a still further aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0, 1, or 2 independently selected $R^5$ groups. In yet a further aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0 or 1 $R^5$ group. In an even further aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently monosubstituted with a $R^5$ group. In a still further aspect, each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{ab}$ is unsubstituted.

In a further aspect, each of $R^{1a}$ and $R^{3b}$, when present, is independently selected from hydrogen and C1-C6 alkyl. In a still further aspect, each of $R^{3a}$ and $R^{3b}$, when present, is independently selected from hydrogen, methyl, ethyl, n-propyl, i-propyl, n-butyl, i-butyl, s-butyl, and t-butyl. In yet a further aspect, each of $R^{3a}$ and $R^{3b}$, when present, is independently selected from hydrogen, methyl, ethyl, n-propyl, and i-propyl. In an even further aspect, each $R^3$ is independently selected from H, methyl, and ethyl. In a still further aspect, each of $R^{3a}$ and $R^{3b}$, when present, is independently selected from hydrogen and ethyl. In yet a further aspect, each of $R^{3a}$ and $R^{3b}$, when present, is independently selected from hydrogen and methyl.

In a further aspect, each of $R^{3a}$ and $R^{3b}$, when present, is independently C1-C6 alkyl. In a still further aspect, each of $R^{3a}$ and $R^{3b}$, when present, is independently selected from methyl, ethyl, n-propyl, i-propyl, n-butyl, i-butyl, s-butyl, and t-butyl. In yet a further aspect, each of $R^{3a}$ and $R^{3b}$, when present, is independently selected from methyl, ethyl, n-propyl, and i-propyl. In an even further aspect, each of $R^{1a}$ and $R^{3b}$, when present, is independently selected from methyl and ethyl. In a still further aspect, each of $R^{1a}$ and $R^{3b}$, when present, is ethyl. In yet a further aspect, each of $R^{1a}$ and $R^{3b}$, when present, is methyl.

e. $R^4$ Groups

In one aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and substituted with 0, 1, 2, 3, or 4 independently selected $R^5$ groups. In a further aspect, $R^4$ is selected from hydrogen, C1-C3 alkyl, C1-C3 haloalkyl, C2-C4 alkenyl, C2-C4 alkynyl, C3-C8 cycloalkyl, 4-8 membered heterocycloalkyl, C6-C8 aryl, and 4-8 membered heteroaryl, and —(C1-C3 alkyl)(C6-C8 aryl), and wherein $R^4$ is substituted with 0, 1, 2, 3, or 4 independently selected $R^5$ groups.

In a further aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and substituted with 0, 1, 2, or 3 independently selected $R^5$ groups. In a still further aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and substituted with 0, 1, or 2 independently selected $R^5$ groups. In yet a further aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and substituted with 0 or 1 $R^5$ group. In an even further aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and monosubstituted with a $R^5$ group. In a still further aspect, $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, 4-10 membered heteroaryl, and —(C1-C3 alkyl)(C6-C10 aryl), and unsubstituted.

In a further aspect, $R^4$ is selected from C3-C10 cycloalkyl, C6-C10 aryl, and —(C1-C3 alkyl)(C6-C10 aryl). In a still further aspect, $R^4$ is selected from C3-C8 cycloalkyl, C6-C8 aryl, and —(C1-C3 alkyl)(C6-C8 aryl). In yet a further aspect, $R^4$ is selected from cyclohexyl, phenyl, and benzyl. In an even further aspect, $R^4$ is selected from cyclohexyl and phenyl. In a still further aspect, $R^4$ is selected from cyclohexyl and benzyl. In yet a further aspect, $R^4$ is selected from phenyl and benzyl. In an even further aspect, $R^4$ is cyclohexyl. In a still further aspect, $R^4$ is phenyl. In an even further aspect, $R^4$ is benzyl.

2. Prophetic Compound Examples

The following compound examples are prophetic, and can be prepared using the synthesis methods described herein above and other general methods as needed as would be known to one skilled in the art. It is anticipated that the prophetic compounds would be useful in the preparation of vinylphosphonates, and such utility can be determined using the synthetic methods described herein below.

In one aspect, a compound can be selected from:

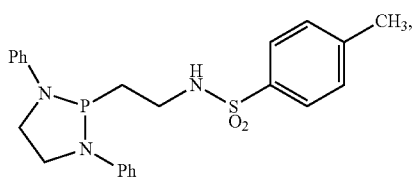 [SMILES: Cc1ccc(S(=O)(=O)NCCP2N(c3ccccc3)CCN2c2ccccc2)cc1]

or a derivative thereof.

In one aspect, a compound can be selected from:

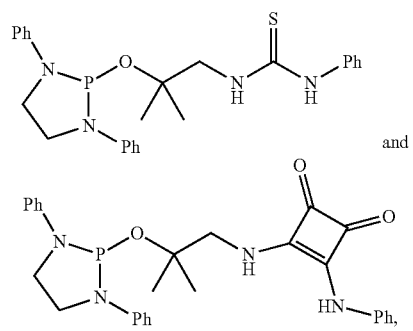

or a derivative thereof.

In one aspect, a compound can be selected from:

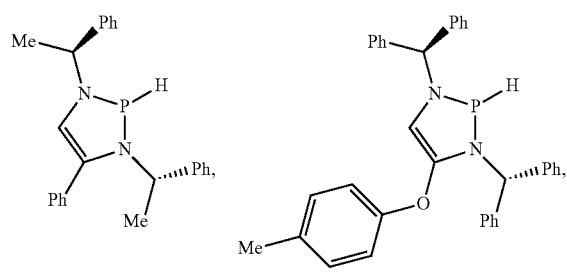

-continued

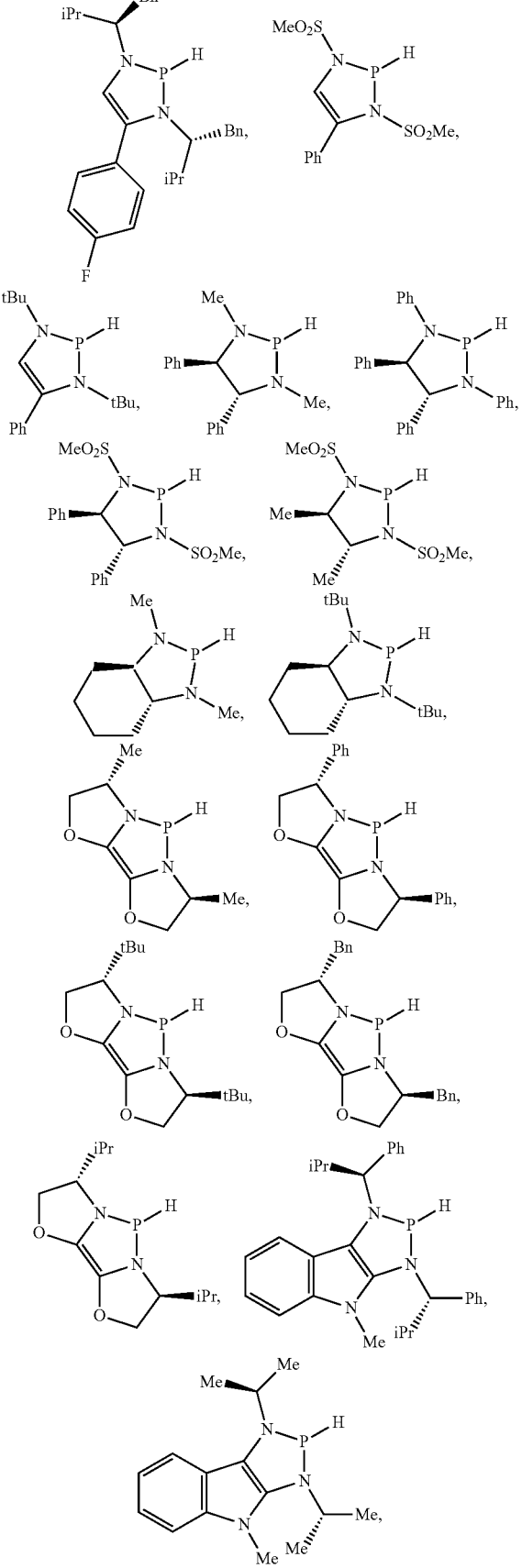

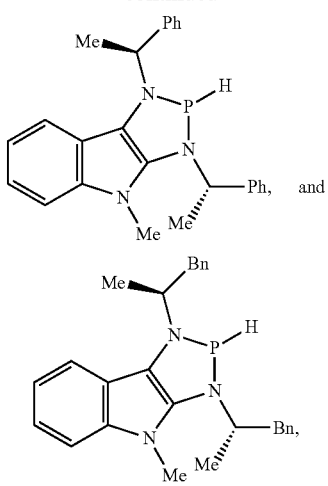
or a derivative thereof.
In one aspect, a compound can be selected from:
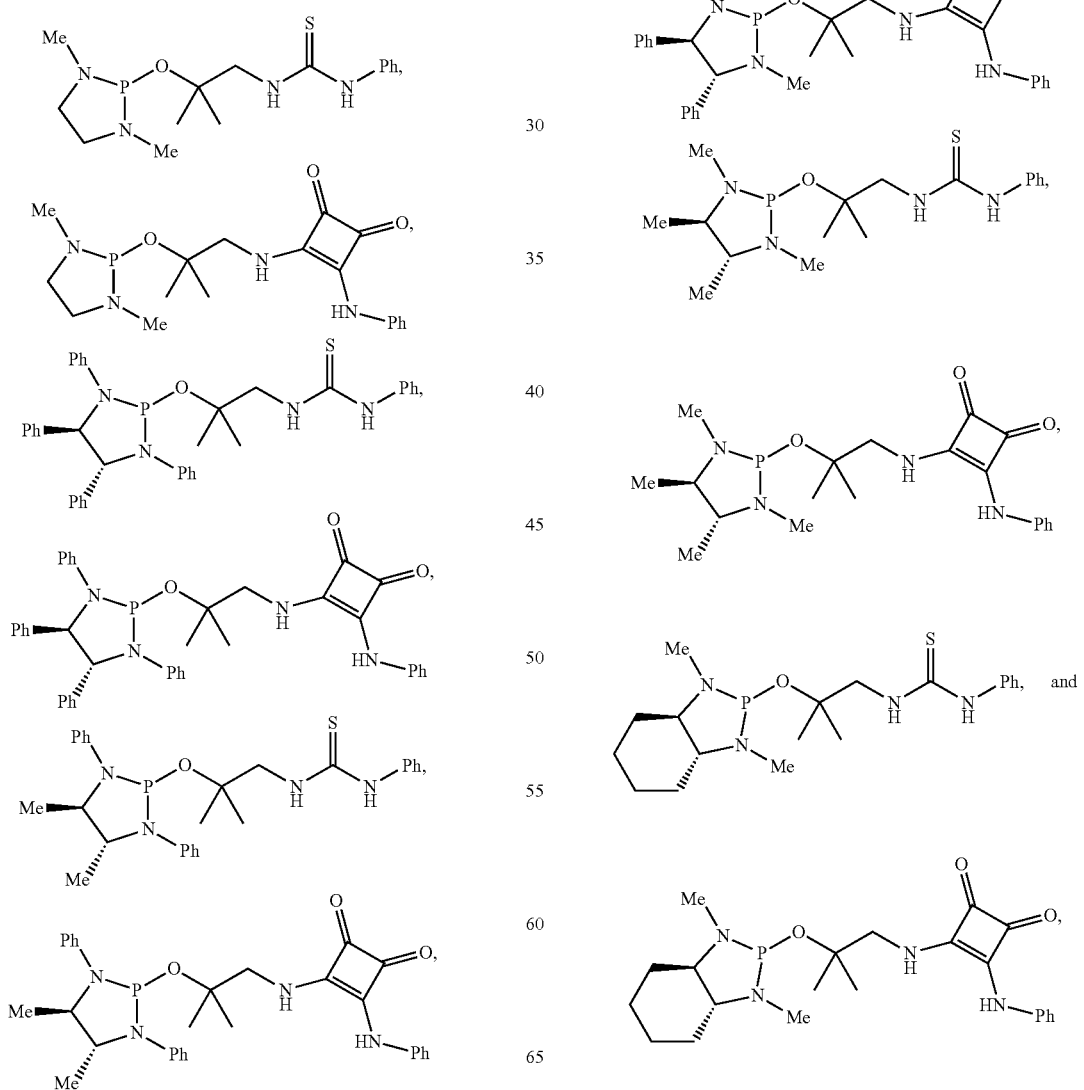
or a derivative thereof.

In one aspect, a compound can be selected from:
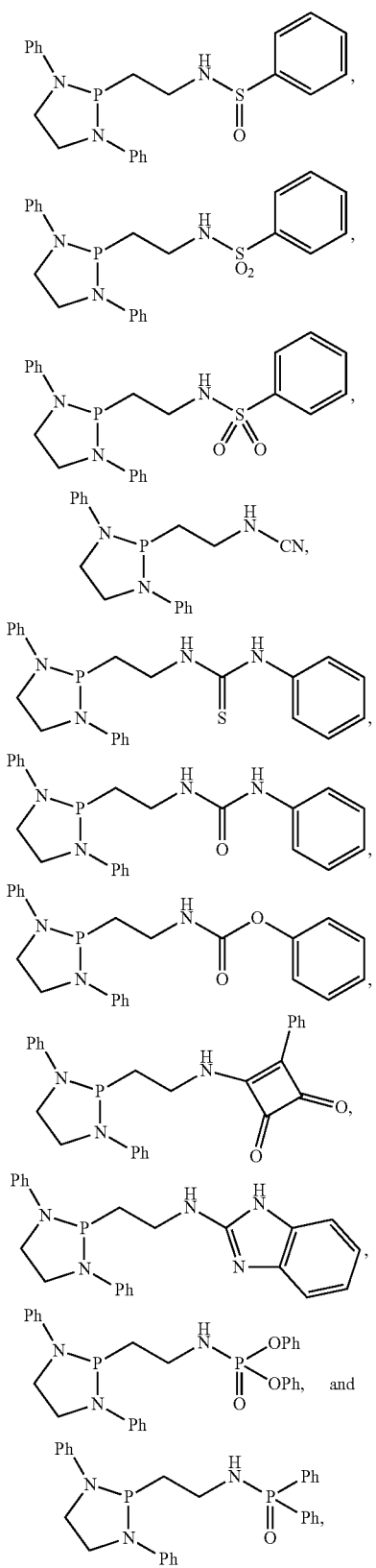
or a derivative thereof.
In one aspect, a compound can be selected from:
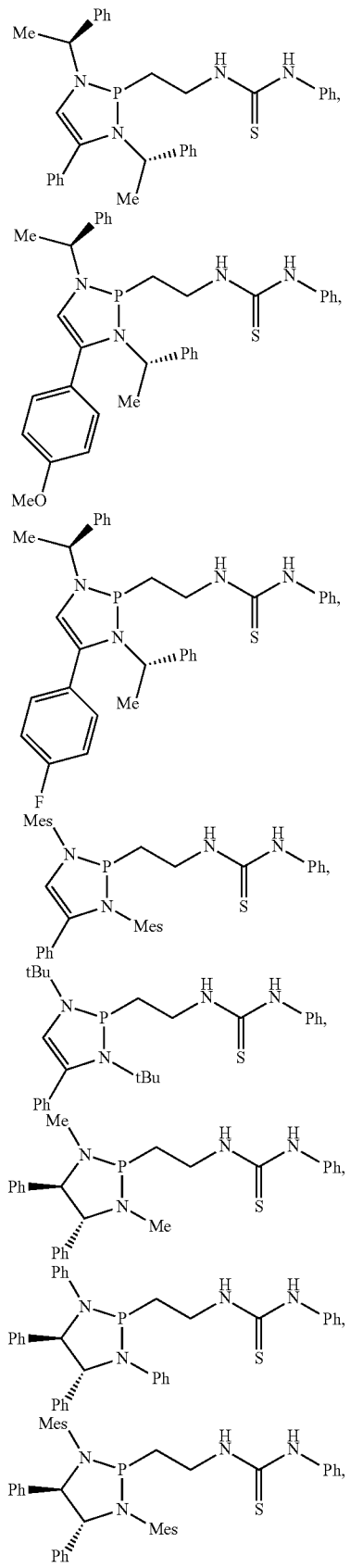

-continued

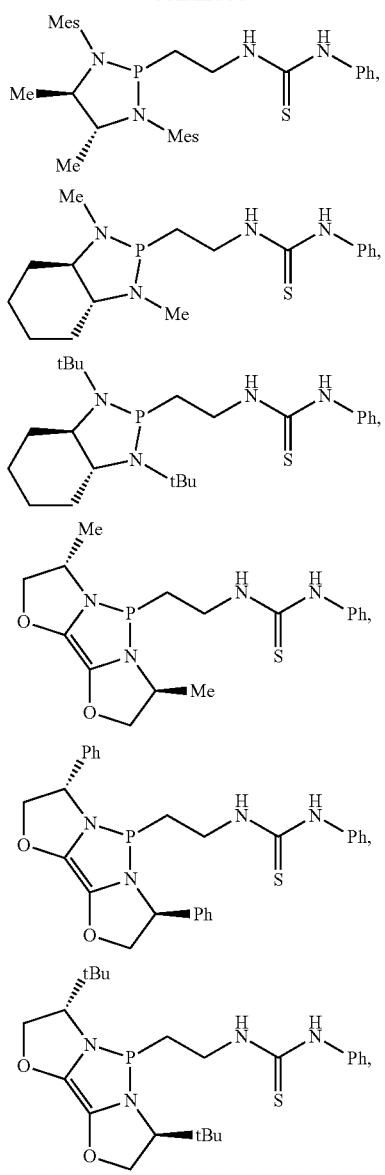

-continued

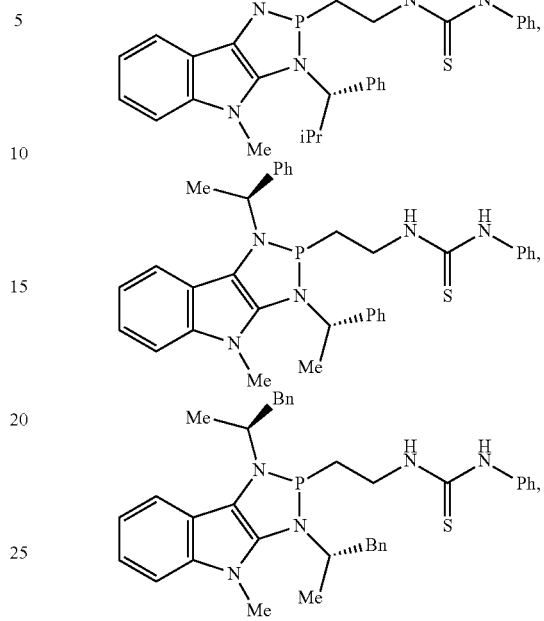

or a derivative thereof.

D. METHODS OF MAKING α-AMINOPHOSPHONATES

In one aspect, the invention relates to methods of making N-heterocyclic phosphines useful in the preparation of α-aminophosphonates. The α-aminophosphonates of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Thus, in one aspect, disclosed are methods of making a compound having a structure represented by a formula:

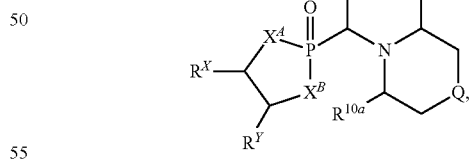

wherein Q is selected from O, S, C=O, S=O, SO$_2$, and NW; wherein each of $X^A$ and $X^B$ is independently selected from NR$^1$, O, and S; wherein each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups; wherein each occurrence of R$^5$, when present, is independently selected from halogen, —NO$_2$, —CN, —OH, —SH, —NH$_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O)(C1-C3 alkyl), —(S=O)(C1-C3 alkyl), —SO$_2$(C1-C3 alkyl), —CO$_2$R$^{11}$, —(C=O)NR$^{12a}$R$^{12b}$, —SO$_2$NR$^{12a}$R$^{12b}$, —O(C=O)NR$^{12a}$R$^{12b}$, —NHSO$_2$NR$^{12a}$R$^{12b}$, and —NH(C=O)NR$^{12a}$R$^{12b}$; wherein each occurrence of R$^{11}$, when present, is independently selected from hydrogen and C1-C4 alkyl; wherein each occurrence of R$^{12a}$ and R$^{12b}$, when present, is independently selected from hydrogen and C1-C3 alkyl; wherein each of R$^X$ and R$^Y$ is independently selected from hydrogen, C1-C8 alkyl, C6-C10 aryloxy, C6-C10 aryl, and 4-10 membered heteroaryl, or wherein each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups; wherein R$^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; and wherein each of R$^{10a}$ and R$^{10b}$ is independently selected from hydrogen and C1-C4 alkyl, or a salt thereof, the method comprising the step of reacting an aldehyde having a structure represented by a formula:

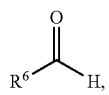

or a salt thereof, with a heterocycloalkane having a structure represented by a formula:

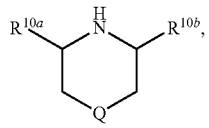

or a salt thereof, in the presence of a reagent having a structure represented by a formula:

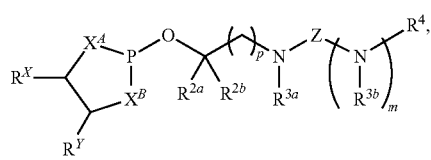

wherein m is selected from 0 and 1; wherein p is selected from 0, 1, 2, 3, 4, and 5; wherein Z is selected from C=O, C=S, S=O, SO$_2$, and a structure represented by a formula:

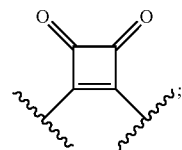 [SMILES: *c1c(*)c(=O)c1=O]

wherein each of R$^{2a}$ and R$^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; wherein each of R$^{3a}$ and R$^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of R$^{3a}$ and R$^{3b}$ is independently substituted with 0, 1, 2, 3, or 4 independently selected R$^5$ groups; and wherein R$^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, and 4-10 membered heteroaryl, and —(C1-C3 alkyl)(C6-C10 aryl), and substituted with 0, 1, 2, 3, or 4 independently selected R$^5$ groups, or a salt thereof In a further aspect, the aldehyde, the heterocycloalkane, and the reagent are simultaneously reacted. In a still further aspect, the aldehyde and the heterocycloalkane react to form a reaction product and wherein the reaction product reacts with the reagent. In yet a further aspect, the aldehyde and the reagent react to form a reaction product and wherein the reaction product reacts with the heterocycloalkane. In an even further aspect, the heterocycloalkane and the reagent react to form a reaction product and wherein the reaction product reacts with the aldehyde.

In various aspects, the process provided herein can be used to prepare bioactive compounds having a phosphorus-carbon bond. A non-limiting list of bioactive compounds that can be prepared includes, for example, antibiotics (e.g., dehydrophos; see PNAS, 2010, 107, 17557-17562).

1. Route I

In one aspect, α-aminophosphonates can be prepared as shown below.

SCHEME 1A.

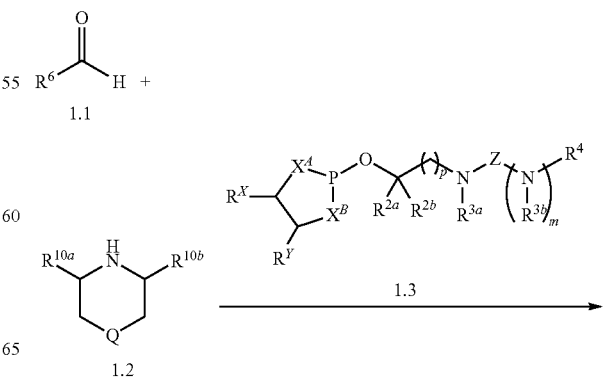

-continued

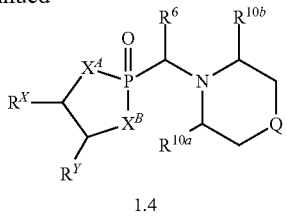

1.4

Compounds are represented in generic form, with substituents as noted in compound descriptions elsewhere herein. A more specific example is set forth below.

SCHEME 1B.

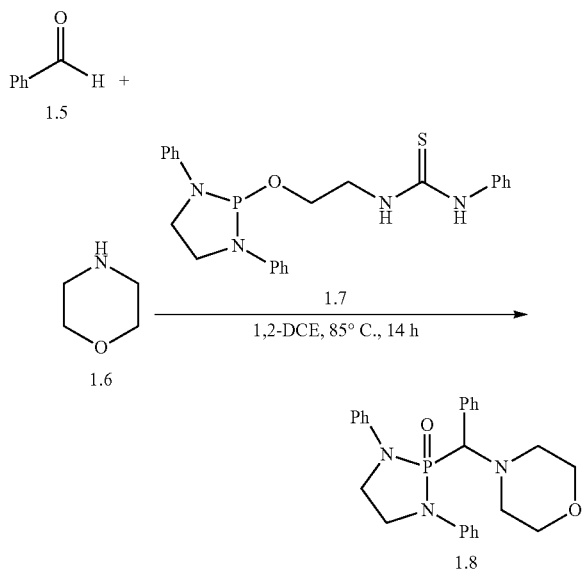

In one aspect, the synthesis of α-aminophosphonates can begin with an aldehyde. Aldehydes are commercially available or readily prepared by one skilled in the art. Thus, compounds of type 1.3, and similar compounds, can be prepared according to reaction Scheme 1B above. Compounds of type 1.8 can be prepared by a Mannich Arbuzov cascade reaction of an appropriate aldehyde derivative, e.g., 1.5 as shown above, and an appropriate N-heterocyclic phosphine, e.g., 1.7 as shown above. The Mannich Arbuzov cascade reaction is carried out in the presence of an appropriate amine, e.g., 1.6 as shown above, in an appropriate solvent, e.g., 1,2-dichloroethane, at an appropriate temperature, e.g., 85° C., for an appropriate period of time, e.g., 14 hours. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted α-aminophosphonates similar to Formula 1.4.

E. METHODS OF MAKING N-HETEROCYCLIC PHOSPHINES

In one aspect, disclosed are methods of making a compound having a structure represented by a formula:

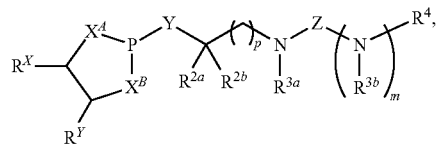

wherein m is selected from 0 and 1; wherein p is selected from 0, 1, 2, 3, 4, and 5; wherein Y is selected from $CH_2$, $CH(CH_3)$, O, and S; wherein each of $X^A$ and $X^B$ is independently selected from $NR^1$, O, and S; wherein each occurrence of $R^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$, when present, is independently substituted with 0, 1, 2, 3, or 4 independently selected $R^5$ groups; wherein each occurrence of $R^5$, when present, is independently selected from halogen, $-NO_2$, —CN, —OH, —SH, $-NH_2$, C1-C3 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl (C1-C3 alkoxy), C1-C3 alkylamino, (C1-C3)(C1-C3) dialkylamino, C3-C7 cycloalkyl, C6-C10 aryl, —(C=O) (C1-C3 alkyl), —(S=O)(C1-C3 alkyl), $-SO_2$(C1-C3 alkyl), $-CO_2R^{11}$, $-(C=O)NR^{12a}R^{12b}$, $-SO_2NR^{12a}R^{12b}$, $-O(C=O)NR^{12a}R^{12b}$, $-NHSO_2NR^{21a}R^{12b}$, and —NH $(C=O)NR^{12a}R^{12b}$; wherein each occurrence of $R^{11}$, when present, is independently selected from hydrogen and C1-C4 alkyl; wherein each occurrence of $R^{12a}$ and $R^{12b}$, when present, is independently selected from hydrogen and C1-C3 alkyl; wherein Z is selected from C=O, C=S, S=O, $SO_2$, and a structure represented by a formula:

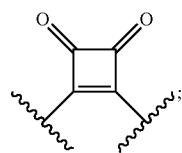 [SMILES: *c1c(*)c(=O)c1=O]

wherein each of $R^{2a}$ and $R^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups; wherein each of $R^{3a}$ and $R^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of $R^{3a}$ and $R^{3b}$ is independently substituted with 0, 1, 2, 3, or 4 independently selected $R^5$ groups; and wherein $R^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, and 4-10 membered heteroaryl, and —(C1-C3 alkyl)(C6-C10 aryl), and substituted with 0, 1, 2, 3, or 4 independently selected $R^5$ groups, provided that Z is a structure represented by a formula:

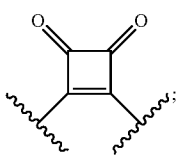

or provided that each of $R^{2a}$ and $R^{2b}$ is not hydrogen, or a salt thereof, the method comprising: (a) providing a first compound having a structure represented by a formula:

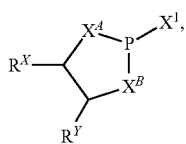

wherein $X^1$ is halogen, or a derivative thereof; and (b) reacting with a second compound having a structure represented by a formula:

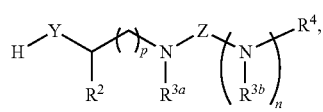

or a derivative thereof, in the presence of a base.

In a further aspect, the base is an amine base. In a still further aspect, the base is selected from trimethylamine, tripropylamine, triisopropylamine, tri-tert-butylamine, N,N-dimethylethanamine, N-ethyl-N-methylpropan-2-amine, N-ethyl-N-isopropylpropan-2-amine, morpholine, N-methylmorpholine, diisopropylethylamine, DABCO, triphenylamine, quinuclidine, trimethylamine, tripropylamine, triisopropylamine, tri-tert-butylamine, pyrrolidine, pyridine, 2,6-lutidine, 1,8-diazabicyclo[5.4.0]undec-7-ene, tributylamine, and triethylamine. In yet a further aspect, the base is triethylamine.

In a further aspect, providing comprises reacting a compound having a structure represented by a formula:

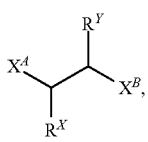

with a phosphine in the presence of a base.

In a further aspect, the phosphine is a trihalophosphine. In a still further aspect, the phosphine is selected from tribromophosphine and trichlorophosphine. In yet a further aspect, the phosphine is trichlorophosphine.

In a further aspect, the base is an amine base. In a still further aspect, the base is selected from diisopropylethylamine, DABCO, triphenylamine, quinuclidine, pyrrolidine, pyridine, 2,6-lutidine, 1,8-diazabicyclo[5.4.0]undec-7-ene, Hunig's base, tributylamine, and triethylamine. In yet a further aspect, the base is triethylamine.

The compounds provided herein, including salts thereof, can be prepared using known organic synthesis techniques and can be synthesized according to any of numerous possible synthetic routes.

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The chemistry of protecting groups can be found, for example, in *Protecting Group Chemistry*, 1$^{st}$ Ed., Oxford University Press, 2000; *March's Advanced Organic Chemistry: Reactions, Mechanisms, and Structure*, 5$^{th}$ Ed., Wiley-Interscience Publication, 2001; and Peturssion, S. et al., "Protecting Groups in Carbohydrate Chemistry," *J. Chem. Educ.*, 74(11), 1297 (1997).

Reactions can be monitored using an appropriate method. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified using appropriate methods such as high performance liquid chromatography (HPLC) ("*Preparative LC-MS Purification: Improved Compound Specific Method Optimization*" K. F. Blom, et al., *J. Combi. Chem.* 6(6), 874 (2004)) and normal phase silica chromatography.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

1. Route

In one aspect, substituted N-heterocyclic phosphine halide intermediates can be prepared as shown below.

SCHEME 2A.

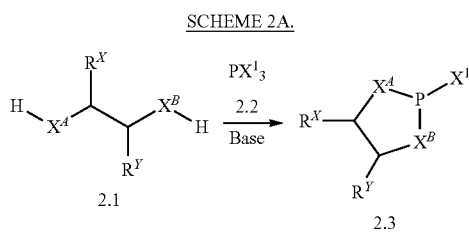

Compounds are represented in generic form, with substituents as noted in compound descriptions elsewhere herein and wherein $X^1$ is halogen. A more specific example is set forth below.

SCHEME 2B.

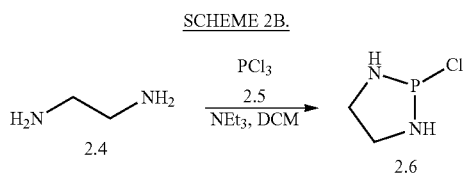

In one aspect, the synthesis of N-heterocyclic phosphine halide intermediates can begin with an ethylene derivative. Ethylene derivatives are commercially available or readily prepared by one skilled in the art. Thus, compounds of type 2.6, and similar compounds, can be prepared according to reaction Scheme 2B above. Compounds of type 2.6 can be prepared by a cyclization reaction of an appropriate ethylene derivative, e.g., 2.4 as shown above. The cyclization reaction is carried out in the presence of an appropriate phosphorous trihalide, e.g., 2.5 as shown above, and an appropriate base, e.g., triethylamine, in an appropriate solvent, e.g., dichloromethane. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted N-heterocyclic phosphine halide intermediates similar to Formula 2.3.

2. Route II

In one aspect, substituted N-heterocyclic phosphine analogs can be prepared as shown below.

SCHEME 3A.

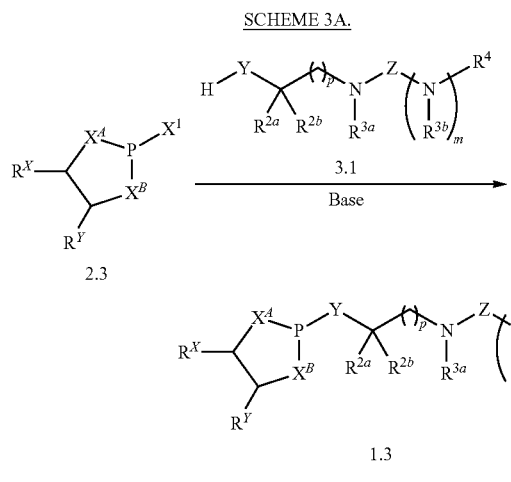

Compounds are represented in generic form, with substituents as noted in compound descriptions elsewhere herein, wherein $X^1$ is halogen. A more specific example is set forth below.

SCHEME 3B.

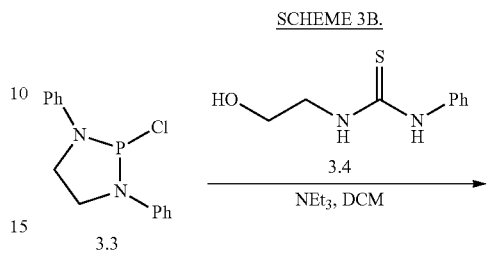

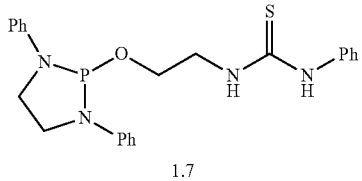

In one aspect, the synthesis of N-heterocyclic phosphine analogs can begin with an N-heterocyclic phosphine halide. N-heterocyclic phosphine halides are commercially available or readily prepared by one skilled in the art. Thus, compounds of type 1.7, and similar compounds, can be prepared according to reaction Scheme 3B above. Compounds of type 1.7 can be prepared by a substitution reaction of an appropriate N-heterocyclic phosphine halide, e.g., 3.3 as shown above. The substitution reaction is carried out in the presence of an appropriate urea, thiourea, sulfonyl, or sulfonyl derivative, e.g., 3.4 as shown above, and an appropriate base, e.g., triethylamine, in an appropriate solvent, e.g., dichloromethane. As can be appreciated by one skilled in the art, the above reaction provides an example of a generalized approach wherein compounds similar in structure to the specific reactants above (compounds similar to compounds of type 2.3 and 3.1), can be substituted in the reaction to provide substituted N-heterocyclic phosphine analogs similar to Formula 1.3.

3. Route III

In one aspect, substituted N-heterocyclic phosphine analogs can be prepared as shown below.

SCHEME 4A.

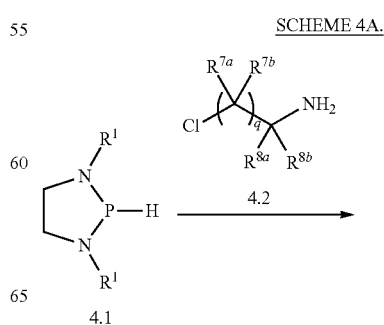

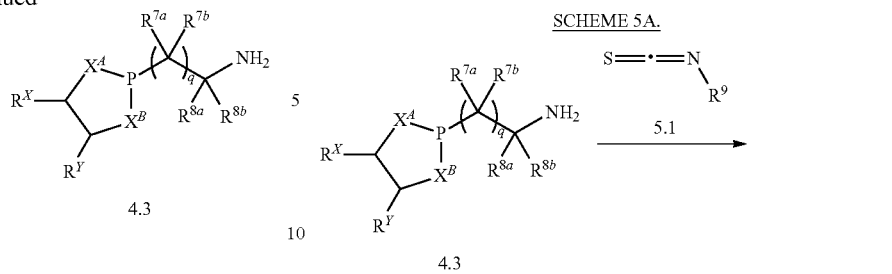

4.3

Compounds are represented in generic form, with substituents as noted in compound descriptions elsewhere herein. A more specific example is set forth below.

SCHEME 4B.

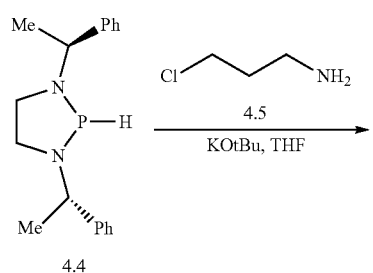

4.4

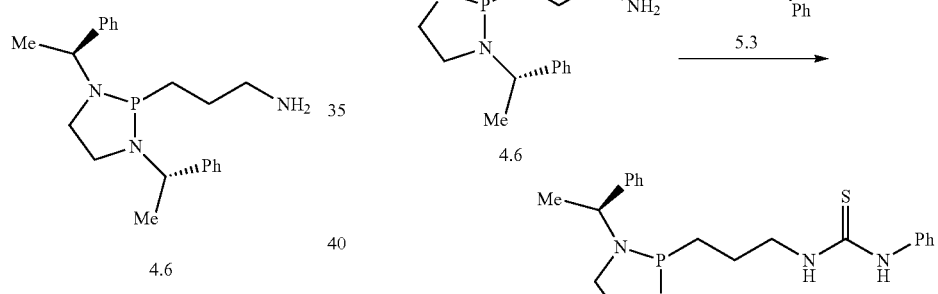

In one aspect, the synthesis of N-heterocyclic phosphine analogs can begin with a substituted diazaphospholidine. Substituted diazaphospholidines are commercially available or readily prepared by one skilled in the art. Thus, compounds of type 4.6, and similar compounds, can be prepared according to reaction Scheme 4B above. Compounds of type 4.6 can be prepared by an alkylation reaction of an appropriate diazaphospholidine, e.g., 4.4 as shown above. The alkylation reaction is carried out in the presence of an appropriate alkyl halide, e.g., 4.5 as shown above, and an appropriate base, e.g., potassium tert-butoxide, in an appropriate solvent, e.g., tetrahydrofuran. As can be appreciated by one skilled in the art, the above reaction provides an example of a generalized approach wherein compounds similar in structure to the specific reactants above (compounds similar to compounds of type 4.1 and 5.2), can be substituted in the reaction to provide substituted N-heterocyclic phosphine analogs similar to Formula 4.3.

4. Route IV

In one aspect, substituted N-heterocyclic phosphine analogs can be prepared as shown below.

Compounds are represented in generic form, with substituents as noted in compound descriptions elsewhere herein. A more specific example is set forth below.

In one aspect, the synthesis of N-heterocyclic phosphine analogs can begin with an amine. Amines are commercially available or readily prepared by one skilled in the art. Thus, compounds of type 5.4, and similar compounds, can be prepared according to reaction Scheme 5B above. Compounds of type 5.4 can be prepared by nucleophilic addition of an appropriate amine, e.g., 4.6 as shown above, to an appropriate isothiocyanate, e.g., 5.3 as shown above. As can be appreciated by one skilled in the art, the above reaction provides an example of a generalized approach wherein compounds similar in structure to the specific reactants above (compounds similar to compounds of type 4.3 and 5.1), can be substituted in the reaction to provide substituted N-heterocyclic phosphine analogs similar to Formula 5.2.

F. METHODS OF MAKING CHIRAL N-HETEROCYCLIC PHOSPHINES

In one aspect, disclosed are methods of making chiral N-heterocyclic phosphines. The compounds provided herein, including salts thereof, can be prepared using known organic synthesis techniques and can be synthesized according to any of numerous possible synthetic routes.

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The chemistry of protecting groups can be found, for example, in *Protecting Group Chemistry*, 1st Ed., Oxford University Press, 2000; *March's Advanced Organic Chemistry: Reactions, Mechanisms, and Structure*, 5th Ed., Wiley-Interscience Publication, 2001; and Peturssion, S. et al., "Protecting Groups in Carbohydrate Chemistry," *J. Chem. Educ.*, 74(11), 1297 (1997).

Reactions can be monitored using an appropriate method. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified using appropriate methods such as high performance liquid chromatography (HPLC) ("*Preparative LC-MS Purification: Improved Compound Specific Method Optimization*" K. F. Blom, et al., *J. Combi. Chem.* 6(6), 874 (2004)) and normal phase silica chromatography.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry*(Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

1. Route

In one aspect, substituted chiral N-heterocyclic phosphine reagents can be prepared as shown below.

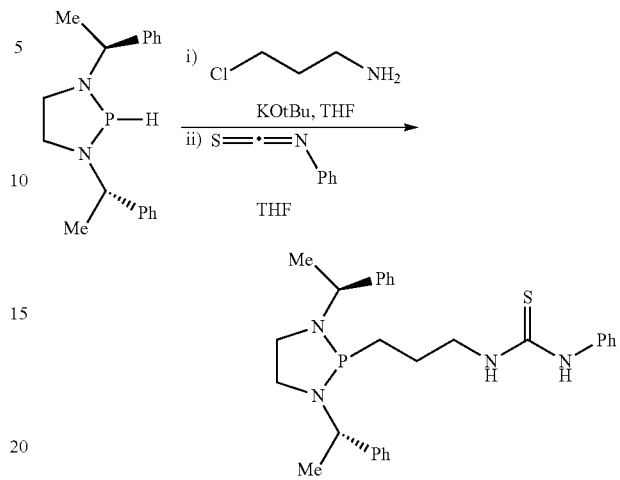

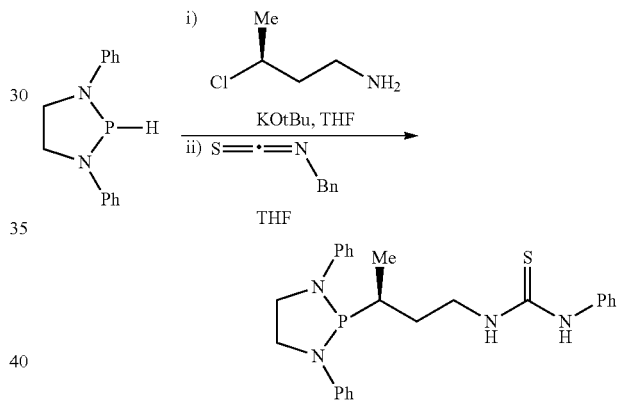

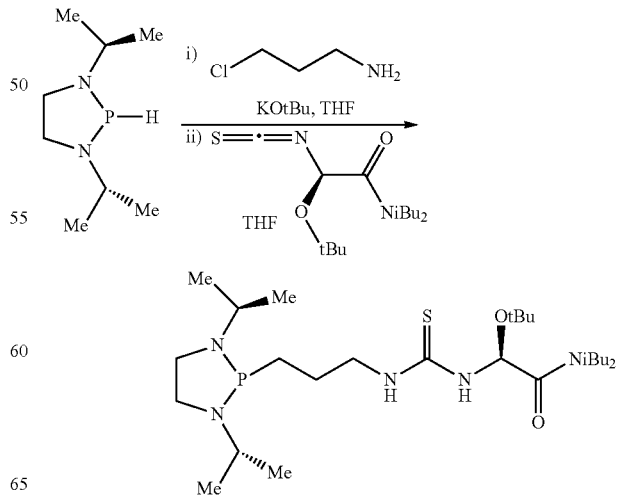

SCHEME 6D.

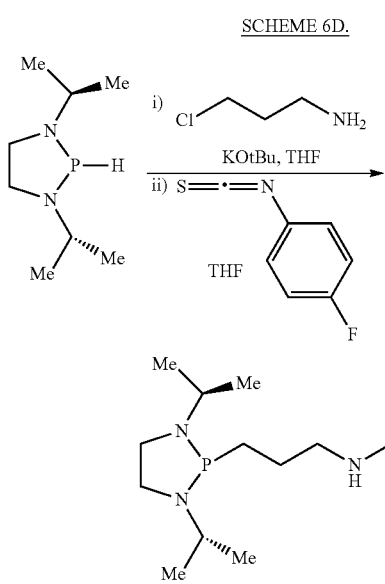

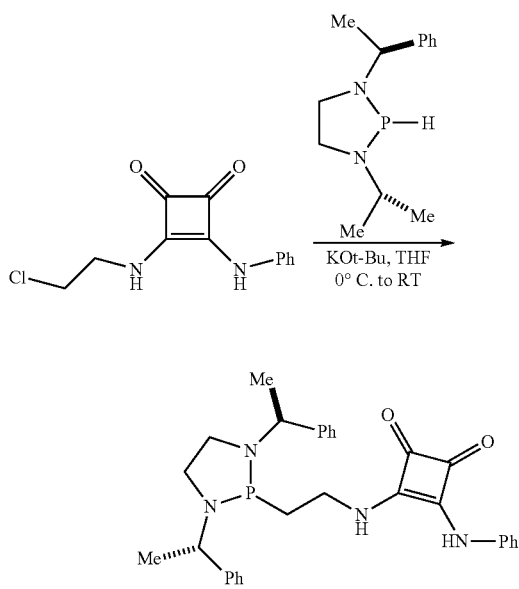

2. Route II

In one aspect, substituted chiral N-heterocyclic phosphine reagents can be prepared as shown below.

SCHEME 7A.

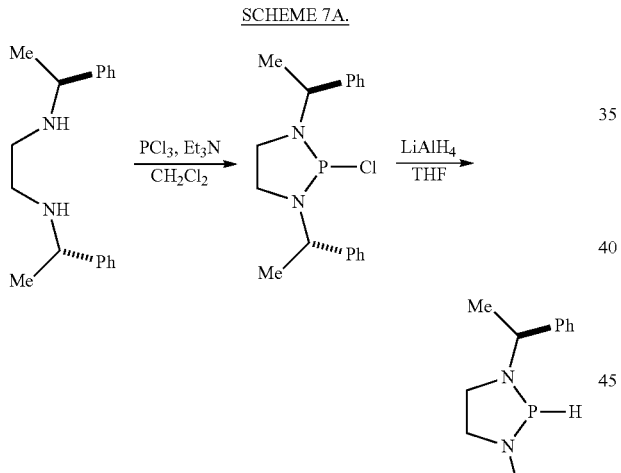

3. Route III

In one aspect, substituted chiral N-heterocyclic phosphine reagents can be prepared as shown below.

SCHEME 8A.

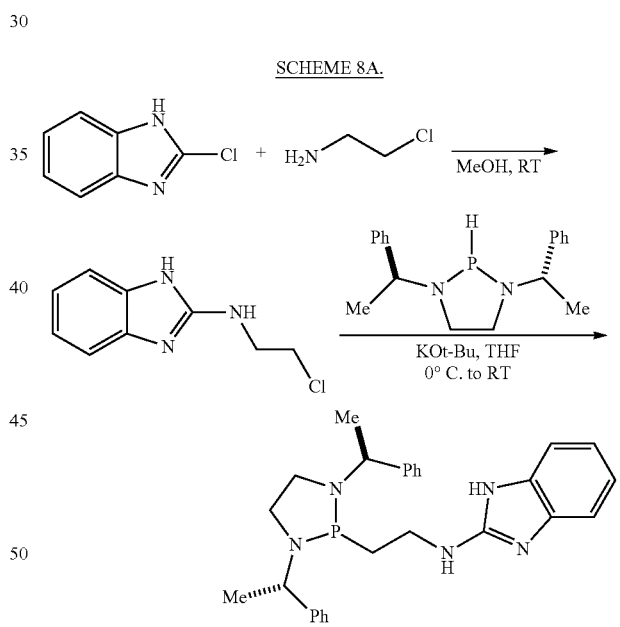

SCHEME 7B.

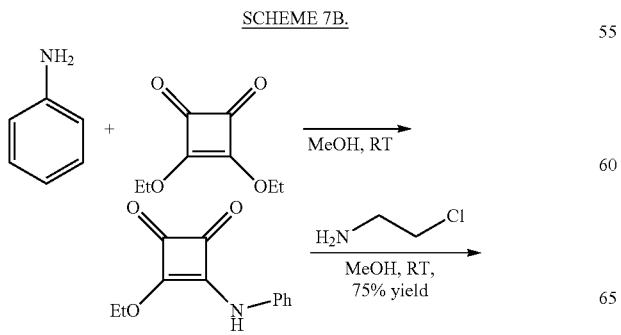

4. Route IV

In one aspect, substituted chiral N-heterocyclic phosphine reagents can be prepared as shown below.

SCHEME 9A.

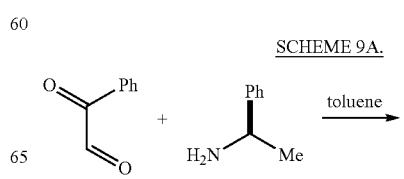

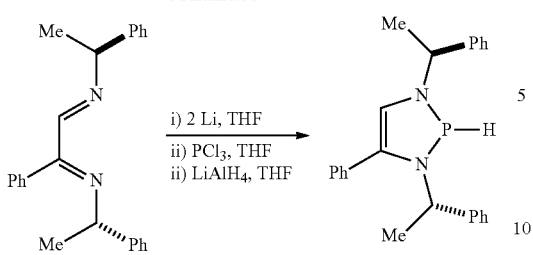
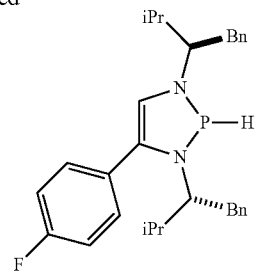
SCHEME 9B.
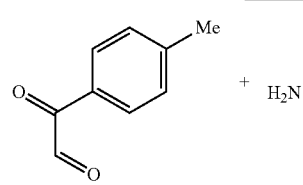
SCHEME 9D.
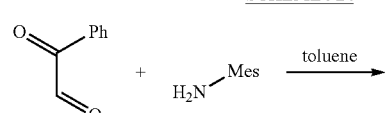
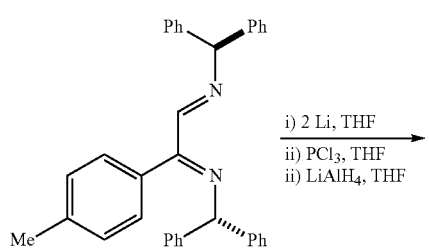
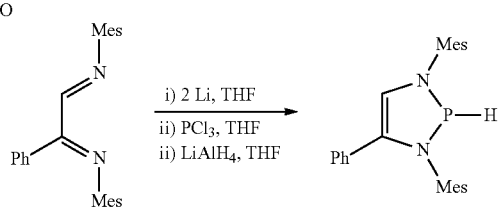
SCHEME 9E.
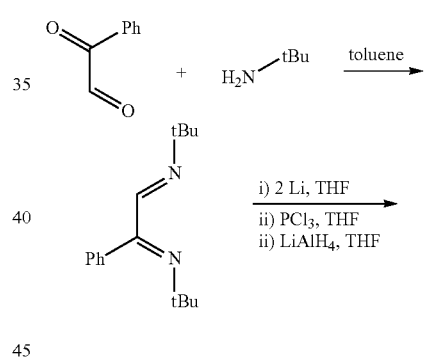
5. Route V
In one aspect, substituted chiral N-heterocyclic phosphine reagents can be prepared as shown below.
SCHEME 9C.
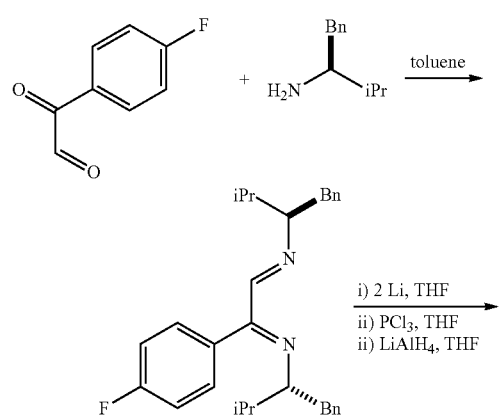
SCHEME 10A.
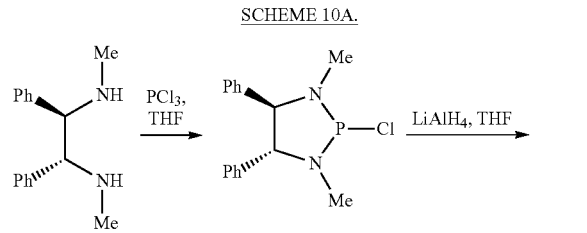
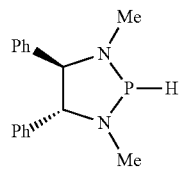

SCHEME 10B.
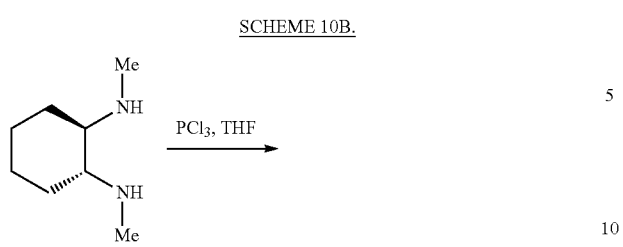
SCHEME 10C.
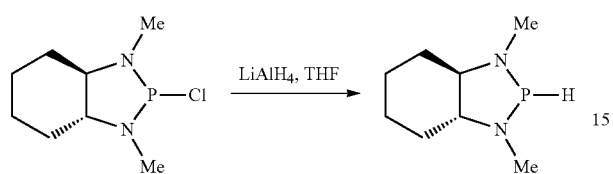
SCHEME 10D.
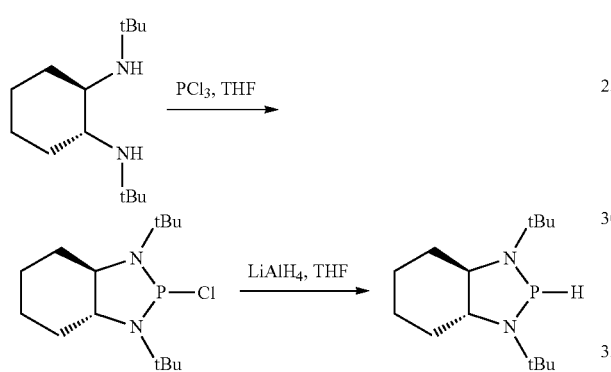
SCHEME 10E.
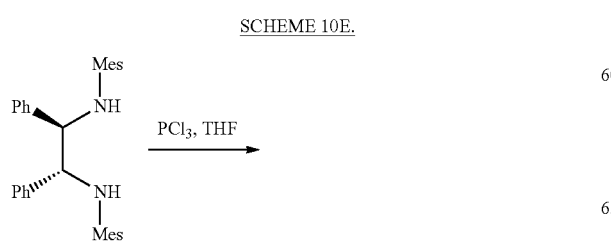
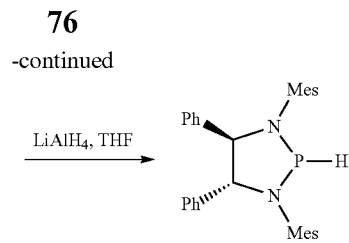
SCHEME 10F.
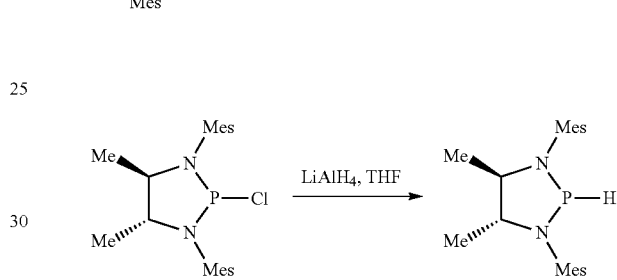
6. Route VI
In one aspect, substituted chiral N-heterocyclic phosphine reagents can be prepared as shown below.
SCHEME 11A.
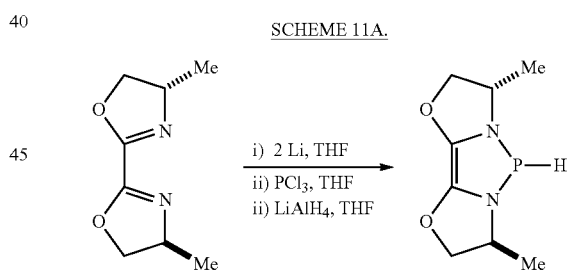
SCHEME 11B.
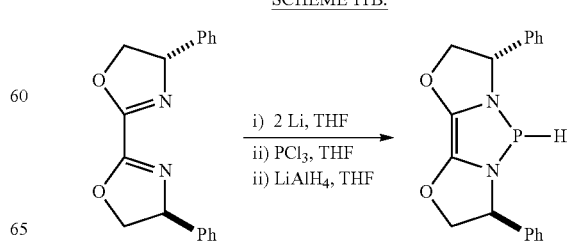

SCHEME 11C.

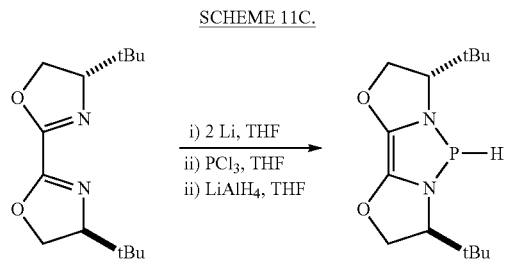 [SMILES: CC(C)(C)[C@H]1COC(C2=N[C@@H](C(C)(C)C)CO2)=N1 ; CC(C)(C)[C@H]1COC2=C3OC[C@H](C(C)(C)C)N3PN21]

SCHEME 11D.

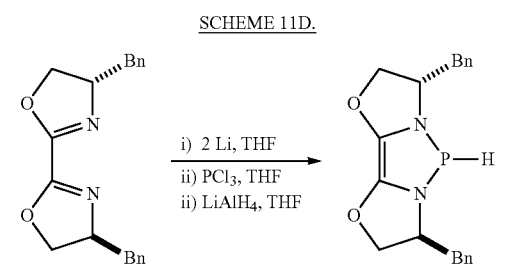 [SMILES: c1ccc(C[C@H]2COC(C3=N[C@@H](Cc4ccccc4)CO3)=N2)cc1 ; c1ccc(C[C@H]2COC3=C4OC[C@H](Cc5ccccc5)N4PN32)cc1]

SCHEME 11E.

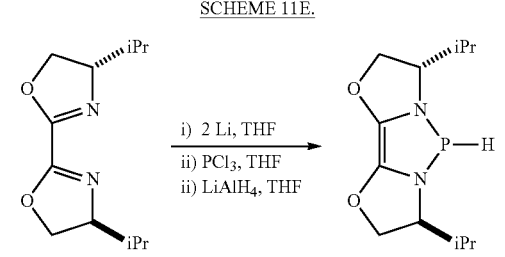 [SMILES: CC(C)[C@H]1COC(C2=N[C@@H](C(C)C)CO2)=N1 ; CC(C)[C@H]1COC2=C3OC[C@H](C(C)C)N3PN21]

7. Route VII

In one aspect, substituted chiral N-heterocyclic phosphine reagents can be prepared as shown below.

SCHEME 12A.

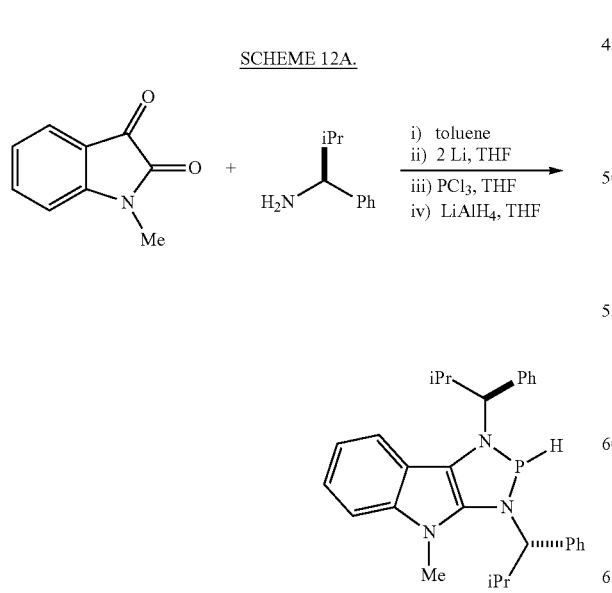

SCHEME 12B.

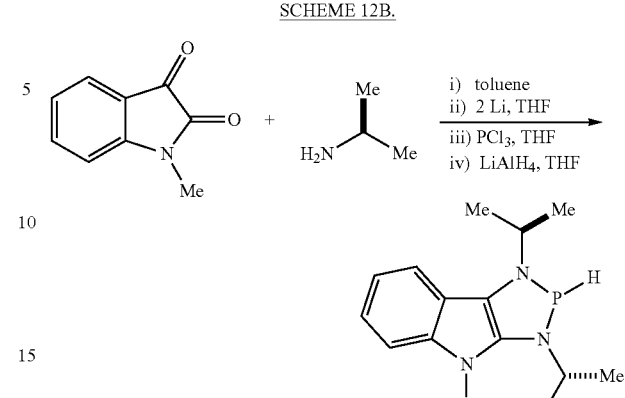

SCHEME 12C.

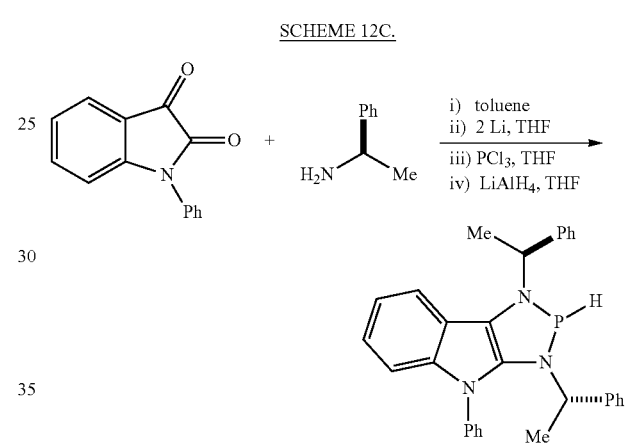

SCHEME 12D.

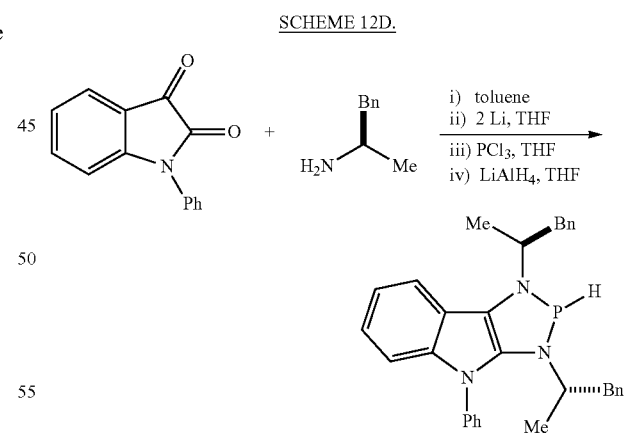

G. REPRESENTATIVE EXAMPLE OF THE UTILITY OF α-AMINOPHOSPHONATES: SYNTHESIS OF CINNARIZINE AND FLUNARIZINE

Cinnarizine is an antihistamine pharmaceutical used to treat seasickness, cerebral arteriosclerosis, and cerebral apoplexy (Towse, G. (1980) *The Journal of Laryngology &*

Otology 94(9): 1009-1015; Singh, B. N. (1986) *British Journal of Clinical Pharmacology* 21(S2): 109S-121S; Shupak et al. (1994) *Clinical Pharmacology & Therapeutics* 55(6): 670-680). Flunarizine is one of the most popular antivertiginous drugs (Rascol et al. (1989) *Fundamental &Clinical Pharmacology* 3(S1): 79s-87s; Wilder-Smith et al. (1991) *Acta Oncologica* 30(6): 731-734) and a class IV calcium antagonist for a treatment of migraine (Todd and Benfield (1989) *Drugs* 38(4): 481-499). Many synthetic approaches toward the synthesis of Cinnarizine have been reported over the past decades. These synthetic methods utilized metal reagents such as Pd (Xie et al. (2012) *Journal of the American Chemical Society* 134(51): 20613-20616; Beck et al. (2013) *RSC Advances* 3(43): 20708-20718) and Fe (Shakhmaev et al. (2015) *Russ. J. Org. Chem.* 51(1): 95-97). In pharmaceutical industries, the removal of impurities such as toxic metal catalysts is a challenging task and significantly related to the cost of drugs. In this context, transition metal-free synthetic methods are highly desirable. The synthetic method disclosed herein below for Cinnarizine and Flunarizine avoids the use of metal reagents. Without wishing to be bound by theory, this transformation can demonstrate the continued importance of NHP's in the production of pharmaceutically interesting precursors. Preliminary data for the synthesis of α-aminophosphonates provided the desired products in 78-87% yield (see Scheme 8). The Horner-Wadsworth-Emmons (HWE)-type olefination (Wadsworth, W. S. (1977) *Organic Reactions* 73-253) and the base-promoted isomerization reaction (Bartrum et al. (2013) *Tetrahedron* 69(10): 2276-2282) would complete the synthesis of Cinnarizine and Flunarizine (Scheme 15).

SCHEME 13.

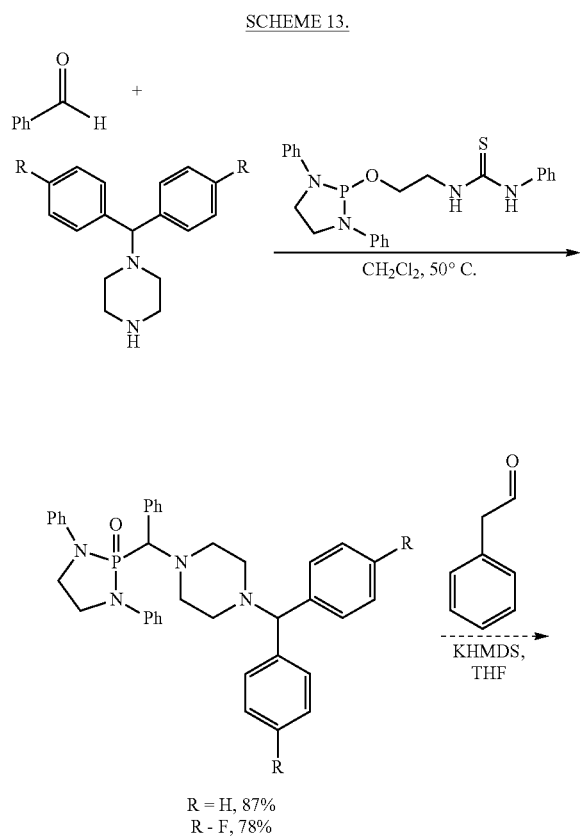

R = H, 87%
R - F, 78%

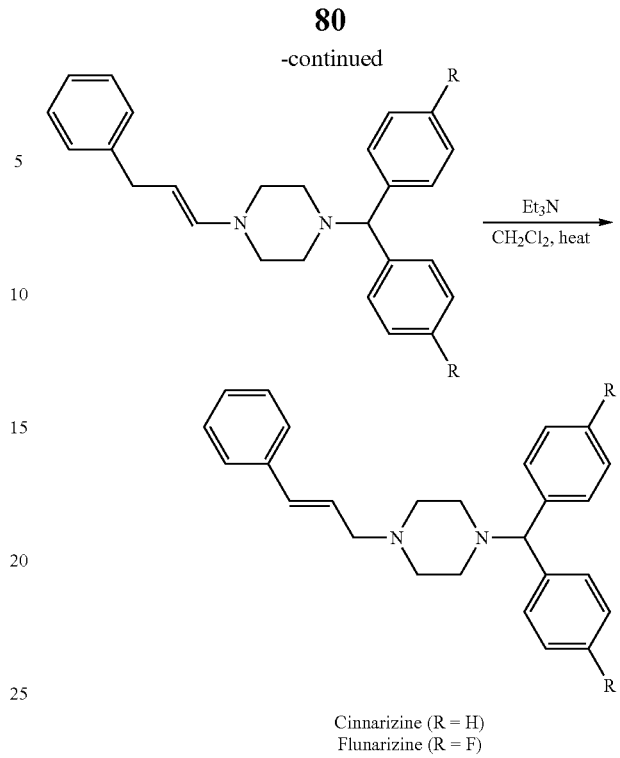

Cinnarizine (R = H)
Flunarizine (R = F)

H. PHARMACEUTICAL COMPOSITIONS AND FORMULATIONS

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including, for example, transdermal, epidermal, ophthalmic and to mucous membranes including, for example, intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial (e.g., intrathecal or intraventricular, administration). Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, and powders. Conventional pharmaceutical carriers, aqueous, powder or oily bases, thickeners, and the like may be necessary or desirable.

Also provided are pharmaceutical compositions that contain, as the active ingredient, a compound provided herein (e.g., a compound of Formula (IIa) or Formula (IIb)) or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

I. EXAMPLES

The following examples are put forth so as to provide those of ordinary skill in the art with a complete disclosure and description of how the compounds, and/or methods disclosed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Procedure for the Synthesis of α-aminophosphonates

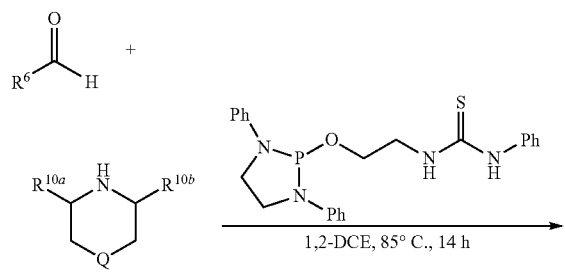

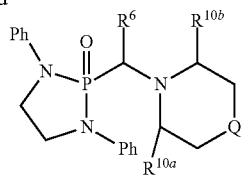

To a solution NHP-thiourea (0.1 mmol, 1.0 equiv) and aldehyde (0.2 mmol, 2.0 equiv) in 1,2-dichloroethane (0.43 mL) was added secondary amine (0.2 mmol, 2 equiv) followed by 4A molecular sieves and the mixture was stirred at 85° C. for about 14 h. The solvent was removed under vacuo to obtain crude product which was purified by column chromatography over silica gel, eluting with 25-35% EtOAc/hexanes to yield the corresponding aminophosphonates as solids.

a. Synthesis of (S)-2-(morpholino(phenyl)methyl)-1,3-diphenyl-1,3,2-diazaphospholidine 2-oxide

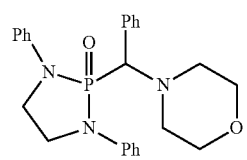

Colorless solid (39.1 mg. 0.090 mmol, 90%). mp: 209-210° C. IR (Neat, cm$^{-1}$): 3059, 2962, 2852, 1599, 1498, 1273, 1129, 1033; $^1$H NMR (400 MHz CDCl$_3$): δ 7.54 (d, J=8.6 Hz, 2H), 7.36 (q, J=7.4 Hz, 4H), 7.25-7.16 (m, 5H), 7.07 (q, J=7.6 Hz, 2H), 6.90 (d, J=7.4 Hz, 2H), 4.07 (d, J=9.2 Hz, 1H), 3.69-3.59 (m, 5H), 3.27 (dq, J=8.6, 2.5 Hz, 1H), 3.03-2.95 (m, 3H), 2.49-2.44 (m, 2H), 2.19 (dq, J=8.4, 2.1 Hz, 1H); $^{13}$C NMR (100 MHz, CDCl$_3$): δ 142.1 (dd, J=38.1, 7.5 Hz), 134.3 (d, J=5.9 Hz), 130.3 (d, J=7.5 Hz), 129.4 (d, J=30.7 Hz), 128.3 (d, J=3.0 Hz), 128.1 (d, J=2.2 Hz), 122.3 (d, J=47.6 Hz), 117.8 (dd, J=198.9, 3.7 Hz), 72.1 (d, J=129.0 Hz), 67.4, 53.9 (d, J=8.2 Hz), 43.4 (dd, J=57.6, 6.7 Hz); $^{31}$P NMR (162 MHz CDCl$_3$): δ 25.03 ppm; HRMS (ESI) calcd for C$_{25}$H$_{28}$N$_3$O$_2$P [M+Na]$^+$: 456.1811; found: 456.1810.

b. Synthesis of (S)-2-(morpholino(4-(trifluoromethyl)phenyl)methyl)-1,3-diphenyl-1,3,2-diazaphospholidine 2-oxide

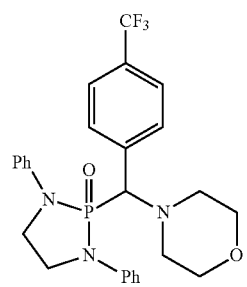

Colorless solid (41.7 mg, 0.083 mmol, 83%). mp: 202-204° C. IR (Neat, cm$^{-1}$): 3059, 2960, 2858, 1599, 1504, 1269, 1166, 1033; $^1$H NMR (400 MHz, CDCl$_3$): δ 7.50-7.43

(m, 4H), 7.39-7.34 (m, 4H), 7.24 (d, J=8.2 Hz, 2H), 7.12-7.06 (m, 4H), 4.15 (d, J=10.9, Hz, 1H), 3.72-3.57 (m, 5H), 3.36 (dq, J=8.8, 3.1 Hz, 1H), 1H), 3.12-2.94 (m, 3H), 2.47-2.42 (m, 2H), 2.36 (dq, J=8.4, 3.1 Hz, 1H); $^{13}$C NMR (100 MHz, CDCl$_3$): δ 141.8 (dd, J=45.6, 7.5 Hz), 138.6 (d, J=4.5 Hz), 130.6 (d, J=6.7 Hz), 130.3 (d, J=3.0 Hz), 129.5 (d, J=34.4 Hz), 125.3, 124.9 (t, J=3.7 Hz), 122.8 (d, J=55.3 Hz), 118.1 (dd, J=219, 4.5 Hz), 71.8 (d, J=128.6 Hz), 67.2, 53.8 (d, J–8.2 Hz), 43.9 (dd, J–56.8, 7.5 Hz); $^{31}$P NMR (162 MHz, CDCl$_3$): δ 24.86 ppm (d, J=1.9 Hz); HRMS (ESI) calcd for C$_{26}$H$_{27}$F$_3$N$_3$O$_2$P [M+Na]$^+$: 524.1685; found 524.1702.

c. Synthesis of (S)-2-((4-chlorophenyl)(morpholino)methyl)-1,3-diphenyl-1,3,2-diazaphospholidine 2-oxide

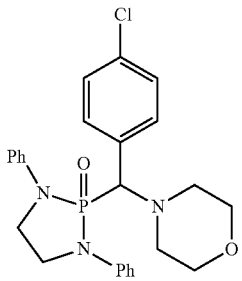

Off-white solid (40.2, 0.086 mmol, 86%). mp: 185-186° C. IR (Neat, cm$^{-1}$): 3057, 2958, 2852, 1599, 1494, 1269, 1116, 1033, $^1$H NMR (400 MHz, CDCl$_3$): δ 7.51 (app d, J=8.6 Hz 2H) 6.87-6.83 (m, 2H), 7.39-7.33 (m, 4H), 7.23 (d, J=8.2 Hz, 2H), 7.16 (d, J=8.4 Hz, 2H) 7.09 (q, J=7.4 Hz, 2H), 4.05 (d, J=9.9 Hz, 1H), 3.73-3.57 (m, 5H), 3.35 (dq, J 9.0, 2.3 Hz, 1H), 3.12-2.94 (m, 3H), 2.46-2.40 (m, 2H), 2.35 (dq, J=8.4, 2.7 Hz, 1H); $^{13}$C NMR (100 MHz, CDCl$_3$): δ 141.8 (dd, J=41.9, 7.5 Hz), 134.1 (d, J=3.7 Hz), 132.9 (d, J=5.2 Hz), 131.5 (d, J=6.2 Hz), 129.4 (d, J=31.7 Hz), 128.3 (d, J=2.2 Hz), 122.4 (d, J 47.1 Hz), 117.9 (dd, J=207.1, 3.7 Hz), 71.4 (d, J=128.6 Hz), 67.3, 53.9 (d, J=8.2 Hz), 43.7 (dd, J=47.9, 7.5 Hz); $^{31}$P NMR (162 MHz, CDCl$_3$): δ 25.80 ppm; HRMS (ESI) calcd for C$_{26}$H$_{27}$ClN$_3$O$_2$P [M+Na]$^+$: 490.1422; found: 490.1424.

d. Synthesis of (S)-2-((4-bromophenyl)(morpholino)methyl)-1,3-diphenyl-1,3,2-diazaphospholidine 2-oxide

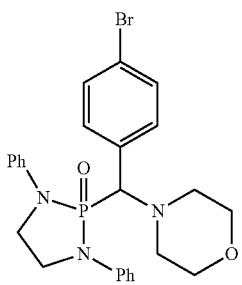 [SMILES: O=P1(C(c2ccc(Br)cc2)N2CCOCC2)N(c2ccccc2)CCN1c1ccccc1]

Pale brown solid (46.4, 0.091 mmol, 91%). mp: 169-172° C. IR (Neat, cm$^{-1}$): 3057, 2852, 1599, 1504, 1269, 1163, 1008; $^1$H NMR (400 MHz, CDCl$_3$): δ 7.50 (d, J=8.0 Hz, 2H), 7.38-7.31 (m, 6H), 7.22 (d, J=8.0 Hz, 2H), 7.08 (q, J=7.8 Hz, 2H), 6.79 (d, J=8.2 Hz, 2H), 4.04 (d, J=9.9 Hz, 1H), 3.72-3.57 (m, 5H), 3.34 (q, J=11.1, 2.5 Hz, 1H), 3.11-2.99 (m, 3H), 2.44-2.32 (m, 3H); $^{13}$C NMR (100 MHz, CDCl$_3$): δ 141.8 (dd, J=41.4, 7.5 Hz), 133.4 (d, J=5.4 Hz), 133.4 (d, J=5.4 Hz), 131.8 (d, J=6.7 Hz), 131.2 (d, J=2.2 Hz), 129.4 (d, J=32.2 Hz), 122.6 (d, J=46.4 Hz), 122.3 (d, J=4.5 Hz), 117.9 (dd, J=206.4, 3.7 Hz), 71.4 (d, J=128.6 Hz), 67.2, 53.8 (d, J=7.5 Hz), 43.6 (dd, J=46.4, 6.7 Hz); $^{31}$P NMR (162 MHz, CDCl$_3$): δ 25.64 ppm; HRMS (ESI) calcd for C$_{26}$H$_{27}$BrN$_3$O$_2$P [M+Na]$^+$: 534.0916; found: 534.0925.

e. Synthesis of (S)-2-((2,4-dichlorophenyl)(morpholino)methyl)-1,3-diphenyl-1,3,2-diazaphospholidine 2-oxide

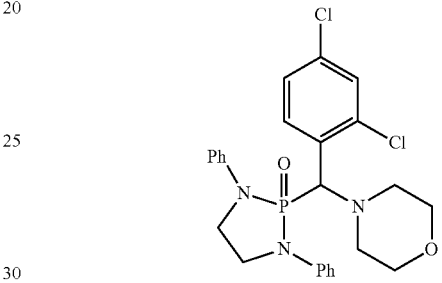

Colorless solid (43.8 mg, 0.087 mmol, 87%). mp: 168-170° C. IR (Neat, cm$^{-1}$): 3072, 2968, 2852, 1599, 1502, 1269, 1114, 1033; $^1$H NMR (400 MHz, CDCl$_3$): δ 7.42-7.31 (m, 5H), 7.26-7.16 (m, 5H), 7.07 (t, J 7.2 Hz, 1H), 7.00-6.95 (m, 2H), 4.78 (d, J 17.8, Hz, 1H), 3.72-3.58 (m, 3H), 3.47-3.38 (m, 5H), 2.66-2.57 (m, 4H); $^{13}$C NMR (100 MHz, CDCl$_3$): δ 142.1 (dd, J 101.7, 6.7 Hz), 136.4 (d, J 11.9 Hz), 134.5 (d, J 3.0 Hz), 133.5 (d, J=4.5 Hz), 129.4, 129.2 (d, J=28.4 Hz), 129.0 (d, J=3.0 Hz), 126.4 (d, J=1.5 Hz), 122.9 (d, J=6.0 Hz), 118.9 (dd, J=52.4, 3.7 Hz), 67.1, 65.7 (d, J=136.1 Hz), 52.4 (d, J 8.2 Hz), 44.2 (dd, J=13.5, 8.2 HZ); $^{31}$P NMR (162 MHz, CDCl$_3$): δ 23.80 ppm; HRMS (ESI) calcd for C$_{25}$H$_{26}$Cl$_2$N$_3$O$_2$P [M+Na]$^+$: 524.1032; found: 524.1032.

f. Synthesis of (S)-2-((2-bromo-4-methylphenyl)(morpholino)methyl)-1,3-diphenyl-1,3,2-diazaphospholidine 2-oxide

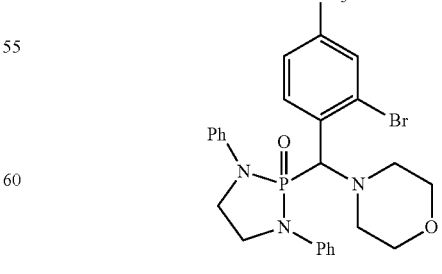

Colorless solid (48.9 mg, 0.093 mmol, 93%). mp: 169-171° C. IR (Neat, cm$^{-1}$): 3059, 2957, 2854, 1599, 1494, 1269, 1116, 1037; $^1$H NMR (400 MHz, CDCl$_3$): δ 7.39 (d, J=7.8 Hz, 2H), 7.34-7.25 (m, 5H), 7.21-7.16 (m, 3H), 7.05 (t, J=8.2 Hz, 1H), 6.94 (t, J=7.2 Hz, 1H), 6.83 (d, J=8.0 Hz, 1H), 4.85 (d, J=18.1 Hz, 1H), 3.71-3.54 (m, 3H), 3.48 (t, J 8.8, Hz, 4H), 3.47-3.27 (m, 1H), 2.65 (bs, 4H), 2.20 (s, 3H); $^{13}$C NMR (100 MHz, CDCl$_3$): δ 142.3 (dd, J=95.7, 6.7 Hz), 139.8 (d, J=2.2 Hz), 133.5, 132.5 (d, J=4.5 Hz), 129.1 (d, J 32.9 Hz), 128.8 (d, J=3.0 Hz), 127.5 (d, J=2.0 Hz), 126.9 (d, J=11.9 Hz), 122.5 (d, J 13.5 Hz), 118.5 9 (dd, J=50.1, 3.7 Hz), 69.2 (d, J=216.0 Hz), 67.2, 52.4 (d, J=8.9 Hz), 44.0 (dd, J=21.7, 8.2 Hz), 20.7; $^{31}$P NMR (162 MHz CDCl$_3$): δ 25.00 ppm; HRMS (ESI) calcd for C$_{26}$H$_{29}$BrN$_3$O$_2$P [M+Na]$^+$: found: 548.1070.

g. Synthesis of (S)-2-(morpholino(thiophen-2-yl)methyl)-1,3-diphenyl-1,3,2-diazaphospholidine 2-oxide

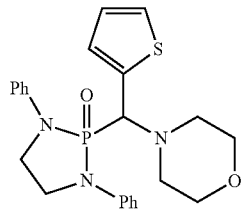

Colorless solid (30.3 mg, 0.069 mmol, 69%. mp: 207-209° C. IR (Neat, cm$^{-1}$): 3059, 2918, 2848, 1599, 1496, 1273, 1112, 1033; $^1$H NMR (400 MHz CDCl$_3$): δ 7.50 (d, J 7.6 Hz, 2H), 7.36-7.26 (m, 6H), 7.19 (d, J=5.1 Hz, 1H), 7.07 (t, J=7.2 Hz, 2H), 6.86 (d, J=4.5 Hz, 1H), 6.58 (bs, 1H), 4.38 (d, J=15.1 Hz, 1H), 3.79 (m, 1H), 3.59-3.43 (m, 6H), 2.91-2.84 (m, 1H), 2.70 (bs, 2H) 2.54-2.49 (m. 2H): $^{13}$C NMR (100 MHz, CDCl$_3$): δ 142.0 (dd, J=62.1, 7.5 Hz), 135.3 (d, J=1.5 Hz), 129.3 (d, J=26.2 Hz), 128.9 (d, J=8.2 Hz), 126.6 (d, J=2.2 Hz), 126.2 (d, J=3.0 Hz), 122.8 (d, J=57.6 Hz), 118.7 (dd, J=223.6, 3.6 Hz), 67.2, 66.1 (d, J=136.1 Hz), 52.9 (d, J=7.5 Hz), 44.4 (dd, J=94.2, 6.7 Hz), $^{31}$P NMR (162 MHz, CDCl$_3$): δ 24.71 ppm; HRMS (ESI) calcd for C$_{23}$H$_{26}$N$_3$O$_2$PS [M+Na]$^+$: 462.1376; found: 462.1378.

h. Synthesis of (S)-2-(1-morpholinobutyl)-1,3-diphenyl-1,3,2-diazaphospholidine 2-oxide

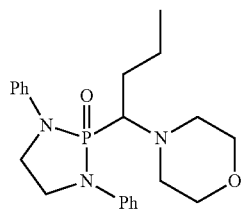

Off-white solid (25.0 mg, 0.063 mmol, 63%), mp: 165-167° C. IR (Neat, cm$^{-1}$): 3059, 2957, 2870, 1599, 1502, 1271, 1116, 1033; $^1$H NMR (400 MHz, CDCl$_3$): δ 7.34-7.29 (m, 8H), 7.03-7.00 (m, 2H), 4.10-4.03 (m, 1H), 3.84-3.80 (m, 3H), 3.53-3.46 (m, 4H), 3.25-2.17 (m, 1H), 2.54-2.52 (m, 2H), 2.19-2.17 (m, 2H), 2.02-1.93 (m, 1H), 1.85-1.71 (m, 1H), 1.56-1.26 (m, 2H), 0.88 (t, J=6.1 Hz, 3H); $^{13}$C NMR (100 MHz, CDCl$_3$): δ 142.8 (dd, J=34.4, 8.2 Hz), 129.5 (d, J=3.0 Hz), 122.1 (d, J=12.7 Hz), 117.0 (dd, J=29.9, 4.5 Hz), 67.7, 63.6 (d, J=129.0 Hz), 51.0, 44.3 (dd, J=83.8, 5.9 Hz), 28.9 (d, J=5.9 Hz), 23.2 (d, J=17.2 Hz), 13.9 (d, J=1.5 Hz); $^{31}$P NMR (162 MHz, CDCl$_3$): δ 32.52 ppm; HRMS (ESI) calcd for C$_{22}$H$_{30}$N$_3$O$_2$P [M+Na]$^1$: found 422.1975.

i. Synthesis of (S)-2-((2-fluorophenyl)(morpholino)methyl)-1,3-diphenyl-1,3,2-diazaphospholidine 2-oxide

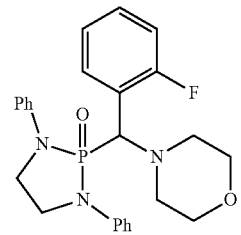 [SMILES: O=P1(C(c2ccccc2F)N2CCOCC2)N(c2ccccc2)CCN1c1ccccc1]

Colorless solid (39.8 mg, 0.088 mmol, 88%). mp: 178-179° C. IR (Neat, cm$^{-1}$): 3055, 2966, 2854, 1600, 1494, 1269, 1114, 1033; $^1$H NMR (400 MHz, CDCl$_3$): δ 7.37-7.23 (m, 9H), 7.19-7.13 (m, 1H), 7.09-7.05 (m, 1H), 7.00 (t, J=7.2 Hz, 1H), 6.94-6.87 (m, 2H), 4.57 (d, J=16.0 Hz, 1H) 3.71 (quint, J=8.0 Hz, 1H), 3.58-3.41 (m, 6H), 3.15-3.08 (m, 1H), 2.62-2.53 (m, 4H); $^{13}$C NMR (100 MHz, CDCl$_3$): δ 161.3 (dd, J=247.6, 9.7 Hz), 142.4 (dd, J=68.8, 7.5 Hz), 132.4 (dd, J=4.5, 3.0 Hz), 129.8 (dd, J=8.2, 2.2 Hz), 129.2 (d, J=17.9 Hz), 123.5 (dd, J=3.7, 2.2 Hz), 122.7 (d, J=10.5 Hz), 120.0 (d, J=14.9 Hz), 118.5 (dd, J=84.5, 3.7 Hz), 115.4 (d, J=23.2 Hz), 67.2, 62.5 (d, J=136.9 Hz), 52.8 (d, J=7.5 Hz), 44.1 (dd, J=17.2, 7.5 Hz); $^{31}$P NMR (162 MHz, CDCl$_3$): δ 25.14 ppm (d, J=7.1 Hz); HRMS (ESI) calcd for C$_{25}$H$_{27}$FN$_3$O$_2$P [M+Na]$^+$: found: 474.1720.

j. Synthesis of (S)-2-((4-fluorophenyl)(morpholino)methyl)-1,3-diphenyl-1,3,2-diazaphospholidine 2-oxide

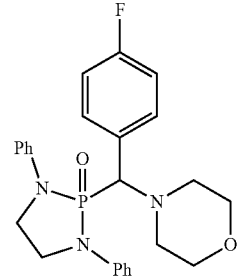 [SMILES: O=P1(C(c2ccc(F)cc2)N2CCOCC2)N(c2ccccc2)CCN1c1ccccc1]

Colorless solid (39.1 mg, 0.087 mmol, 87%). mp: 194-196° C. IR (Neat, cm$^{-1}$): 3059, 2976, 2854, 1600, 1504, 1273, 1114, 1033; $^1$H NMR (400 MHz, CDCl$_3$): δ 7.51 (d, J=8.0 Hz, 2H), 7.38-7.33 (m, 4H), 7.22 (d, J=8.0 Hz, 2H), 7.08 (q, J=7.2 Hz, 2H), 6.88 (d, J=7.2 Hz, 4H), 4.05 (d, J=9.8 Hz, 1H), 3.72-3.58 (m, 5H), 3.33 (q, J=8.6 Hz, 1H), 3.11-2.98 (m, 1H), 2.46-2.30 (m, 3H); $^{13}$C NMR (100 MHz, CDCl$_3$): δ 162.5 (dd, J=248.3, 3.0 Hz), 142.4 (dd, J=42.6, 7.5 Hz), 131.8 (t, J=7.5 Hz), 130.1 (t, J=3.0 Hz), 129.3 (d, J=30.7 Hz), 122.5 (d, J=44.9 Hz), 117.9 (dd, J=203.4, 3.7

Hz), 115.1 (dd, J=21.7, 2.2 Hz), 71.2 (d, J=129.4 Hz), 67.3, 53.8 (d, J=8.2 Hz), 43.6 (dd, J=51.6, 7.5 Hz); $^{31}$P NMR (162 MHz, CDCl$_3$): δ 26.33 ppm (d, J=4.9 Hz); HRMS (ESI) calcd for C$_{25}$H$_{27}$FN3O$_2$P [M+Na]$^+$: 474.1717; found: 474.1718.

k. Synthesis of (S)-2-(morpholino(p-tolyl)methyl)-1,3-diphenyl-1,3,2-diazaphospholidine 2-oxide

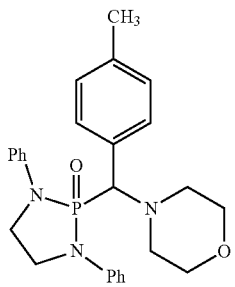 [SMILES: Cc1ccc(C(N2CCOCC2)P2(=O)N(c3ccccc3)CCN2c2ccccc2)cc1]

Off-white solid (37.2 mg, 0.083 mmol, 83%). mp: 189-190° C. IR (Neat, cm$^{-1}$): 3055, 2957, 2850, 1599, 1496, 1271, 1116, 1033; $^1$H NMR (400 MHz, CDCl$_3$): δ 7.54 (d, J=8.0 Hz, 2H), 7.36 (q, J=7.4 Hz, 4H), 7.22 (d, J=8.0 Hz, 2H), 7.08 (q, J=7.2 Hz, 2H), 6.98 (d, J=7.8 Hz, 2H), 6.78 (d, J=6.3 Hz, 2H), 4.03 (d, J=9.2 Hz, 1H), 3.69-3.60 (m, 5H), 3.27 (q, J=10.8 Hz, 1H), 3.05-2.96 (m, 3H), 2.48-2.42 (m, 2H), 2.29 (s, 3H), 2.21 (q, J=7.2 Hz, 1H); $^{13}$C NMR (100 MHz, CDCl$_3$): δ 142.1 (dd, J=38.1, 7.5 Hz), 138.1 (d, J=3.7 Hz), 131.1 (d, J=5.2 Hz), 130.2 (d, J=7.5 Hz), 129.3 (d, J=29.9 Hz), 128.8 (d, J=3.0 Hz), 122.2 (d, J=31.4 Hz), 117.7 (dd, J=178.0, 4.5 Hz), 72.2 (d, J=129.4 Hz), 67.4, 53.9 (d, J=8.2 Hz), 43.4 (dd, J=41.4, 6.7 Hz), 21.3; $^{31}$P NMR (162 MHz, CDCl$_3$): δ 27.14 ppm; HRMS (ESI) calcd for C$_{26}$H$_{30}$N$_3$O$_2$P [M+Na]$^+$: 470.1968; found: 470.1964.

l. Synthesis of (S)-2-(morpholino(o-tolyl)methyl)-1,3-diphenyl-1,3,2-diazaphospholidine 2-oxide

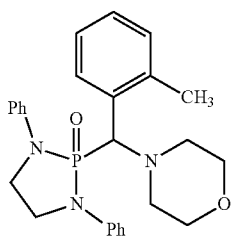 [SMILES: Cc1ccccc1C(N1CCOCC1)P1(=O)N(c2ccccc2)CCN1c1ccccc1]

Off-white solid (35.3 mg, 0.079 mmol, 79%). mp: 199-201° C. IR (Neat, cm$^{-1}$): 3057, 2957, 2850, 1599, 1494, 1271, 1116, 1033; $^1$H NMR (400 MHz, CDCl$_3$): δ 7.57 (d, J=8.2 Hz, 2H), 7.39-7.28 (m, 5H), 7.19 (d, J=8.2 Hz, 2H), 7.14-7.01 (m, 5H), 4.44 (d, J=10.6 Hz, 1H), 3.75-3.55 (m, 5H), 3.34-3.01 (m, 4H), 2.48-2.44 (m, 2H), 2.31 (q, J=8.2 Hz, 1H), 1.59 (s, 3H); $^{13}$C NMR (100 MHz, CDCl$_3$): δ 142.3 (dd, J=58.3, 7.5 Hz), 138.4 (d, J=8.9 Hz), 132.0 (d, J=3.7 Hz), 130.8 (d, J=1.5 Hz), 130.7, 128.7 (d, J=36.6 Hz), 127.8 (d, J=2.2 Hz), 125.3 (d, J=3.0 Hz), 122.3 (d, J=36.6 Hz), 117.8 (dd, J=205.7, 3.7 Hz), 67.4, 53.7 (d, J=8.9 Hz), 43.9 (d, J=7.5 Hz), 43.2 (d, J=6.7 Hz), 19.6; $^{31}$P NMR (162 MHz, CDCl$_3$): δ 27.72 ppm; HRMS (ESI) calcd for C$_{26}$H$_{30}$N$_3$O$_2$P [M+Na: 470.1968; found: 470.1973.

m. Synthesis of (S)-2-((4-methoxyphenyl)(morpholino)methyl)-1,3-diphenyl-1,3,2-diazaphospholidine 2-oxide

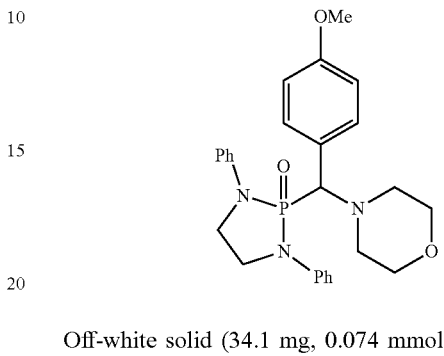

Off-white solid (34.1 mg, 0.074 mmol, 74%). mp: 178-180° C. IR (Neat, cm$^{-1}$): 3059, 2960, 2854, 1600, 1504, 1271, 1116, 1033; $^1$H NMR (400 MHz, CDCl$_3$): δ 7.54 (d, J=7.8 Hz, 2H), 7.39-7.33 (m, 4H), 7.22 (d, J=8.4 Hz, 2H), 7.08 (q, J=7.2 Hz, 2H), 6.83-6.79 (m, 2H), 6.71 (d, J=2.7 Hz, 2H), 4.02 (d, J=8.8 Hz, 1H), 3.77 (s, 3H), 3.73-3.61 (m, 5H), 3.31 (dq, J=8.6, 2.5 Hz, 1H), 3.09-3.02 (m, 3H), 2.47-2.42 (m, 2H), 2.30 (dq, J=8.6, 2.5 Hz, 1H); $^{13}$C NMR (100 MHz, CDCl$_3$): δ 159.5 (d, J=2.2 Hz), 142.2 (dd, J=40.4, 7.5 Hz), 131.5 (d, J=6.7 Hz), 129.3 (d, J=29.9 Hz), 126.2 (d, J=5.2 Hz), 122.3 (d, J=32.9 Hz), 117.8 (dd, J=180.3, 4.5 Hz), 113.5 (d, J=2.2 Hz), 71.3 (d, J=130.1 Hz), 67.4, 55.4, 53.8 (d, J=8.2 Hz), 43.6 (dd, J=37.4, 6.7 Hz); $^{31}$P NMR (162 MHz, CDCl$_3$): δ 27.40 ppm; HRMS (ESI) calcd for C$_{26}$H$_{30}$N$_3$O$_3$P [M+Na]$^+$486.1917; found: 486.1925.

n. Synthesis of (S)-2-((2-bromo-4-chlorophenyl)(morpholino)methyl)-1,3-diphenyl-1,3,2-diazaphospholidine 2-oxide

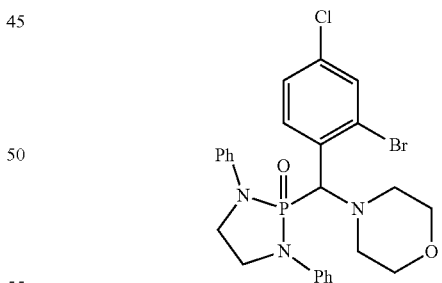

Off-white solid (45.4 mg, 0.083 mmol, 83%). mp: 176-178° C. IR (Neat, cm$^{-1}$): 3061, 2962, 2854, 1599, 1504, 1267, 1116, 1035; $^1$H NMR (400 MHz, CDCl$_3$): δ 7.43-7.31 (m, 6H), 7.22 (d, J=7.8 Hz, 2H), 7.16 (t, J=8.6 Hz, 2H), 7.07 (t, J=6.3 Hz, 1H), 7.02-6.93 (m, 2H), 4.80 (d, J=18.2 Hz, 1H), 3.72-3.62 (m, 3H), 3.48-3.41 (m, 5H), 2.69-2.56 (m, 4H); $^{13}$C NMR (100 MHz, CDCl$_3$): δ 142.4 (dd, J=108.4, 6.7 Hz), 134.6 (d, J=2.2 Hz), 133.5 (d, J=3.7 Hz), 132.5, 130.6 (d, J=3.7 Hz), 129.2 (d, J=29.9 Hz), 127.2 (d, J=11.9 Hz), 126.9 (d, J=2.2 Hz), 122.9, 118.9 (dd, J=40.4, 3.7 Hz), 68.5 (d, J=135.4 Hz), 67.1, 52.2 (d, J=7.5 Hz), 44.2 (dd, J=17.2, 9.0 Hz); $^{31}$P NMR (162 MHz, CDCl$_3$): δ 23.68 ppm; HRMS (ESI) calcd for C$_{25}$H$_{26}$BrClN$_3$O$_2$P [M+Na]$^+$: 568.0527; found: 568.0534.

o. Synthesis of (S)-2-(furan-2-yl(morpholino)methyl)-1,3-diphenyl-1,3,2-diazaphospholidine 2-oxide

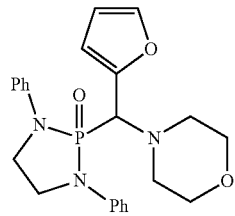 [SMILES: O=P1(C(c2ccco2)N2CCOCC2)N(c2ccccc2)CCN1c1ccccc1]

Pale brown solid (14.1 mg, 0.033 mmol, 33 o/o). mp: 180-183° C. IR (Neat, cm$^{-1}$): 3059, 2958, 2854, 1599, 1496, 1273, 1112, 1033; $^1$H NMR (400 MHz, CDCl$_3$): δ 7.44-7.41 (m, 2H), 7.37-7.30 (m, 6H), 7.24-7.23 (m, 1H), 7.09-7.03 (m, 2H), 6.24 (q, J=1.4 Hz, 1H), 6.06 (q, J=1.4 Hz, 1H), 4.23 (d, J=20.5 Hz, 1H), 3.82-3.66 (m, 3H), 3.56-3.47 (m, 5H), 2.57-2.52 (m, 2H), 2.34-2.29 (m, 2H); $^{13}$C NMR (100 MHz, CDCl$_3$): δ 147.6 (d, J=2.2 Hz), 142.7 (d, J=2.2 Hz), 142.2 (dd, J=7.5 Hz), 129.3 (d, J=3.0 Hz), 122.7 (d, J=8.9 Hz), 118.5 (dd, J=13.5, 4.5 Hz), 122.9, 111.9 (d, J=7.5 Hz), 110.6 (d, J=135.4 Hz), 67.3, 63.3 (d, J=139.1 Hz), 52.4 (d, J=6.7 Hz), 44.1 (d, J=7.5 Hz); $^{31}$P NMR (162 MHz, CDCl$_3$): δ 24.29 ppm; HRMS (ESI) calcd for C$_{23}$H$_{26}$N$_3$O$_3$P [M+Na]$^+$: 446.1604; found: 446.1603.

p. Synthesis of (S)-2-((4-methylpiperazin-1-yl)phenyl)methyl)-1,3-diphenyl-1,3,2-diazaphospholidine 2-oxide

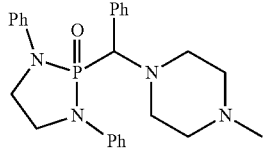

Off-white solid (25.9 mg, 0.059 mmol, 59%). mp: 175-177° C. IR (Neat, cm$^{-1}$): 3059, 2933, 2839, 1599, 1494, 1269, 1126, 1035; $^1$NMR (400 MHz, CDCl$_3$): δ 7.52-7.49 (m, 2H), 7.38-7.33 (m, 4H), 7.24-7.16 (m, 5H), 7.10-7.05 (m, 2H), 6.90-6.88 (m, 2H), 4.10 (d, J=9.8 Hz, 1H), 3.65 (dq, J=8.2, 2.7 Hz, 1H), 3.29 (dq, J=8.6, 2.7 Hz, 1H), 3.01 (dq, J=8.4, 2.7 Hz, 1H), 2.58-2.56 (m, 7H), 2.35 (s, 3H), 2.23 (dq, J=8.4, 2.5 Hz, 2H); $^{13}$C NMR (100 MHz, CDCl$_3$): δ 142.1 (dd, J=24.7, 7.5 Hz), 134.4 (d1J=4.5 Hz), 130.2 (d, J=6.7 Hz), 129.4 (d, J=34.4 Hz), 128.4 (d, J=3.0 Hz), 128.1 (d, J=2.2 Hz), 122.3 (d, J=27.7 Hz), 117.8 (dd, J=185.5, 4.5 Hz), 72.0 (d, J=129.4 Hz), 55.2, 52.1, 45.3, 43.4 (dd, J=57.8, 6.7 Hz); $^{31}$P NMR (162 MHz, CDCl$_3$): δ 25.11 ppm; HRMS (ESI) calcd for C$_{26}$H$_{31}$N$_4$OP [M+Na]$^+$: 469.2128; found: 469.2126.

q. Synthesis of (S)-2-((4-cyclohexylpiperazin-1-yl)(phenyl)methyl)-1,3-diphenyl-1,3,2-diazaphospholidine 2-oxide Off-white solid (35.2 mg, 0.068 mmol, 68%). mp: 180-182° C. IR (Neat, cm$^{-1}$): 3059, 2931, 2856, 1599, 1494, 1269, 1124, 1035; $^1$H NMR (400 MHz, CDCl$_3$): δ 7.48 (d, J=8.4 Hz, 2H), 7.37-7.31 (m, 4H), 7.25-7.16 (m, 5H), 7.08 (t, J=7.4 Hz, 2H), 6.86 (d, J=7.6 Hz, 2H), 4.16 (d, J=9.4 Hz, 1H), 3.62 (dq, J=7.8, 2.7 Hz, 1H), 3.30 (dq, J=8.6, 2.7 Hz, 1H), 3.03-2.66 (m, 8H), 2.27 (dq, J=8.4, 2.5 Hz, 1H), 2.05 (d, J=10.4 Hz, 2H), 1.85 (d, J=12.9 Hz, 2H), 1.67 (d, J=12.7 Hz, 2H), 1.39-1.08 (m, 6H); $^{13}$C NMR (100 MHz, CDCl$_3$): δ 142.0 (dd, J=11.9, 8.2 Hz), 133.8 (d, J=5.2 Hz), 130.1 (d, J=6.7 Hz), 129.4 (d, J=48.6 Hz), 128.5 (d, J=3.0 Hz), 128.2 (d, J=2.2 Hz), 122.4 (d, J=11.9 Hz), 117.7 (dd, J=189.9, 3.7 Hz), 70.9 (d, J=130.2 Hz), 64.7, 50.8, 49.0, 43.5 (dd, J=72.5, 6.7 Hz), 27.6, 25.4, 25.3; $^{31}$P NMR (162 MHz, CDCl$_3$): δ 26.29 ppm; HRMS (ESI) calcd for C$_{31}$H$_{39}$N4OP [M+Na]$^+$: 515.2934; found: 515.2951.

r. Synthesis of (S)-2-((4-benzhydrylpiperazin-1-yl)(phenyl)methyl)-1,3-diphenyl-1,3,2-diazaphospholidine 2-oxide Colorless solid (52.1 mg, 0.052 mmol, 87%). mp: 176-178° C. IR (Neat, cm$^{-1}$): 3059, 2962, 2808, 1599, 1494, 1269, 1128, 1033; $^1$H NMR (400 MHz, CDCl$_3$): δ 7.47 (d, J=7.8 Hz, 2H), 7.38 (d, J=7.8 Hz, 2H), 7.37-7.29 (m, 6H), 7.24-7.02 (m, 13H), 6.87 (d, J=6.3 Hz, 2H), 4.14 (s, 1H), 4.10 (d, J=11.3 Hz, 1H), 3.64 (dq, J=7.8, 2.9 Hz, 1H), 3.28 (dq, J=8.6, 2.7 Hz, 1H), 3.07 (dq, J=8.7, 3.0 Hz, 1H), 2.51-2.31 (m, 9H); $^{13}$C NMR (100 MHz, CDCl$_3$): δ 142.8 (d, J=3.7 Hz), 142.2 (dd, J=53.1, 7.5 Hz), 134.4 (d, J=3.7 Hz), 130.4 (d, J=7.5 Hz), 129.3 (d, J=23.2 Hz), 128.5 (d, J=6.7 Hz), 128.1 (d, J=3.0 Hz), 128.0, 127.9 (d, J=3.0 Hz, 1H), 122.1 (d, J=19.5 Hz), 117.8 (dd, J=137.6, 3.7 Hz), 76.2, 71.8 (d, J=129.4 Hz), 53.3, 52.3, 43.5 (dd, J=24.7, 6.7 Hz); $^{31}$P NMR (162 MHz, CDCl$_3$): δ 27.21 ppm; HRMS (ESI) calcd for C$_{38}$H$_{39}$N$_4$OP [M+Na]$^+$: 621.2754; found: 621.2763.

s. Synthesis of (S)-1,3-diphenyl-2-(phenyl(thiomorpholino)methyl)-1,3,2-diazaphospholidine 2-oxide

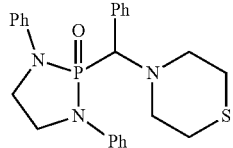

Off-white solid (22.1 mg, 0.049 mmol, 49%). mp: 191-193° C. IR (Neat, cm$^{-1}$): 3057, 2951, 2883, 1599, 1494, 1271, 1114, 1033; $^1$H NMR (400 MHz, CDCl$_3$): δ 7.45 (d, J=7.8 Hz, 2H), 7.35 (q, J=6.4 Hz, 4H), 7.28-7.16 (m, 5H), 7.08 (qt, J=7.4, 1.2 Hz, 2H), 6.93 (d, J=6.8 Hz, 2H), 4.18 (d, J=7.3 Hz, 1H), 3.70-3.63 (m, 1H), 3.38 (dq, J=8.2, 2.7 Hz, 1H), 3.23 (dq, J=8.6, 2.7 Hz, 1H), 3.08-3.03 (m, 2H), 2.86-2.80 (m, 2H), 2.61-2.51 (m, 5H); $^{13}$C NMR (100 MHz, CDCl$_3$): δ 142.0 (dd, J=43.4, 7.5 Hz), 133.7 (d, J=2.2 Hz), 130.3 (d, J=7.5 Hz), 129.2 (d, J=23.2 Hz), 128.1 (d, J=3.0 Hz), 127.9 (d, J=1.5 Hz), 122.4 (d, J=38.1 Hz), 118.1 (dd, J=158.6, 3.7 Hz), 72.1 (d, J=130.1 Hz), 54.6 (d, J=8.2 Hz), 43.7 (dd, J=73.3, 6.7 Hz), 27.9; $^{31}$P NMR (162 MHz, CDCl$_3$): δ 26.51 ppm; HRMS (ESI) calcd for C$_{25}$H$_{28}$N$_3$OPS [M+Na]$^+$: 472.1583; found: 472.1589.

t. Synthesis of 2-((1S)-(3,5-dimethylmorpholino)(phenyl)methyl)-1,3-diphenyl-1,3,2-diazaphospholidine 2-oxide

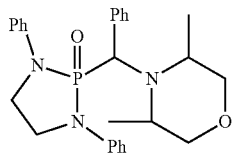 [SMILES: CC1COCC(C)N1C(c1ccccc1)P1(=O)N(c2ccccc2)CCN1c1ccccc1]

Off-white solid (40.4 mg, 0.087 mmol, 87%). mp: 188-189° C. IR (Neat, cm$^{-1}$): 3061, 2972, 2874, 1599, 1494, 1269, 1126, 1035; $^1$H NMR (400 MHz, CDCl$_3$): δ 7.52 (d, J=8.6 Hz, 2H), 7.34 (t, J=8.2 Hz, 4H), 7.25-7.16 (m, 5H), 7.06 (q, J=7.2 Hz, 2H), 6.91-6.89 (m, 2H), 4.09-4.05 (m, 2H), 3.70-3.62 (m, 2H), 3.56-3.50 (m, 1H), 3.29 (dq, J=8.8, 2.7 Hz, 1H), 3.07 (dq, J=8.4, 2.7 Hz, 1H), 2.50 (d, J=11.3 Hz, 1H), 2.24 (dq, J=8.4, 2.5 Hz, 1H), 2.00 (t, J=10.7 Hz, 1H), 1.39 (t, J=10.7 Hz, 1H), 1.18 (d, J=6.3 Hz, 3H), 0.93 (t, J=6.3 Hz, 3H); $^{13}$C NMR (100 MHz, CDCl$_3$): δ 142.1 (dd, J=39.6, 7.5 Hz), 134.3 (d, J=4.5 Hz), 130.3 (d, J=7.5 Hz), 129.3 (d, J=29.2 Hz), 128.2 (d, J=3.0 Hz), 128.1 (d, J=2.2 Hz), 122.4 (d, J=52.3 Hz), 117.9 (dd, J=216.9, 3.7 Hz), 71.9 (d, J=6.7 Hz), 71.8 (d, J=128.6 Hz), 60.1 (d, J=2.2 Hz), 58.2 (d, J=13.5 Hz), 43.6 (dd, J=74.8, 6.7 Hz), 19.3 (d, J=14.9 Hz); $^{31}$P NMR (162 MHz, CDCl$_3$): δ 26.66 ppm; HRMS (ESI) calcd for C27H32N3O$_2$P [M+Na]$^+$: 484.2124; found: 484.2126.

u. Synthesis of (S)-1-((2-oxido-1,3-diphenyl-1,3,2-diazaphospholidin-2-yl(phenyl)methyl)piperidin-4-one

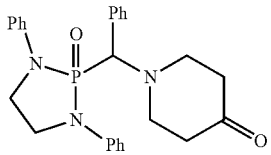 [SMILES: O=C1CCN(C(c2ccccc2)P2(=O)N(c3ccccc3)CCN2c2ccccc2)CC1]

Off-white solid (19.3 mg, 0.043 mmol, 43%). mp: 151-154° C. IR (Neat, cm$^{-1}$): 3059, 2970, 2887, 1716, 1599, 1504, 1271, 1118, 1035; $^1$H NMR (400 MHz, CDCl$_3$): δ 7.50 (d, J=8.4 Hz, 2H), 7.37-7.15 (m, 9H), 7.10-6.96 (m, 4H), 4.23 (d, J=11.3 Hz, 1H), 3.66 (dq, J=8.0, 3.1 Hz, 1H), 3.34 (dq, J=8.8, 3.2 Hz, 1H), 3.22 (quint, J=5.6 Hz, 2H), 3.15 (dq, J=8.4, 4.7 Hz, 1H), 2.86 (quint, J=7.0 Hz, 2H), 2.42-2.24 (m, 5H); $^{13}$C NMR (100 MHz, CDCl$_3$): δ 209.2, 142.1 (dd, J=27.7, 7.5 Hz), 134.7 (d, J=3.7 Hz), 130.0 (d, J=6.7 Hz), 129.3 (d, J=27.7 Hz), 128.5 (d, J=2.2 Hz), 128.3 (d, J=2.2 Hz), 122.5 (d, J=59.8 Hz), 118.1 (dd, J=214.7, 5.3 Hz), 70.8 (d, J=129.4 Hz), 52.6 (d, J=8.2 Hz), 43.8 (dd, J=106.2, 7.5 Hz), 41.4; $^{31}$P NMR (162 MHz, CDCl$_3$): δ 26.03 ppm; HRMS (ESI) calcd for C$_{26}$H$_{28}$N$_3$O$_2$P [M+Na]$^+$: 468.1811; found: 468.1814.

v. Synthesis of 2-(morpholinomethyl)-1,3-diphenyl-1,3,2-diazaphospholidine 2-oxide

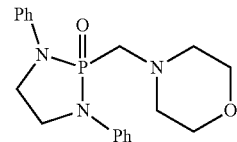

Off-white solid (25.5 mg, 0.071 mmol, 71%). mp: 170-172° C. IR (Neat, cm$^{-1}$): 3061, 2957, 2850, 1599, 1494, 1271, 1116, 1033; $^1$H NMR (400 MHz, CDCl$_3$): δ 7.36-7.27 (m, 8H), 7.03 (app t, J=5.9 Hz, 2H), 3.92-3.86 (m, 4H), 3.48-3.46 (m, 4H), 3.12 (d, J=8.0 Hz, 2H), 2.18-2.16 (m, 4H); $^{13}$C NMR (100 MHz, CDCl$_3$): δ 142.0 (d, J=8.2 Hz), 129.7, 122.1, 116.5 (d, J=4.5 Hz), 67.3, 54.9 (d, J=8.2 Hz), 54.2 (d, J=137.6 Hz), 44.0 (d, J=6.0 Hz); $^{31}$P NMR (162 MHz, CDCl$_3$): δ 29.86 ppm; HRMS (ESI) calcd for C19H24N$_3$O$_2$P [M+Na]$^+$: 380.1498; found: 380.1492.

2. Synthesis of 1-(2-((1,3-diphenyl-1,3,2-diazaphospholidin-2-yl)oxy)-2-methylpropyl)-3-phenylthiourea

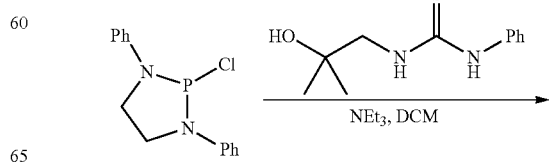

-continued

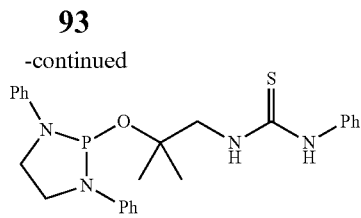

¹H (CDCl₃, 400 MHZ): δ 7.91 (bs, 1H), 7.46-6.88 (m, 15H), 6.24 (bs, 1H), 3.51-3.40 (m, 6H), 1.24 (s, 6H); ¹³C (CDCl₃, 100.5 MHZ): δ 180.3, 144.6 (d, J=17.1 Hz), 130.3, 129.9, 129.3, 126.9, 125.0, 120.1, 115.9 (d, J=14.1 Hz), 56.3, 46.2 (d, J=8.6 Hz), 26.7 (d, J=9.7 Hz).

3. Optimization of Reaction Conditions

Figure 1B:
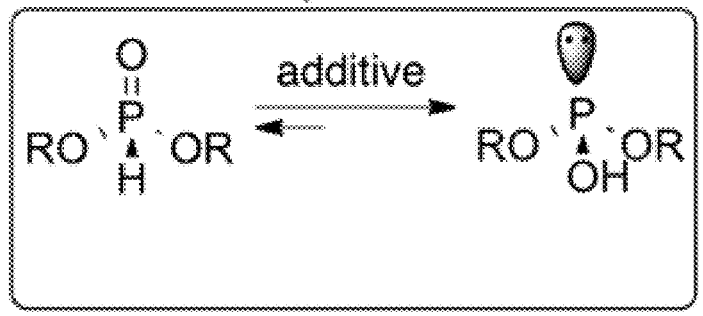
Figure 1C:
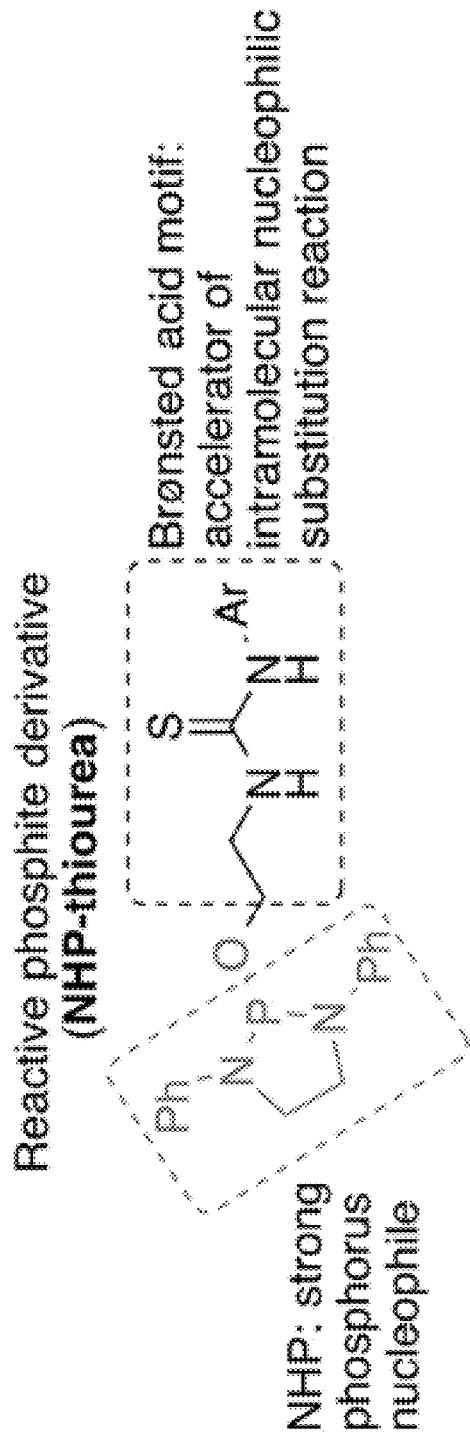

A highly reactive phosphorus nucleophile is key to achieving mild and efficient phosphonylation of α-aminophosphonates employing amines and aldehydes. To generate the active phosphite species in-situ, additives are typically required to facilitate phosphonate-phosphite tautomerization because non-nucleophilic phosphonates are the predominant form under neutral conditions (FIG. 1A and FIG. 1B) (Suyama et al. (2010) Angew. Chem. Int. Ed. 49: 797-799; Mastryukova et al. (1980) Pure Appl. Chem. 52: 945-957; Hammond (1962) J. Chem. Soc. 1365-1369). Hence, the design and synthesis of highly nucleophilic phosphite derivatives is desirable (FIG. 1C).

A recent study on a previously unknown N-heterocyclic phosphine (NHP)-thiourea has demonstrated a strong nucleophilicity toward allene electrophiles affording vinyl-diazaphosphonates via phospha-Michael/intramolecular nucleophilic displacement under mild reaction conditions (Mulla et al. (2015) J. Org. Chem.). Without wishing to be bound by theory, it is therefore hypothesized that an effective phosphonylation reagent for tertiary α-aminophosphonates would contain: (a) an N-heterocyclic phosphine (NHP) as a strong phosphorus nucleophile in favor of phospha-Mannich process and (b) a Brønsted acid motif to accelerate the intramolecular nucleophilic displacement in the absence of additives.

To test this hypothesis, a one-pot multicomponent reaction among benzaldehyde 1a, morpholine 2a, and NHP-thiourea 3a without base or metal additives was explored (Table 1). An initial reaction in THF provided a moderate yield of the α-N-heterocyclic phosphonates (entry 1, 48%). Sequential screening of polar solvents such as CH3CN and EtOH generated the desired product in high yields at elevated temperatures (entries 2-3, 69-83%). Further increase in reaction temperature using high boiling point solvents such as toluene and xylene (entries 4, 5) was found to cause significant decomposition of NHP to ethylenedianiline, resulting in lowered yields (41-69%). Next, halogenated solvents such as CHCl3 and 1,2-DCE were investigated (entries 6, 7). Exploring the chlorinated solvents provided an optimum solvent of 1,2-DCE for this transformation, yielding the desired product in 90% (entry 7).

TABLE 1

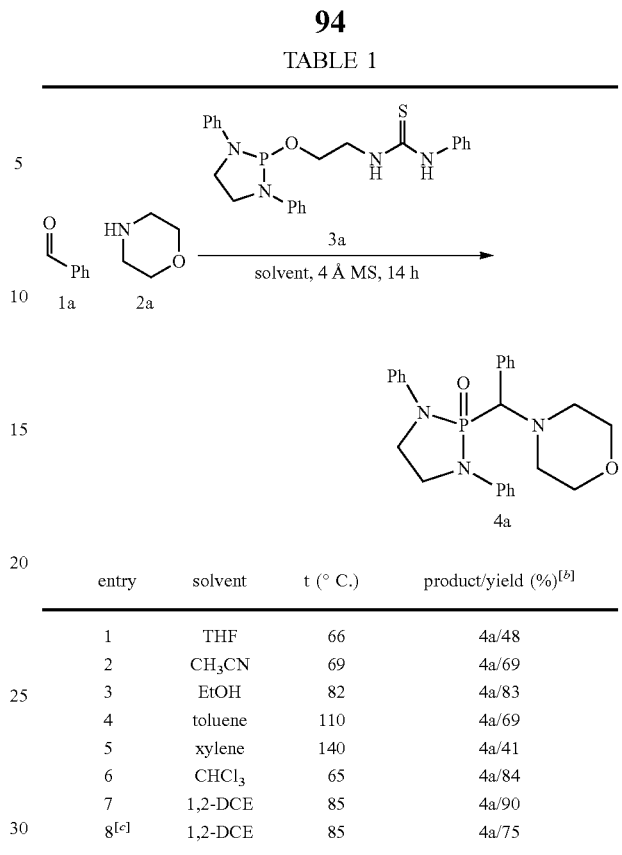

| entry | solvent | t (° C.) | product/yield (%)[b] |
|---|---|---|---|
| 1 | THF | 66 | 4a/48 |
| 2 | CH₃CN | 69 | 4a/69 |
| 3 | EtOH | 82 | 4a/83 |
| 4 | toluene | 110 | 4a/69 |
| 5 | xylene | 140 | 4a/41 |
| 6 | CHCl₃ | 65 | 4a/84 |
| 7 | 1,2-DCE | 85 | 4a/90 |
| 8[c] | 1,2-DCE | 85 | 4a/75 |

4. Screening of N-heterocyclic Phosphines

The effect of the Brøensted acid motif on this transformation was then explored (Table 2). First, variations of the pKa values of Brønsted acids were screened. The parent NHP-phenyl-thiourea provided α-N-heterocyclic phosphonate 4a in excellent yield (entry 1, 90%). Replacement of the phenyl-thiourea moiety with a lower pKa valued group, 3,5-bis(trifluoromethyl)phenyl-thiourea, led to a significant reduction in the yield of 4a (entry 1 vs 2). The less acidic 4-methoxylphenyl-thioure, on the other hand, did not show any better performance than the parent thiourea (entry 3, 72%). Further variation of the Brønsted acid with a methyl substitution on the nitrogen atom significantly lowered their reactivity (entries 4, 5), presumably preventing the intramolecular nucleophilic substitution reaction sequence. Without wishing to be bound by theory, these low-yielding reactions may be attributed to the slower intermolecular substitution reaction compared with the intramolecular nucleophilic displacement, which can be experimentally supported by a comparison of NHP-thiourea and NHP—N-methylated thiourea reactions (entry 1, 90% vs 4, 48%). Moreover, the NHP-ethanol-mediated reaction, which provided a significantly reduced yield (entry 6, 31%), proved the Brønsted acid motif as an accelerator for this substitution reaction. Lastly, it should be noted that the use of triethyl phosphite P(OEt)3 gave a relatively lower yield of 79%, although it has been widely applied in the additive-mediated synthesis of α-aminophosphonates.

TABLE 2

| entry | NHP | product/yield (%)[b] |
|---|---|---|
| 1 | 3a | 4a/90 |
| 2 | 3b | 4a/40 |
| 3 | 3c | 4a/72 |
| 4 | 3d | 4a/48 |
| 5 | 3e | 4a/31 |
| 6 | 3f | 4a/31 |

5. Aldehyde Scope of One-Pot Synthesis of α-N-Heterocyclic Phosphonate

With the optimized reaction conditions established, the scope of the reaction was explored in terms of aldehyde substrates (Table 3). A wide range of aldehydes with different substituents underwent clean reactions to afford α-N-heterocyclic phosphonates in moderate to excellent yields (33-93% yields). Ortho and/or para-halogenated benzaldehydes were transformed into the corresponding products (4b-4h) in high to excellent yields, attesting to a high steric tolerance. In particular, a sterically hindered 3,5-dimethyl-morpholine was well tolerated under the reaction conditions and afforded the desired product in high yield (4i, 87%). The electronic effects of the aldehyde electrophiles were also explored. Attachment of electron-donating groups to aldehydes (4j-4l) had a negligible influence on this reaction; however, a sharp decrease in product yields was observed when electron-deficient groups were present in the aldehydes such as nitro-benzaldehydes (4n, 43%), presumably due to the instability of in-situ generated transient iminium intermediates. In addition, heteroaromatic aldehydes provided the target compounds in moderate to high yields (4o, 33% and 4p, 69%). Finally, the aliphatic aldehydes such as butyraldehyde and formaldehyde were found to undergo effective transformation (4q, 63% and 4r, 71%).

TABLE 3

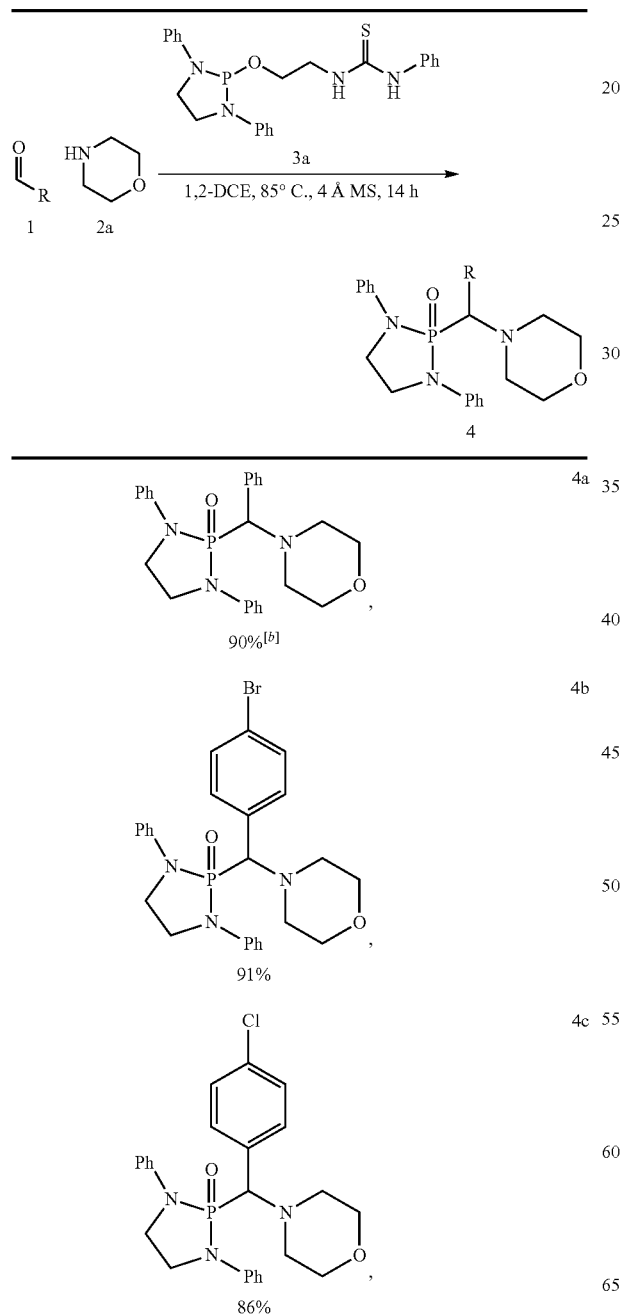

TABLE 3-continued

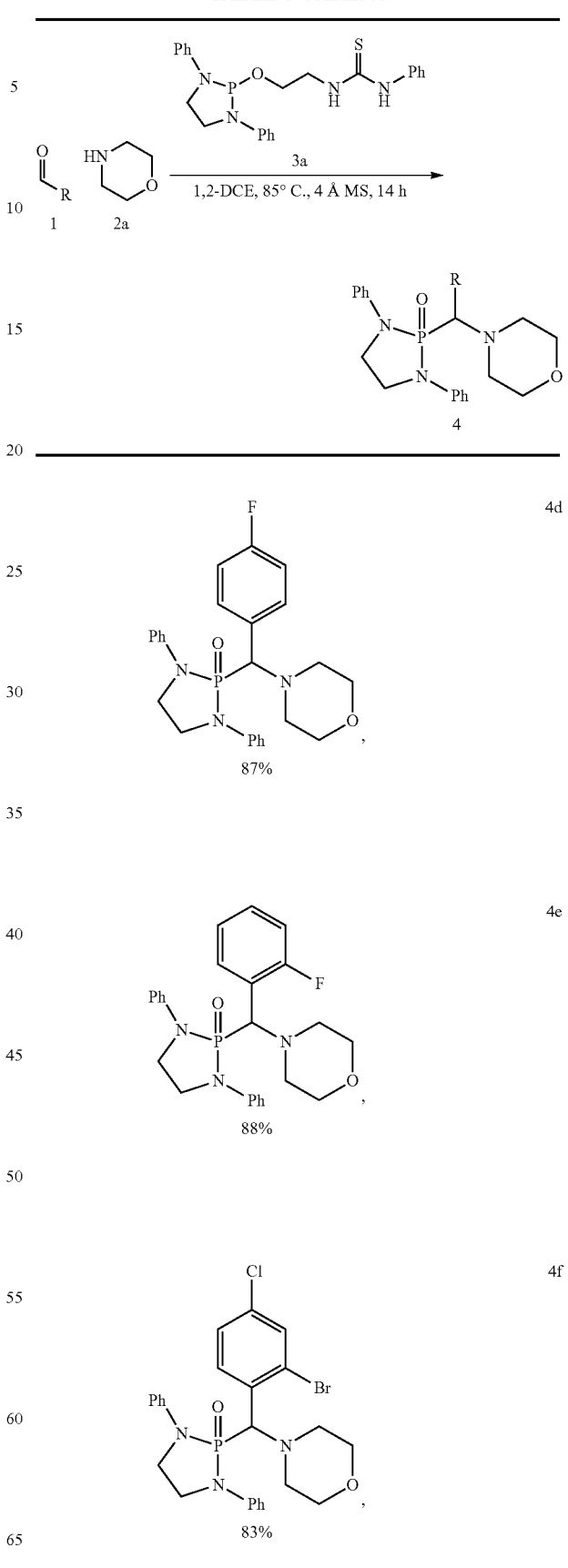

TABLE 3-continued
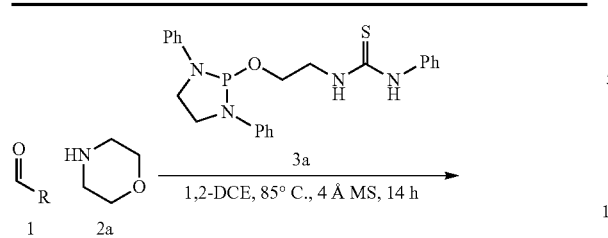
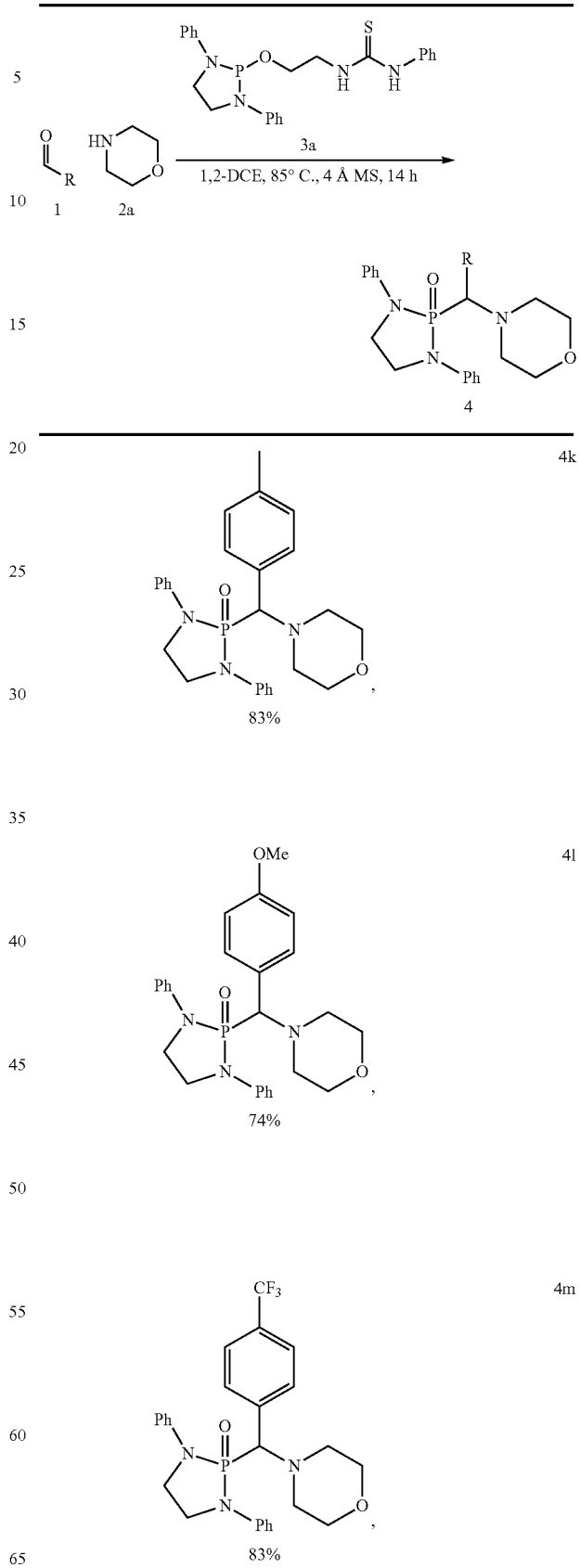

TABLE 3-continued
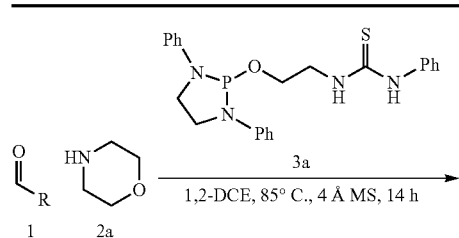
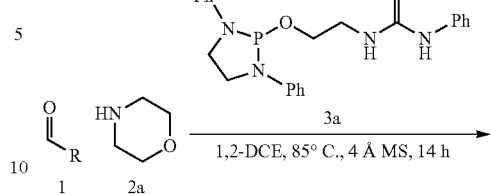
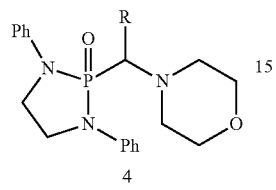
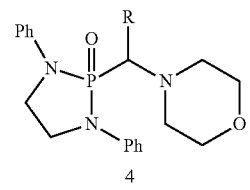
| | |
|---|---|
| 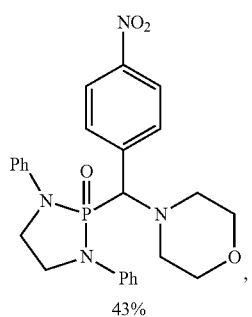 43% | 4n |
| 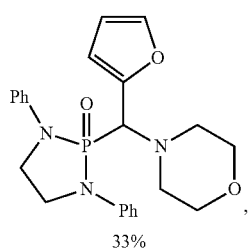 [SMILES: O=P1(C(c2ccco2)N2CCOCC2)N(c2ccccc2)CCN1c1ccccc1] 33% | 4o |
| 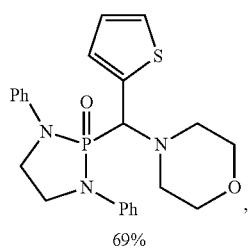 [SMILES: O=P1(C(c2cccs2)N2CCOCC2)N(c2ccccc2)CCN1c1ccccc1] 69% | 4p |
| 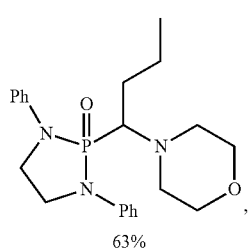 63% | 4q |
| | |
|---|---|
| 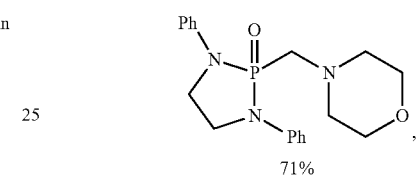 71% | 4r |
| 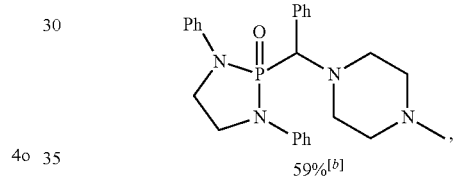 59%[b] | 4s |
| 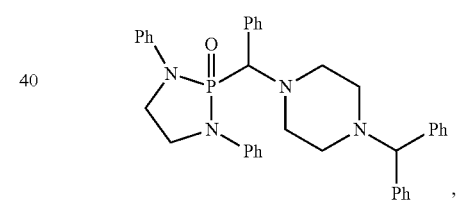 87% | 4t |
| 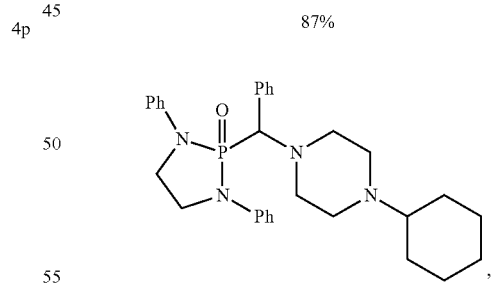 68% | 4u |
| 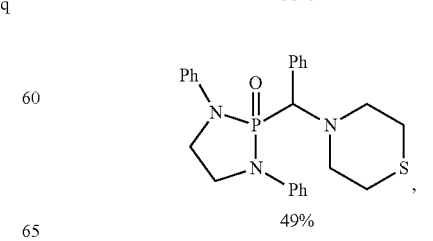 49% | 4v |

TABLE 3-continued

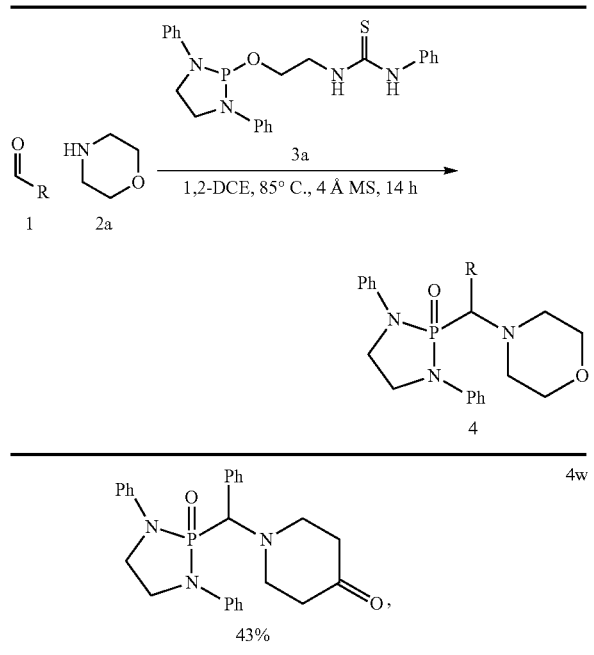

Figure 2:
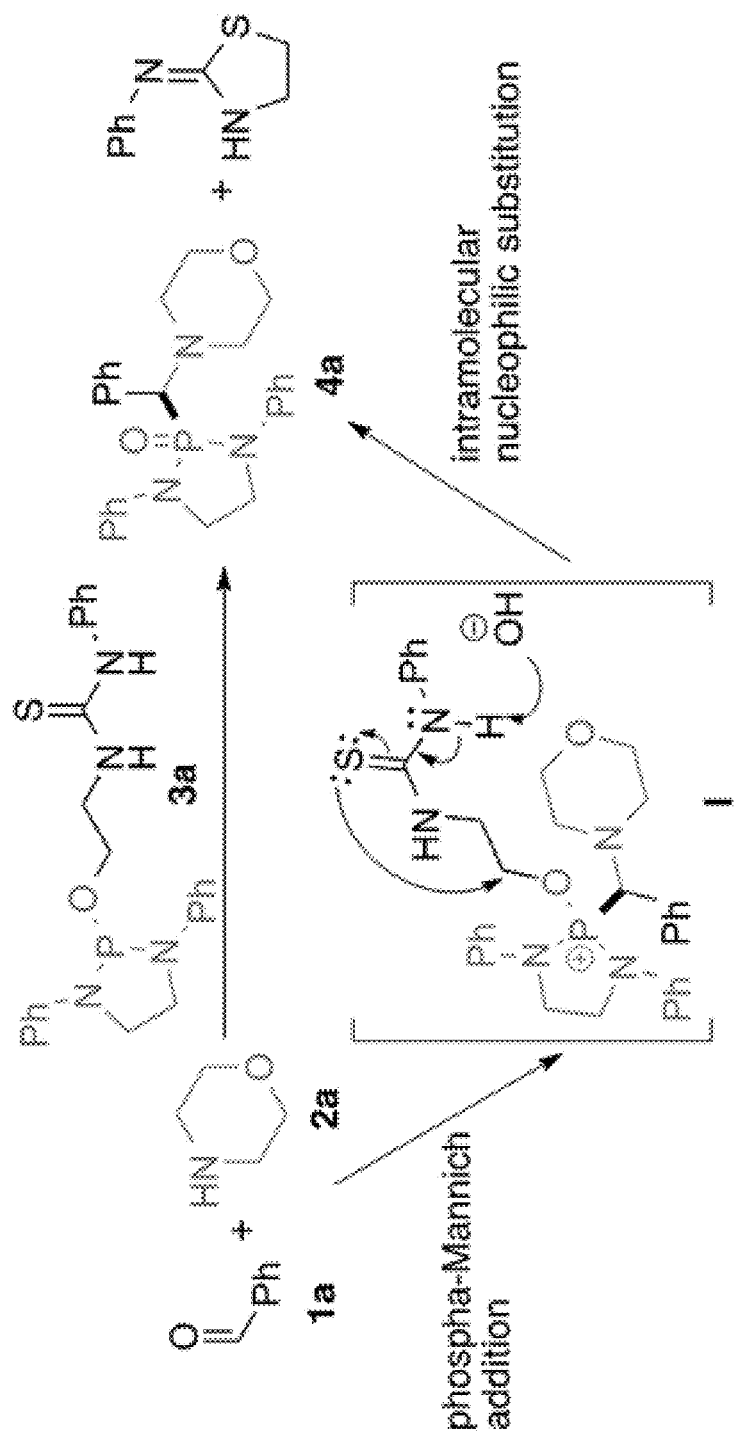
FIG. 2 shows a representative schematic of a proposed reaction sequence.

Next, the scope of the N-heterocyclic amines that would be tolerated in this transformation was explored (Table 3). Piperazine derivatives with various substituents at the nitrogen atom were similarly tolerated in this protocol (entries 4s-4u). Similarly, thiopiperazine, a sulfur analogue of piperazine, has proven effective under the standard reaction conditions (4v). In addition, 4-piperidinone turned out to be a viable amine for this transformation (4w), which showed a high tolerance to a wide range of cyclic secondary amines, found in numerous biologically active molecules (FIG. 2).

6. Proposed Reaction Sequence

Based on the experiment results and previous report (Mulla et al. (2016) *J. Org. Chem.*), a proposed reaction sequence is illustrated in FIG. 2. The treatment of aldehyde 1a with amine 2a generated a transient iminium intermediate, which rapidly underwent phospha-Mannich reaction with the NHP-thiourea 3a to generate a diazaphosphonium intermediate I. A sequential deprotonation/intramolecular nucleophilic substitution reaction ultimately furnished the α-N-heterocyclic phosphonate 4a and the thiazolidine byproduct, which contributed critically to the mechanism analysis.

Accordingly, a novel N-heterocyclic phosphine-mediated phospha-Mannich/intramolecular nucleophilic substitution reaction as a general method for making tertiary α-aminophosphonates has been developed. This transformation provides a rapid access to α-N-heterocyclic phosphonates, having the advantages of moderate to excellent yields for various substrates (33-93%) and metal-free mild reaction conditions. This method would be a useful alternative to the classical metal-mediated synthesis of α-N-heterocyclic phosphonates, which is typically challenging and low-yielding. Moreover, this study, for the first time, demonstrated the critical role of Brønsted acid motif as an accelerator of the sequential intramolecular nucleophilic substitution process in the phosphonylation such as the Kabachnick and Fields reaction.

J. REFERENCES

Ghosh, S.; Chan, J. M. W.; Lea, C. R.; Meints, G. A.; Lewis, J. C.; Tovian, Z. S.; Flessner, R. M.; Loftus, T. C.; Bruchhaus, I.; Kendrick, H.; Croft, S. L.; Kemp, R. G.; Kobayashi, S.; Nozaki, T.; Oldfield, E., *J. Med. Chem.* 2004, 47, 175-187.

Yang, R.; Zhao, R.; Chen, D.; Shan, L.; Yun, L.; Wang, H., *Bioorg. Med. Chem. Lett.* 2004, 14, 3017-3025.

Chaudhary, P.; Kumar, R.; Verma, A. K.; Singh, D.; Yadav, V.; Chhillar, A. K.; Sharma, G. L.; Chandra, R., *Bioorg. Med. Chem.* 2006, 14, 1819-1826.

Younes, S., *J. Pharm. Belg.* 1994, 49 N∝2 MARS AVRIL, 119-125.

Amar, H.; Braisaz, T.; Villemin, D.; Moreau, B., *Mater. Chem. Phys.* 2008, 110, 1-6.

Lewkowski, J.; Jóźwiak, A.; Tokarz, P.; Zagórski, P. M.; Hamera, R.; Cal, D.; Satala, G.; Bojarski, A. J., *Heteroat. Chem.* 2015, 26, 290-298.

Kafarski, P.; Lejczak, B., *Phosphorus, Sulfur Silicon Relat. Elem.* 1991, 63, 193-215.

Allen, J. G.; Atherton, F. R.; Hall, M. J.; Hassall, C. H.; Holmes, S. W.; Lambert, R. W.; Nisbet, L. J.; Ringrose, P. S., *Nature* 1978, 272, 56-58.

Fields, E. K., *J. Am. Chem. Soc.* 1952, 74, 1528-1531.

Kabachnik, M.; Medved, T., *Doklady Akademii Nauk SSSR* 1952, 83, 689-692.

Pudovik, A.; Konovalova, I., *Synthesis* 1979, 81-96.

Ordóñiez, M.; Rojas-Cabrera, H.; Cativiela, C., *Tetrahedron* 2009, 65, 17-49.

Azizi, K.; Karimi, M.; Heydari, A., *Tetrahedron Lett.* 2014, 55, 7236-7239.

Qian, C.; Huang, T., *J. Org. Chem.* 1998, 63, 4125-4128.

Kasthuraiah, M.; Kumar, K. A.; Reddy, C. S.; Reddy, C. D., *Heteroat. Chem.* 2007, 18, 2-8.

Stawinski, J.; Kraszewski, A., *Acc. Chem. Res.* 2002, 35, 952-960.

Doak, G. O.; Freedman, L. D., *Chem. Rev.* 1961, 61, 31-44.

Ma, J.-A., *Chem. Soc. Rev.* 2006, 35, 630-636.

Kumar, A.; Sharma, V.; Kaur, J.; Kumar, V.; Mahajan, S.; Kumar, N.; Chimni, S. S., *Tetrahedron* 2014, 70, 7044-7049.

Suyama, K.; Sakai, Y.; Matsumoto, K.; Saito, B.; Katsuki, T., *Angew. Chem. Int. Ed.* 2010, 49, 797-799.

Sobhani, S.; Falatooni, Z. M.; Honarmand, M., *RSC Adv.* 2014, 4, 15797-15806.

Bhagat, S.; Chakraborti, A. K., *J. Org. Chem.* 2007, 72, 1263-1270.

Reddy, B. R. P.; Reddy, P. V. G.; Reddy, B. N., *New J. Chem.* 2015, 39, 9605-9610.

Ma'mani, L.; Heydari, A.; Shiroodi, R. K., *Curr. Org. Chem.* 2009, 13, 758-762.

Reddy, B. V. S.; Krishna, A. S.; Ganesh, A. V.; Kumar, G. G. K. S. N., *Tetrahedron Lett.* 2011, 52, 1359-1362.

Nazish, M.; Saravanan, S.; Khan, N.-u. H.; Kumari, P.; Kureshy, R. I.; Abdi, S. H. R.; Bajaj, H. C., *Chem Plus Chem* 2014, 79, 1753-1760.

Sheykhan, M.; Ma'mani, L.; Ebrahimi, A.; Heydari, A., *J. Mol. Catal. A: Chem.* 2011, 335, 253-261.

Malamiri, F.; Khaksar, S., *J. Chem. Sci.* 2014, 126, 807.

Prauda, I.; Greiner, I.; Ludányi, K.; Keglevich, G., *Synth. Commun.* 2007, 37, 317-322.

Zakharov, S. V.; Nuriazdanova, G. K.; Garifzyanov, A. R.; Galkin, V. I.; Cherkasov, R. A., *Russ. J. Gen. Chem.* 2004, 74, 873-881.

Makarov, M. V.; Skvortsov, E. A.; Brel, V. K., *Mendeleev Commun.* 2015, 25, 232-233.

Azizi, N.; Saidi, M. R., *Tetrahedron* 2003, 59, 5329-5332.

Malhiac, C.; Combret, J.-C.; Boussad, K.; Klein, J.-L., *Phosphorus, Sulfur Silicon Relat. Elem.* 1996,113, 299-301.

Mastryukova, T.; Aladzheva, I.; Leont'eva, I.; Petrovski, P.; Fedin, E.; Kabachnik, M., *Pure Appl. Chem.* 1980, 52, 945-957.

Hammond, P., *J. Chem. Soc.* 1962, 1365-1369.

Mulla, K.; Aleshire, K. L.; Forster, P. M.; Kang, J.-Y., *J. Org. Chem.* 2016, 81, 77-88.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

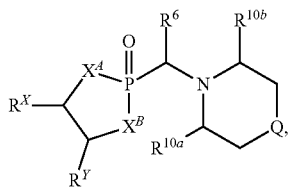

wherein Q is selected from O, S, C=O, S=O, $SO_2$, and $NR^1$;

wherein each of $X^A$ and $X^B$ is independently $NR^1$;

wherein each occurrence of $R^1$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of $R^1$ is independently substituted with 0, 1, 2, 3, or 4 independently selected $R^5$ groups;

wherein each occurrence of $R^5$, when present, is independently selected from halogen, —$NO_2$, —CN, —OH, —SH, —$NH_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C=O)(C1-C3 alkyl), —(S=O)(C1-C3 alkyl), —$SO_2$(C1-C3 alkyl), —$CO_2R^{11}$, —(C=O)$NR^{12a}R^{12b}$, —$SO_2NR^{12a}R^{12b}$, —O(C=O)$NR^{12a}R^{12b}$, —$NHSO_2NR^{12a}R^{12b}$, and —NH(C=O)$NR^{12a}R^{12b}$;

wherein each occurrence of $R^{11}$, when present, is independently selected from hydrogen and C1-C4 alkyl;

wherein each occurrence of $R^{12a}$ and $R^{12b}$, when present, is independently selected from hydrogen and C1-C3 alkyl;

wherein each of $R^X$ and $R^Y$ is independently selected from hydrogen, C1-C8 alkyl, C6-C10 aryloxy, C6-C10 aryl, and 4-10 membered heteroaryl, or wherein each of Rx and $R^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected $R^5$ groups;

wherein $R^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected $R^5$ groups; and wherein each of $R^{10a}$ and $R^{10b}$ is independently selected from hydrogen and C1-C4 alkyl, or a salt thereof.

2. The compound of claim 1, wherein each of $R^X$ and $R^Y$ is hydrogen.

3. The compound of claim 1, wherein $R^5$ is C6-C10 aryl substituted with 0, 1, 2, or 3 groups independently selected from halogen, —$NO_2$, —CN, —OH, —SH, —$NH_2$, and C1-C4 alkyl.

4. The compound of claim 1, wherein each of $R^{10a}$ and $R^{10b}$ is hydrogen.

5. The compound of claim 1, wherein the compound has a structure represented by a formula selected from:

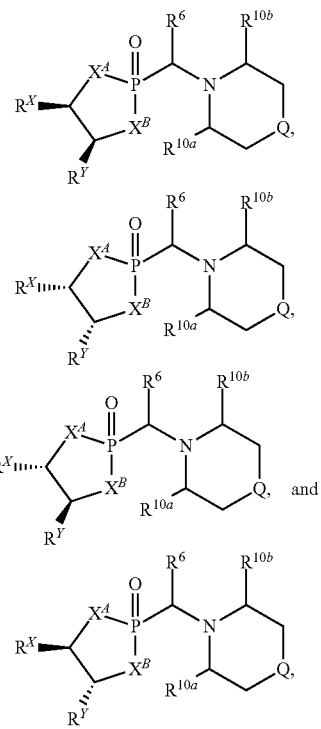

or a salt thereof.

6. The compound of claim 1, wherein the compound has a structure represented by a formula selected from:

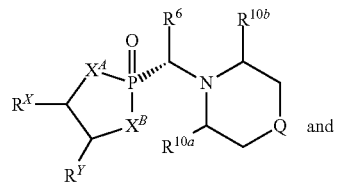

-continued
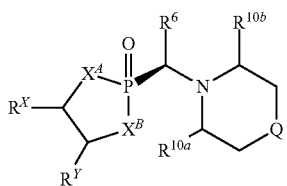
or a salt thereof.
7. The compound of claim 1, wherein the compound has a structure represented by a formula:
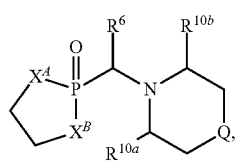
or a salt thereof.
8. The compound of claim 1, wherein the compound has a structure represented by a formula:
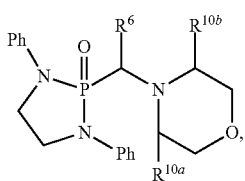
or a salt thereof.
9. The compound of claim 1, wherein the compound is selected from:
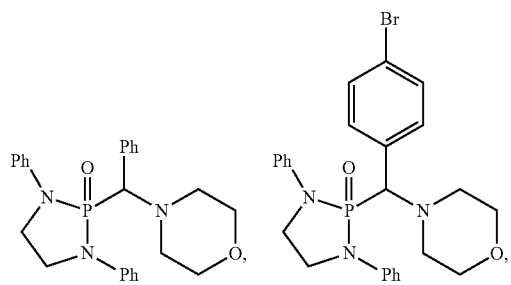
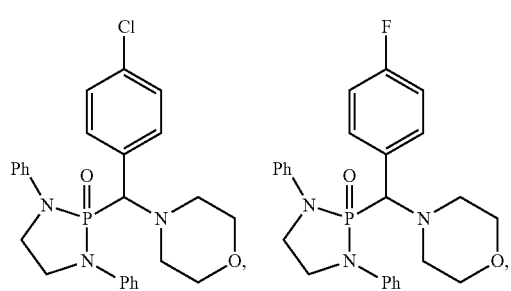
-continued
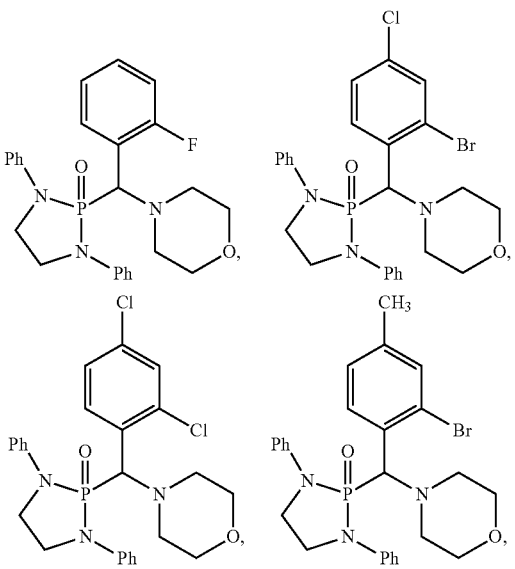
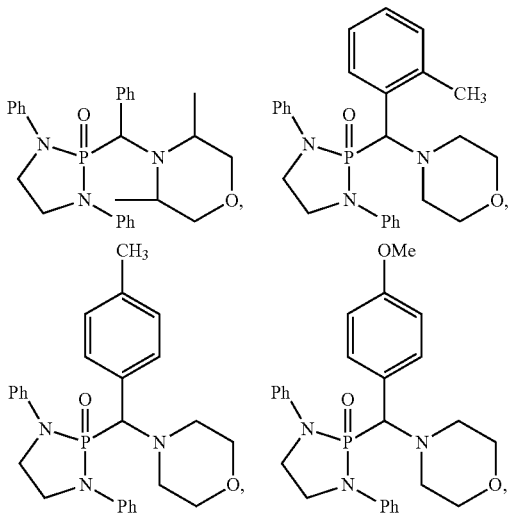
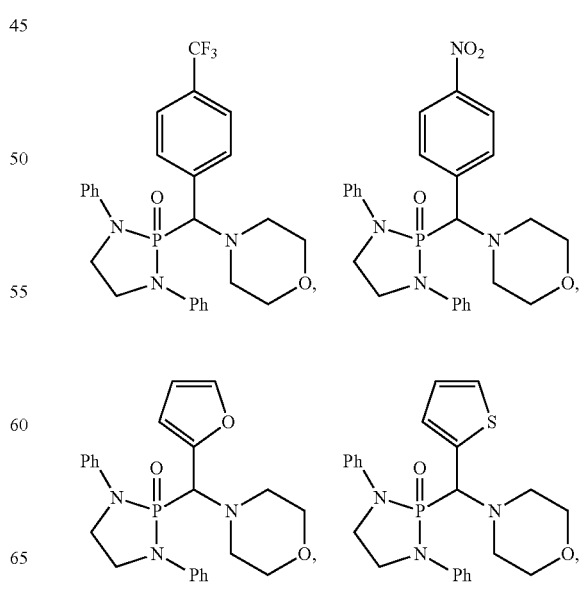

109

-continued

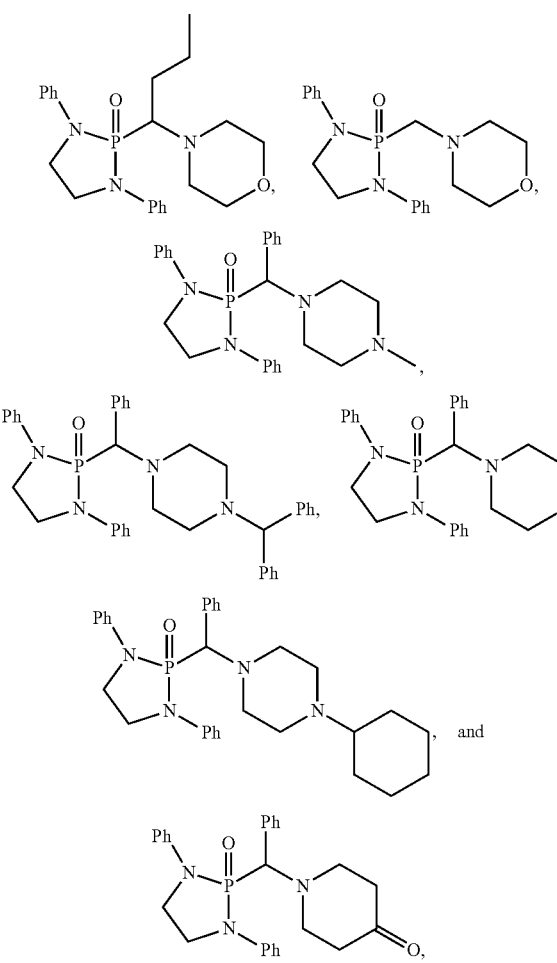

or a salt thereof.

10. The compound of claim 1, wherein the compound is selected from:

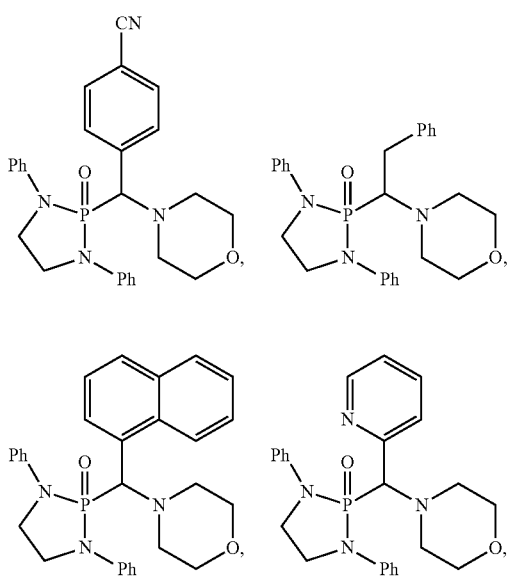

110

-continued

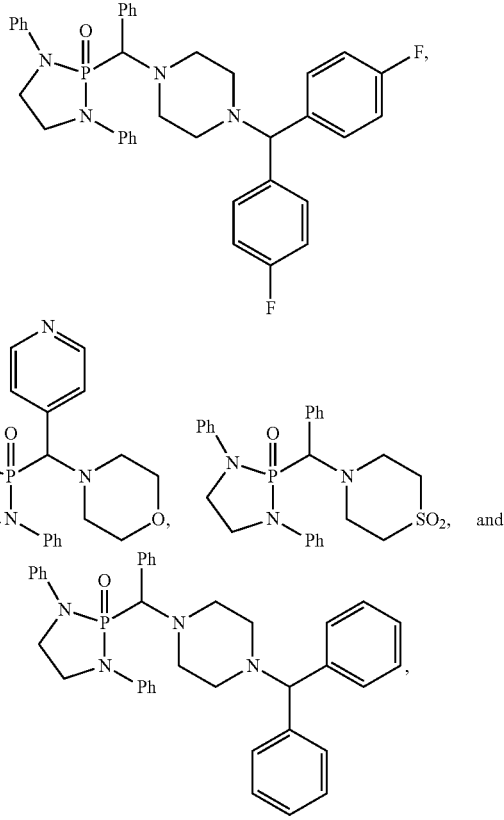

or a salt thereof.

11. A method of making a compound having a structure represented by a formula:

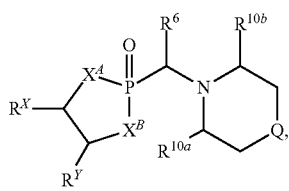

wherein Q is selected from O, S, C=O, S=O, SO$_2$, and NR$^1$;

wherein each of X$^A$ and X$^B$ is independently selected from NR$^1$, O, and S;

wherein each occurrence of R$^1$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each occurrence of R$^1$, when present, is independently substituted with 0, 1, 2, 3, or 4 independently selected R$^5$ groups;

wherein each occurrence of R$^5$, when present, is independently selected from halogen, —NO$_2$, —CN, —OH, —SH, —NH$_2$, C1-C4 alkyl, C2-C4 alkenyl, C2-C4 alkynyl, C1-C3 haloalkyl, C1-C3 cyanoalkyl, C1-C3 hydroxyalkyl, C1-C3 haloalkoxy, C1-C3 alkoxy, C1-C3 thioalkyl, C1-C3 alkyl(C1-C3 alkoxy), C1-C3 alkylamino, (C1-C3)(C1-C3) dialkylamino, C3-C7 cycloalkyl, optionally substituted C6-C10 aryl, —(C═O)(C1-C3 alkyl), —(S═O)(C1-C3 alkyl), —SO$_2$(C1-C3 alkyl), —CO$_2$R, —(C═O)NR$^{12a}$R$^{12b}$, —SO$_2$NR$^{12a}$R$^{12b}$, —O(C═O)NR$^{12a}$R$^{12b}$, —NHSO$_2$NR$^{12a}$R$^{12b}$, and —NH(C═O)NR$^{12a}$R$^{12b}$;

wherein each occurrence of R$^{11}$, when present, is independently selected from hydrogen and C1-C4 alkyl;

wherein each occurrence of R$^{12a}$ and R$^{12b}$, when present, is independently selected from hydrogen and C1-C3 alkyl;

wherein each of R$^X$ and R$^Y$ is independently selected from hydrogen, C1-C8 alkyl, C6-C10 aryloxy, C6-C10 aryl, and 4-10 membered heteroaryl, or wherein each of R$^X$ and R$^Y$ are optionally covalently bonded together and, together with the intermediate atoms, comprise a 5- to 7-membered cycloalkyl, a 5- to 7-membered heterocycloalkyl, a 5- to 7-membered aryl, or a 5- to 7-membered heteroaryl and are substituted with 0, 1, 2, 3, or 4 independently selected R$^5$ groups;

wherein R$^6$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups; and wherein each of R$^{10a}$ and R$^{10b}$ is independently selected from hydrogen and C1-C4 alkyl, or a salt thereof, the method comprising the step of reacting an aldehyde having a structure represented by a formula:

or a salt thereof, with a heterocycloalkane having a structure represented by a formula:

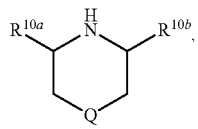

or a salt thereof, in the presence of a reagent having a structure represented by a formula:

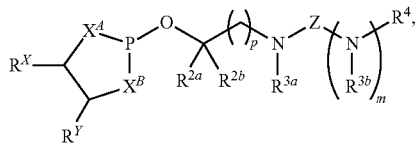

wherein m is selected from 0 and 1;
wherein p is selected from 0, 1, 2, 3, 4, and 5;

wherein Z is selected from C═O, C═S, S═O, SO$_2$, and a structure represented by a formula:

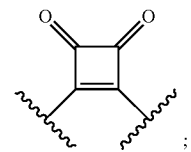 [SMILES: *c1c(*)c(=O)c1=O]

wherein each of R$^{2a}$ and R$^{2b}$ is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and substituted with 0, 1, 2, 3, or 4 independently selected R$^5$ groups;

wherein each of R$^{3a}$ and R$^{3b}$, when present, is independently selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, —(C1-C3 alkyl)(C6-C10 aryl), and 4-10 membered heteroaryl, and wherein each of R$^{3a}$ and R$^{3b}$ is independently substituted with 0, 1, 2, 3, or 4 independently selected R$^5$ groups; and wherein R$^4$ is selected from hydrogen, C1-C6 alkyl, C1-C6 haloalkyl, C2-C6 alkenyl, C2-C6 alkynyl, C3-C10 cycloalkyl, 4-10 membered heterocycloalkyl, C6-C10 aryl, and 4-10 membered heteroaryl, and —(C1-C3 alkyl)(C6-C10 aryl), and substituted with 0, 1, 2, 3, or 4 independently selected R$^5$ groups, or a salt thereof.

12. The method of claim 11, wherein the aldehyde, the heterocycloalkane, and the reagent are simultaneously reacted.

13. The method of claim 11, wherein the aldehyde and the heterocycloalkane react to form a reaction product and wherein the reaction product reacts with the reagent.

14. The method of claim 11, wherein the aldehyde and the reagent react to form a reaction product and wherein the reaction product reacts with the heterocycloalkane.

15. The method of claim 11, wherein the heterocycloalkane and the reagent react to form a reaction product and wherein the reaction product reacts with the aldehyde.

16. The compound of claim 1, wherein R$^6$ is selected from C6-C10 aryl, —(C1-C3 alkyl)(C6-C10 aryl), and 4-10 membered heteroaryl, and substituted with 0, 1, 2, 3, or 4 independently selected R$^5$ groups.

17. The compound of claim 1, wherein R$^6$ is selected from C6-C10 aryl, —(C1-C3 alkyl)(C6-C10 aryl), and 4-10 membered heteroaryl, and substituted with 0 or 1 R$^5$ group.

18. The compound of claim 1, wherein each occurrence of R$^1$ is independently selected from C6-C10 aryl and 4-10 membered heteroaryl and wherein each occurrence of R$^1$ is independently substituted with 0, 1, 2, 3, or 4 independently selected R$^5$ groups.

19. A The compound of claim 1, wherein each occurrence of R$^1$ is unsubstituted C6-C10 aryl.

* * * * *